US008969299B2

(12) United States Patent
Karim et al.

(10) Patent No.: US 8,969,299 B2
(45) Date of Patent: *Mar. 3, 2015

(54) THERAPEUTIC AGENTS FOR REGULATING SERUM PHOSPHORUS

(75) Inventors: Felix Karim, Walnut Creek, CA (US); Gregory Bell, Tiburon, CA (US)

(73) Assignee: KAI Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/492,778

(22) Filed: Jun. 8, 2012

(65) Prior Publication Data

US 2013/0150301 A1    Jun. 13, 2013

Related U.S. Application Data

(60) Provisional application No. 61/494,874, filed on Jun. 8, 2011.

(51) Int. Cl.
*C07K 7/06* (2006.01)
*A61K 38/08* (2006.01)
*A61K 45/06* (2006.01)

(52) U.S. Cl.
CPC . *C07K 7/06* (2013.01); *A61K 38/08* (2013.01); *A61K 45/06* (2013.01)
USPC .......................................... 514/13.5; 514/654

(58) Field of Classification Search
CPC ............ A61K 38/08; A61K 45/06; C07K 7/06
See application file for complete search history.

(56) References Cited

U.S. PATENT DOCUMENTS

| | | | |
|---|---|---|---|
| 5,246,925 A | 9/1993 | DeLuca et al. | |
| 5,587,497 A | 12/1996 | DeLuca et al. | |
| 5,602,116 A | 2/1997 | Knutson et al. | |
| 5,688,489 A | 11/1997 | Peers et al. | |
| 5,837,218 A | 11/1998 | Peers et al. | |
| 5,861,386 A | 1/1999 | Knutson et al. | |
| 5,869,473 A | 2/1999 | Knutson et al. | |
| 6,031,003 A | 2/2000 | Nemeth et al. | |
| 6,051,567 A | 4/2000 | Abrahamson et al. | |
| 6,165,977 A | 12/2000 | Mochly-Rosen | |
| 6,265,392 B1 | 7/2001 | Abrahamson et al. | |
| 6,274,169 B1 | 8/2001 | Abrahamson et al. | |
| 6,290,665 B1* | 9/2001 | Utterberg ..................... 604/4.01 | |
| 6,855,693 B2 | 2/2005 | Mochly-Rosen et al. | |
| 6,903,083 B2 | 6/2005 | Knutson et al. | |
| 7,081,444 B2 | 7/2006 | Mochly-Rosen | |
| 7,265,092 B2 | 9/2007 | Li | |
| 2003/0036627 A1 | 2/2003 | Montelaro et al. | |
| 2004/0018976 A1 | 1/2004 | Feder et al. | |
| 2005/0187156 A1 | 8/2005 | Mochly-Rosen | |
| 2006/0153867 A1 | 7/2006 | Li | |
| 2007/0066514 A1 | 3/2007 | Haberberger et al. | |
| 2008/0249016 A1 | 10/2008 | Henriksen et al. | |
| 2009/0023652 A1 | 1/2009 | Bell et al. | |
| 2011/0028394 A1* | 2/2011 | Karim et al. ................ 514/11.8 | |

FOREIGN PATENT DOCUMENTS

| | | |
|---|---|---|
| CA | 2145214 A1 | 8/1996 |
| JP | 2000336099 A | 12/2000 |
| WO | WO 92/08476 A1 | 5/1992 |
| WO | WO 95/06056 A1 | 3/1995 |
| WO | WO 99/47173 A2 | 9/1999 |
| WO | WO 02/062396 A2 | 8/2002 |
| WO | WO 02/070547 A1 | 9/2002 |
| WO | WO 03/082923 A1 | 10/2003 |
| WO | WO 2004/093821 A2 | 11/2004 |
| WO | WO 2005/049647 A2 | 6/2005 |
| WO | WO 2005/059124 A2 | 6/2005 |
| WO | WO 2005/072340 A2 | 8/2005 |
| WO | WO 2007/038172 A2 | 4/2007 |
| WO | WO 2008/067199 A2 | 6/2008 |
| WO | WO 2008/089491 A2 | 7/2008 |
| WO | WO 2009/046220 A2 | 4/2009 |
| WO | WO 2009/075773 A2 | 6/2009 |
| WO | WO 2011/014707 A2 | 2/2011 |
| WO | WO 2011014707 A2 * | 2/2011 |

OTHER PUBLICATIONS

Goodman, J Am Soc Nephrol, 13, 2002.*
Arenas, Nephrology Dialysis Transplantation, 22, 6, 2007.*
Martin et al., "The Effect of KAI-4169, a Novel Treatment for Chronic Kidney Disease—Mineral and Bone Disorder, on Serum Phosphorus Kinetics Post-Hemodialysis", (Poster. FR-PO1232) American Society of Nephrology, Philadelphia, Nov. 2011.
McLarnon et al., "Aminoglycoside antibiotics induce pH-sensitive activation of the calcium-sensing receptor", Biochem. Biophys. Res. Commun., vol. 297, No. 1, pp. 71-7 (2002).
Mendoza et al., "Direct upregulation of parathyroid calcium-sensing receptor and vitamin D receptor by calcimimetics in uremic rats", Am. J. Physiol. Renal. Physiol., vol. 296, No. 3, pp. F605- F613 (2009).
Miller et al., "RACK1 regulates Src-mediated Sam68 and p190RhoGAP signaling", Oncogene, vol. 23, pp. 5682-5686 (2004).
Miyamae et al., "Activation of epsilon protein kinase C correlates with a cardioprotective effect of regular ethanol consumption", PNAS, vol. 95, No. 14, pp. 8262-8267 (1998).

(Continued)

*Primary Examiner* — Susan Tran
*Assistant Examiner* — William Craigo
(74) *Attorney, Agent, or Firm* — McDermott Will & Emery LLP

(57) ABSTRACT

Methods for modulating serum phosphorus levels are described, wherein calcimimetic agents are administered to a subject in need thereof. In one embodiment, the compound is cinacalcet, and in other embodiments the compound is comprised of a contiguous sequence of subunits, $X_1$—$X_2$—$X_3$—$X_4$—$X_5$—$X_6$—$X_7$, wherein the $X_1$ subunit comprises a thiol-containing moiety and the distribution of charge on the $X_2$-$X_7$ subunits. The compound, when administered at selected times to a patient undergoing dialysis, lowers serum phosphorus levels, relative to pre-dosing levels, and achieves a sustained reduced level for a period of time after administration.

10 Claims, 3 Drawing Sheets

(56) References Cited

OTHER PUBLICATIONS

Mizobuchi et al., "Calcimimetic compound upregulates decreased calcium-sensing receptor expression level in parathyroid glands of rats with chronic renal insufficiency", J. Am. Soc. Nephrol., vol. 15, No. 10, pp. 2579-2587 (2004).
Mochly-Rosen et al., "A protein kinase C isozyme is translocated to cytoskeletal elements on activation", Cell Regul., vol. 1, No. 9, pp. 693-706 (1990).
Mochly-Rosen et al., "Intracellular receptors for activated protein kinase C: Identification of a binding site for the enzyme", J. Biol. Chem., vol. 266, No. 23, pp. 14866-14868 (1991).
Mochly-Rosen et al., "Identification of intracellular receptor proteins for activated protein kinase C", PNAS, vol. 88, pp. 3997-4000 (1991).
Mochly-Rosen et al., "p65 fragments homologous to the C2 region of protein kinase C, bind to the intracellular receptors for protein kinase C", Biochemistry, vol. 31, No. 35, pp. 8120-8124 (1992).
Mochly-Rosen, "Localization of protein kinases by anchoring proteins: A theme in signal transduction", Science, vol. 268, pp. 247-251 (1995).
Mochly-Rosen et al., "Intraction of protein kinase C with RACK1, a receptor for activated C-kinase: A role in beta protein kinase C mediated signal transduction", Biochem. Soc. Trans., vol. 23, No. 3, pp. 596-600 (1995).
Mochly-Rosen and Gordon, "Anchoring proteins for protein kinase C: A means for isozyme selectivity", Faseb J., vol. 12, No. 1, pp. 35-42 (1998).
Mochly-Rosen and Kauvar, "Modulating protein kinase C signal transduction", Adv. Pharmacol., vol. 44, pp. 91-145 (1998).
Mochly-Rosen et al., "Cardiotrophic effects of protein kinase C epsilon: analysis by in vivo modulation of PKCepsilon translocation", Circ. Res., vol. 86, No. 11, pp. 1173-1179 (2000).
Mochly-Rosen and Kauvar, "Pharmacological regulation of network kinetics by protein kinase C localization", Semin. Immunol., vol. 12, No. 1, pp. 55-61 (2000).
Mochly-Rosen et al., "Spontaneous occurrence of an inhibitor of protein kinase C localization in a thyroid cancer cell line: role in thyroid tumorigenesis", Adv. Enzyme Regul., vol. 41, pp. 87-97 (2001).
Moe et al., "R-568 reduces ectopic calcification in a rat model of chronic kidney disease—mineral bone disorder (CKD-MBD)", Nephrol. Dial. Transplant, vol. 24, No. 8, pp. 2371-2377 (2009).
Mukherjee et al., "Protein kinase C isoforrn activation and endothelin-1 mediated defects in myocyte contractility after cardioplegic arrest and reperfusion", Circulation, vol. 114, Suppl. 1, pp. I308-I313 (2006).
Mun et al., "A double mutation in the extracellular Ca2+-sensing receptor's venus flytrap domain that selectively disables L-amino acid sensing", J. Biol. Chem., vol. 280, No. 32, pp. 29067-29072 (2005).
Mun et al., "The Venus Fly Trap domain of the extracellular Ca2+-sensing receptor is required for L-amino acid sensing", J. Biol. Chem., vol. 279, No. 50, pp. 51739-51744 (2004).
Murriel and Mochly-Rosen, "Opposing roles of delta and epsilonPKC in cardiac ischemia and reperfusion: Targeting the apoptic machinery", Arch. Biochem. Biophys., vol. 420, No. 2, pp. 246-254 (2003).
Murriel et al., "Protein kinase Cdelta activation induces apoptosis in response to cardiac ischemia and reperfusion damage: A mechanism involving BAD and the mitochondria", J. Biol. Chem., vol. 279, No. 46, pp. 47985-47991 (2004).
Nagano and Nemeth, "Functional proteins involved in regulation of intracellular Ca(2+) for drug development: the extracellular calcium receptor and an innovative medical approach to control secondary hyperparathyroidism by calcimimetrics", J. Pharmacol. Sci., vol. 97, pp. 355-360 (2005).
Nagano, "Pharmacological and clinical properties of calcimimetrics: calcium receptor activators that afford an innovative approach to controlling hyperparathyroidism", Pharmacol. Ther., vol. 109, No. 3, pp. 339-365 (2006).

Navarro et al., "Toxicological and pharmacological effects of D-arginine", Basic Clin. Pharmacol. Toxicol., vol. 97, No. 3, pp. 149-154 (2005).
Nemeth et al., "Calcimimetrics with potent and selective activity on the parathroid calcium receptor", PNAS, vol. 95, pp. 4040-4045 (1998).
Nemeth and Fox, "Calcimimetic Compounds: a Direct Approach to Controlling Plasma Levels of Parathyroid Hormone in Hyperparathyroidism", Trends Endocrinol. Metab., vol. 10, No. 2, pp. 66-71 (1999).
Nemeth, "Pharmacodynamics of the type II calcimimetic compound cinacalcet HCl", J. Pharm. Exp. Ther., vol. 38, pp. 627-635 (2004).
Office Action mailed Mar. 9, 2011 with respect to U.S. Appl. No. 11/941,857.
Pace et al., "Dimerization of the calcium-sensing receptor occurs within the extracellular domain and is eliminated by Cys→ Ser mutations at Cys101 and Cys236", J. Biol. Chem., vol. 274, vol. 17, pp. 11629-11934 (1999).
Parada et al., "Transient attenuation of protein kinase Cepsilon can terminate a chronic hyperalgesic state in the rat", Neuroscience, vol. 120, No. 1, pp. 219-226 (2003).
Parada et al., "Chronic hyperalgesic priming in the rat involves a novel interaction between cAMP and PKCepsilon second messenger pathways", Pain, vol. 113, No. 1-2, pp. 185-190 (2005).
Pastori et al., "Delivery of proteins and peptides into live cells by means of protein transduction domains: potential application to organ and cell transplantation", Transplantation, vol. 77, No. 11, pp. 1627-1631 (2004).
Pickthorn et al., "PK/PD Modeling of Transdermal Delivery of a Novel Peptide, KAI-4169, for the Treatment of Chronic Kidney Disease—Bone and Mineral Disorder (CKD-MBD)", (Poster: FR-PO1245) American Society of Nephrology, Philadelphia, Nov. 2011.
Pitchford et al., "Nicotinic acetylcholine receptor desensitization is regulated by activation-induced extracellular adenosine accumulation", J. Neurosci., vol. 12, No. 11, pp. 4540-4544 (1992).
Potts et al., "*Protamine: a powerful in vivo inhibitor of bone resorption*", Calcif. Tissue Int., vol. 36, vol. 2, pp. 189-193 (1984).
Price et al., "Artery calcification in uremic rats is increased by a low protein diet and prevented by treatment with ibandronate", Kidney Int., vol. 70, No. 9, pp. 1577-83 (2006).
Quinn et al., "Ca2+-sensing receptor: a target for polyamines", Am. J. Physiol., vol. 273, No. 4, Pt. 1, pp. C1315-C1323 (1997).
Raval et al., "Epsilon PKC is required for the induction of tolerance by ischemic and NMDA-mediated preconditioning in the organotypic hippocampal slice", J. Neirosci., vol. 23, No. 2, pp. 384-391 (2003).
Raval et al., "Protein kinase C delta cleavage initiates an aberrant signal transduction pathway after cardiac arrest and oxygen glucose deprivation", J. Cereb. Blood Flow Metab., vol. 25, No. 6, pp. 730-741 (2005).
Ray et al., "Elucidation of the role of peptide linker in calcium-sensing receptor activation process", J. Biol. Chem., vol. 282, No. 8, pp. 5310-5317 (2007).
Ray et al., "The role of cysteines and charged amino acids in extracellular loops of the human Ca(2+) receptor in cell surface expression and receptor activation processes", Endocrinology, vol. 145, No. 8, pp. 3892-3903 (2004).
Ray et al., "Identification of the cysteine residues in the amino-terminal extracellular domain of the human Ca(2+) receptor critical for dimerization. Implications for function of monomeric Ca(2+) receptor", J. Biol. Chem., vol. 274, No. 39, pp. 27642-27650 (1999).
Ray and Northup, "Evidence for distinct cation and calcimimetic compound (NPS 568) recognition domains in the transmembrane regions of the human Ca2+ receptor", J. Biol. Chem., vol. 277, No. 21, pp. 18908-18913 (2002).
Rey et al., "Amino acid-stimulated Ca2+ oscillations produced by the Ca2+-sensing receptor are mediated by a phospholipase C/inositol 1,4,5-trisphosphate-independent pathway that requires G12, Rho, filamin-A, and the actin cytoskeleton", J. Biol. Chem., vol. 280, No. 24, pp. 22875-22882 (2005).
Riccardi et al., "Novel regulatory aspects of the extracellular Ca2+-sensing receptor, CaR", Pflugers Arch., vol. 458, No. 6, pp. 1007-1022 (2009).

(56) References Cited

OTHER PUBLICATIONS

Riccardi and Gamba, "The many roles of the calcium-sensing receptor in health and disease", Arch. Med. Res., vol. 30, No. 6, pp. 436-448 (1999).

Ridge et al., "Dopamine-induced exocytosis of Na.K-ATPase is dependent on activation of protein kinase C-epsilon and -delta", Mol. Biol. Cell., vol. 13, No. 4, pp. 1381-1389 (2002).

Robia et al., "Novel determinant of PKC-epsilon anchoring at cardiac Z-lines", Am. J. Physiol. Heart Circ. Physiol., vol. 289, No. 5, pp. H1941-H1950 (2005).

Rodriguez et al., "Characterization of the binding and phosphorylation of cardiac calsequestrin by epsilon protein kinase C", FEBS Lett., vol. 454, No. 3, pp. 240-246 (1999).

Hrabak, "Common ligands of G-protein-coupled receptors and arginine-utilizing enzymes", Br. J. Pharmacol., vol. 147, No. 8, pp. 835-837 (2006).

Hu et al., "Evidence for functional role of epsilonPKC isozyme in the regulation of cardiac CA(2+) channels", Am. J. Physiol. Heart Circ. Physiol., vol. 279, No. 6, pp. H2658-H2664 (2000).

Hu, "Allosteric modulators of the human calcium-sensing receptor: structures, sites of action, and therapeutic potentials", Endocr. Metab. Immune Disord. Drug Targets, vol. 8, No. 3, pp. 192-197 (2008).

Hu et al., "Identification of acidic residues in the extracellular loops of the seven-transmembrane domain of the human Ca2+ receptor critical for response to Ca2+ and a positive allosteric modulator", J. Biol. Chem., vol. 277, 48, pp. 46622-46631 (2002).

Hu and Spiegel, "Structure and function of the human calcium-sensing receptor: insights from natural and engineered mutations and allosteric modulators", J. Cell. Mol. Med., vol. 11, 5, pp. 908-922 (2007).

Huang et al., "Multiple Ca(2+)-binding sites in the extracellular domain of the Ca(2+)-sensing receptor corresponding to cooperative Ca(2+) response", Biochemistry, vol. 48, No. 2, pp. 388-398 (2009).

Hudecz et al., "Medium-sized peptides as built in carriers for biologically active compounds", Med. Res. Rev., vol. 25, No. 6, pp. 679-736 (2005).

Hundle et al., "An inhibitory fragment derived from protein kinase Cepsilon prevents enhancement of nerve growth factor responses by ethanol and phorbol esters", J. Biol. Chem., vol. 272, No. 23, pp. 15028-15035 (1997).

Ikari et al., "Activation of a polyvalent cation-sensing receptor decreases magnesium transport via claudin-16", Biochim. Biophys. Acta., vol. 1778, No. 1, pp. 283-290 (2008).

Ikeno et al., "Impaired perfusion after myocardial infarction is due to reperfusion-induced deltaPKC-mediated myocardial damage", Cardiovasc. Res., vol. 73, No. 4, pp. 699-709 (2007).

Inagaki et al., "Tissue angiotensin during progression of ventricular hypertrophy to heart failure in hypertensive rats; differential effects on PKCε and PKCβ", J. Mol. Cell Cardiol., pp. 1-9 (2002).

Inagaki et al., "Additive protection of the ischemic heart ex vivo by combined treatment with delta-protein kinase C inhibitor and epsilon-protein kinase C activator", Circulation, vol. 108, pp. 869-875 (2003).

Inagaki et al., "Inhibition of delta-protein kinase C protects against reperfusion injury of the ischemic heart in vivo", Circulation vol. 108, No. 19, pp. 2304-2307 (2003).

Inagaki et al., "Cardioprotection by epsilon-protein kinase C activation from ischemia: Continuous delivery and antiarrythmic effect of an epsilon-protein kinase C-activating peptide", Circulation, vol. 111, No. 1, pp. 44-50 (2005).

Inagaki and Mochly-Rosen, "DeltaPKC-mediated activation of epsilonPKC in ethanol-induced cardiac protection from ischemia", J. Mol. Cell Cardiol., vol. 39, No. 2, pp. 203-211 (2005).

Inagaki et al., "Epsilon protein kinase C as a potential therapeutic target for the ischemic heart", Cardiovasc. Res., vol. 70, No. 2, pp. 222-230 (2006).

International Search Report from PCT Patent Application No. PCT/US2008/051706 mailed Sep. 24, 2008, application now published as International Patent Publication No. WO 2008/089491 A2 on Jul. 24, 2008.

International Search Report from related PCT Patent Application No. PCT/US2010/043792 mailed Apr. 26, 2011, application now published as International patent Publication No. WO2011/014707 on Feb. 3, 2011.

Jaburek et al., "Mitochondrial PKC epsilon and mitochondrial ATP-sensitive K+ channel copurify and coreconstitute to form a functioning signaling module in proteoliposomes", Circ Res., vol. 99, pp. 873-883 (2006).

Jin et al., "Cardioprotection mediated by sphingosine-1-phosphate and ganglioside GM-1 in wild-type and PKC epsilon knockout mouse hearts", Am. J. Physiol. Heart Circ Physiol., vol. 282, No. 6, pp. H1970-H1977 (2002).

Johnson and Mochly-Rosen, "Inhibition of the spontaneous rate of contraction of neonatal cardiac myocytes by protein kinase C isozymes. A putative role for the epsilon isozyme", Circ. Res., vol. 76, No. 4, pp. 654-663 (1995).

Johnson et al., "Prolonged phorbol ester treatment down-regulates protein kinase C isozymes and increases contraction rate in neonatal cardiac myocytes", Life Sci., vol. 57, No. 11, pp. 1027-1038 (1995).

Johnson et al., "An improved permeabilization protocol for the introduction of peptides into cardiac myocytes. Application to protein kinase C research", Circ. Res., vol. 79, pp. 1086-1099 (1996).

Johnson et al., "A protein kinase C translocation inhibitor as an isozyme-selective antagonist of cardiac function", J. Biol. Chem., vol. 271, No. 40, pp. 24962-24966 (1996).

Johnson et al., "Protamine-induced hypocalcemia", Endocrinology, vol. 87, No. 6, pp. 1211-1217 (1970).

Joseph et al., "Hyperalgesic priming in the rat demonstrates marked sexual dimorphism", Pain, vol. 105, No. 1-2, pp. 143-150 (2003).

Kheifets et al., "Protein kinase C delta (deltaPKC)-annexin V interaction: a required step in deltaPKC translocation and function", J. Biol. Chem., vol. 281, No. 32, pp. 23218-23226 (2006).

Knauf et al., "Involvement of protein kinase Cepsilon (PKCepsilon) in thyroid cell death. A truncated chimeric PKCepsilon cloned from a thyroid cancer cell line protects thyroid cells from apoptosis", J. Biol. Chem., vol. 274, No. 33, pp. 23414-23425 (1999).

Knauf et al., "Isozyme-specific abnormalitites of PKC in thyroid cancer. Evidence for post-transcriptional changes in PKC epsilon", J. Clin. Endocrinol. Metab., vol. 85, No. 5, pp. 2150-2159 (2002).

Koponen et al., "Prevention of NMDA-induced death of cortical neurons by inhibition of protein kinase Czeta", J. Neurochem., vol. 86, No. 2, pp. 442-450 (2003).

Lagunoff et al., "Agents that release histamine from mast cells", Ann. Rev. Pharmacol. Toxicol., vol. 23, pp. 331-351 (1983).

Lange-Asschenfeldt et al., "Epsilon protein kinase C mediated ischemic tolerance requires activation of the extracellular regulated kinase pathway in the organotypic hippocampal slice", J. Cereb. Blood Flow Metab., vol. 24, No. 6, pp. 636-645 (2004).

Laudanna et al., "Evidence of zeta protein kinase C involvement in a polymorphic neutrophil integrin-dependent adhesion and chemotaxis", J. Biol. Chem., vol. 273, No. 46, pp. 30306-30315 (1998).

Lee et al., "Allosteric activation of the extracellular Ca2+-sensing receptor by L-amino acids enhances ERK1/2 phosphorylation", Biochem. J., vol. 404, No. 1, pp. 141-149 (2007).

Li et al., "Protein kinase Cgamma mediates ethanol withdrawal hyper-responsiveness of NMDA receptor currents in spinal cord motor neurons", Br. J. Pharmacol., vol. 144, No. 3, pp. 301-307 (2005).

Liu et al., "Protein kinase C-epsilon is responsible for the protection of the preconditioning in rabbit cardiomyocytes", J. Mol. Cell Cardiol., vol. 31, No. 10, pp. 1937-1948 (1999).

Lien et al., "Effects of cinacalcet on bone mineral density in patients with secondary hyperparathyroidism", Nephrol. Dial. Transplant, vol. 20, No. 6, pp. 1232-1237 (2005).

Luthman et al., "The hypocalcemic response to protamine as a measure of bone resorption", Acta Vet. Scand., vol. 14, No. 3, pp. 428-435 (1973).

Luthman and Korpe, "Vitamin D status and hypocalcemic response to protamine in exercised and non-exercised dairy cows", Acta Vet. Scand., vol. 34, No. 1, pp. 53-57 (1993).

(56) References Cited

OTHER PUBLICATIONS

Ma et al., "Characterization of highly efficacious allosteric agonists of the human calcium-sensing receptor", J. Pharmacol Exp. Ther., vol. 337, No. 1, pp. 275-284 (2011).

MacKay and Mochly-Rosen, "An inhibitor of p38 mitogen-activated protein kinase neonatal cardiac myocytes from ischemia", J. Biol. Chem., vol. 274, No. 10, pp. 6272-6279 (1999).

MacKay and Mochly-Rosen, "Involvement of a p38 mitogen-activated protein kinase phosphatase in protecting neonatal rat cardiac myocytes from ischemia", J. Mol. Cell Cardiol., vol. 32, No. 8, pp. 1585-1588 (2000).

MacKay and Mochly-Rosen, "Arachidonic acid protects neonatal rat cardiac myocytes from ischemic injury through epsilon protein kinaseC", Cardiovasc. Res., vol. 50, No. 1, pp. 65-74 (2001).

MacKay and Mochly-Rosen, "Localization, anchoring, and function of protein kinase C isozymes in the heart", J. Mol. Cell. Cardiol., vol. 33, No. 7, pp. 1301-1307 (2001).

MacLean, "KAI-4169: A Novel Calcium Sensing Receptor (CaSR) Agonist for the Treatment of CKD-MBD", TIDES Meeting Boston May 2011.

Magno et al., "The calcium-sensing receptor: a molecular perspective", Endocr. Rev., vol. 32, No. 1, pp. 3-30 (2011).

Malhotra et al., "PKC-{epsilon}-dependent survival signals in diabetic hearts", Am. J. Physiol. Heart Circ. Physiol., vol. 289, No. 4, pp. H1343-H1350 (2005).

Marie, "The calcium-sensing receptor in bone cells: a potential therapeutic target in osteoporosis", Bone, vol. 46, No. 3, pp. 571-576 (2010).

Marinovic et al., "Preconditioning by isoflurane induces lasting sensitization of the cardiac sarcolemmal adenosine triphosphate-sensitive potassium channel by a protein kinase C-delta-mediated mechanism", Anesthesiology, vol. 103, No. 3, pp. 540-547 (2005).

Martin et al., "KAI-4169, a Novel Peptide for the Treatment of Chronic Kidney Disease—Mineral and Bone Disorder, in a Phase I Study in Healthy Males", (Poster: FR-PO 1238) American Society of Nephrology, Philadelphia, Nov. 2011.

Martin et al., "Characterzation of KAI-4169, A Novel Peptide for the Treatment of Chronic Kidney Disease Mineral and Bone Disorder, in a Single-dose Study in Hemodialysis Subjects", (Poster: FR-PO1256) American Society of Nephrology, Philadelphia, Nov. 2011.

Abes et al., "Vectorization of morpholino oligomers by the (R-Ahx-R)4 peptide allows efficient splicing correction in the absence of endosomolytic agents", J. Contr. Rel., vol. 116, No. 3, pp. 304-313 (2006).

International Search Report from PCT Patent Application No. PCT/US2007/085024 mailed Jul. 7, 2008, application now published as International Patent Publication No. WO 2008/067199 on Jun. 5, 2008.

Arenas et al., "Implementation of K/DOQI clinical practice guidelines for bone metabolism and disease in chronice kidney disease after the introduction of cinacalet in a population of patients on chronic haemodialysis", Nephrology Dialysis Transplantation, vol. 22, No. 6, pp. 1639-1644 (2007).

Goodman "Calcimimetic agents for the treatment of secondary hyperparathyroidism", Seminars in Nephrology, vol. 24, No. 5, pp. 460-463 (2004).

Harris et al., "Pharmacokinetics, pharmacodynamics, and safety of cinacalcet hydrochloride in hemodialysis patients at doses up to 200 mg once daily", American J. Kidney Dis., vol. 44, No, 6. pp. 1070-1076 (2004).

International Search Report from related PCT Patent Application No. PCT/US2012/041759 mailed on Sep. 26, 2012.

Schaefer et al., "Efficacy of cinacalcet administered with the first meal after dialysis: the SENSOR study", Clinical Nephrology, vol. 70, No. 2, pp. 126-134 (2008).

Padhi et al., "Clinical pharmacokinetic and pharmacodynamic profile of cinacalcet hydrochloride", Clinical Pharmacoknetics, vol. 48, No. 5, pp. 303-311 (2009).

Platt et al., "Middle-term use of cinacalcet in peadiatric dialysis patients", J. Int. Ped. Nephrol., vol. 25, No. 1, pp. 143-148 (2009).

Rodriguez et al., "RACK1, a protein kinase C anchoring protein, coordinates the binding of activated protein kinase C and select pleckstrin homology domains in vitro", Biochemistry, vol. 38, No. 42, pp. 13787-13794 (1999).

Rodriguez et al., "The calcium-sensing receptor: a key factor in the pathogenesis of secondary hyperparathyroidism", Am. J. Physiol. Renal Physiol., vol. 288, No. 2, pp. F253-F264 (2005).

Ron and Mochly-Rosen, "Agonists and antagonists of protein kinase C function, derived from its binding proteins", J. Biol. Chem., vol. 269, No. 34, pp. 21395-21398 (1994).

Ron and Mochly-Rosen, "An autoregulatory region in protein kinase C: the psuedoanchoring site", PNAS, vol. 92, No. 2, pp. 492-496 (1995).

Ron et al., "Cloning of an intracellular receptor for protein kinase C: a homolog of the beta subunit of G proteins", PNAS, vol. 91, No. 3, pp. 839-843 (1994).

Ron et al., "C2 region-derived peptides inhibit translocation and function of beta protein kinase C in vivo", J. Biol. Chem., vol. 270, No. 41, pp. 24180-24187 (1995).

Saidak et al., "Agonists and allosteric modulators of the calcium-sensing receptor and their therapeutic applications", Mol Pharmacol., vol. 76, No. 6. pp. 1131-1144. (2009).

Sajid-Crockett et al., "Cinacalcet for the treatment of primary hyperparathyroidism", Metabolism, vol. 57, No. 4, pp. 517-521 (2008).

Satoh et al., "PKC-delta and -epsilon regulate NF-kappaB activation induced by cholecystokinin and TNF-alpha in pancreatic acinar cells", Am. J. Physiol. Gastrointest. Liver Physiol., vol. 287, No. 3, pp. G582-G591 (2004).

Schechtman et al., "Adaptor proteins in protein kinase C-mediated signal transduction", Oncogene, vol. 20, No. 44, pp. 6339-6347 (2001).

Schechtman and Mochly-Rosen, "Isozyme-specific inhibitors and activators of protein kinase C", Methods Enxymol., vol. 345, pp. 470-489 (2002).

Schechtman et al., "Overlay method for detecting protein-protein interactions", Methods Mol. Biol., vol. 233, pp. 351-357 (2003).

Schechtman et al., "Glutathione S-transferase pull-down assay", Methods Mol. Biol., vol. 233, pp. 345-350 (2003).

Schechtman et al., "A critical intramolecular interaction for protein kinase Cepsilon translocation", J. Biol. Chem., vol. 279, No. 16, pp. 15831-15840 (2004).

Shen et al.,"The PK/PD Relationship of a Novel Peptide, KAI-4169 Following Single-Dose Administration to Healthy Young Males", Endocrine Society 93rd Annual Meeting (ENDO 2011), Boston Jun. 4-8, 2011 (Endocr Rev 32: P1-23) (2011).

Shimoni and Liu, "Role of PKC in autocrine regulation of rat ventricular K+ currents by angiotensin and endothelin", Am. J. Physiol. Heart Circ. Physiol., vol. 284, No. 4, pp. H1168-H1181 (2003).

Shoback et al., "The calcimimetic cinacalcet normalizes serum calcium in subjects with primary hyperparathyroidism", J. Clin. Endocrinol. Metab., vol. 88, No. 12, pp. 5644-5649 (2003).

Shoback et al., "Relationship between parathyroid hormone secretion and cytosolic calcium concentration in dispersed bovine parathyroid cells", Proc. Natl. Acad. Sci. USA., vol. 81, No. 10, pp. 3113-3117 (1984).

Shumilla et al., "Ethanol withdrawal-associated allodynia and hyperalgesia: age-dependent regulation by protein kinase C epsilon and gamma isoenzymes", J. Pain, vol. 6, No. 8, pp. 535-549 (2005).

Simon et al., "Characterization of PKC2 a gene encoding a second protein kinase C isotype of *Saccharomyces cerevisiae*", Curr. Biol., vol. 3, No. 12, pp. 813-821 (1993).

Simon et al., "The identification and purification of a mammalian-like protein kinase C in the yeast *Saccharomyces cerevisiae*", Proc. R. Soc. Lond., vol. 243, No. 1307, pp. 165-171 (1991).

Smith and Mochly-Rosen, "Inhibition of protein kinase C function by injection of intracellular receptors for the enzyme", Biochem. Biophys. Res. Commun., vol. 188, No. 3, pp. 1235-1240 (1992).

Smith et al., "The HIV nef protein associates with protein kinase C theta", J. Biol. Chem., vol. 271, No. 28, pp. 16753-16757 (1996).

(56) References Cited

OTHER PUBLICATIONS

Souroujon and Mochly-Rosen, "Peptide modulators of protein-protein interactions in intracellular signaling", Nat Biotechnol., vol. 16, No. 10, pp. 919-924 (1998).
Souroujon et al., "State-specific monoclonal antibodies identify an intermediate state in epsilon protein kinase C activation", J. Biol. Chem., vol. 279, No. 17, pp. 17617-17624 (2004).
Stebbins and Mochly-Rosen, "Binding specificity for RACK1 resides in the V5 region of beta II kinase C", J. Biol. Chem., vol. 276, No. 32, pp. 29644-29650 (2001).
Stoelting et al., "Haemodynamic changes and circulating histamine concentrations following protamine administration to patients and dogs", Can. Anaesth. Soc. J., vol. 31, No. 5, pp. 534-540 (1984).
Sweitzer et al., "Exaggerated Nociceptive responses on morphine withdrawal: Roles of protein kinase C epsilon and gamma", Pain, No. 110, No. 1-2, pp. 281-289 (2004).
Sweitzer et al., "Protein kinase C epsilon and gamma: Involvement in formalin-induced nociception in neonatal rats", J. Pharmacol. Exp. Ther., vol. 309, No. 2, pp. 616-625 (2004).
Szabo et al., "RSA 2004: combined basic research satellite symposium—session three: alcohol and mitochondrial metabolism: at the crossroads of life and death", Alcohol Clin. Exp. Res., vol. 29, No. 9, pp. 1749-1752 (2005).
Tanaka et al., "Suppression of graft coronary artery disease by a brief treatment with a selective epsilonPKC activator and a deltaPKC inhibitor in murine cardiac allografts", Circulation, vol. 110, No. 11, Suppl. 1, pp. ii94-ii199 (2004).
Tanaka et al., "Inhibition of heart transplant injury and graft coronary artery disease after prolonged organ ischemia by selective protein kinase C regulators", J. Thorac. Cardiovasc. Surg., vol. 129, No. 5, pp. 1160-1167 (2005).
Trivedi et al., "Recent updates on the calcium-sensing receptor as a drug target", Curr. Med. Chem., vol. 15, No. 2, pp. 178-186 (2008).
Vallentin and Mochly-Rosen, "RBCK1, a protein kinase Cbetal (PKCbetal)-interacting protein, regulates PKCbeta-dependent function", J. Biol. Chem., vol. 282, No. 3, pp. 1650-1657 (2007).
Van Baal et al., "Translocation of diacylglycerol kinase theta from cytosol to plasma membrane in response to activation of G protein-coupled receptors and protein kinase C", vol. 280, No. 11, pp. 9870-9878 (2005).
Wada et al., "Calcimimetic NPS R-568 prevents parathyroid hyperplasia in rats with severe secondary hyperparathyroidism", Kidney Int., vol. 57, No. 1, pp. 50-58 (2000).
Walter et al., "Preclinical PK and PD relationship for KAI-4169, a novel peptide agonist of the calcium sensing receptor", Endocrine Society, 93$^{rd}$ Annual Meeting, Boston Jun. 4-8, 2011.
Walter et al., "KAI-4169, a Novel Peptide Agonist of the Calcium Sensing Receptor, Suppresses Parathyroid Hormone, Parathyroid Gland Hyperplasia and Ectopic Calcification in a Rodent Model of Chronic Renal Dysfunction", (Poster: FR-PO1222) American Society of Nephrology, Philadelphia, Nov. 2011.
Wang et al., "Cell-specific role for epsilon- and beta-protein kinase C isozymes in protecting cortical neurons and astrocytes from ischemia-like injury", Neuropharmacology, p. 47, No. 1, pp. 136-145 (2004).
Ward et al., "Disulfide bonds in the extracellular calcium-polyvalent cation-sensing receptor correlate with dimer formation and its response to divalent cations in vitro", J. Biol. Chem., vol. 273, No. 23, pp. 14476-14483 (1998).
Ward et al., "Aminoglycosides induce acute cell signaling and chronic cell death in renal cells that express the calcium-sensing receptor", J. Am. Soc. Nephrol., vol. 16, No. 5, pp. 1236-1244 (2005).
Way et al., "Identification of PKC-isophorm-specific biological actions using pharmacological approaches", TIPS, vol. 21, No. 5, pp. 181-187 (2000).
Wu et al., "Epsilon protein kinase C in pathological myocardial hypertrophy. Analysis by combined transgenic expression of translocation modifiers and Galphaq", J. Biol. Chem., vol. 275, No. 39, pp. 29927-29930 (2000).

Xiao et al., "PKC isozyme selective regulation of cloned human cardiac delayed slow rectifier K current", Biochem. Biophys. Res. Commun., vol. 306, No. 4, pp. 1019-1025 (2003).
Xiao et al., "Evidence for functional role of epsilonPKC isozyme in the regulation of cardiac Na(+) channels", Am. J. Physiol. Cell. Physiol., vol. 281, No. 5, pp. C1477-C1486 (2001).
Yang et al., "Discovery and structure-activity relationships of trisubstituted pyrimidines/pyridines as novel calcium-sensing receptor antagonists", J. Med. Chem., vol. 52, No. 4, pp. 1204-1208 (2009).
Ye et al., "Amyloid-beta proteins activate Ca(2+)-permeable channels through calcium-sensing receptors", J. Neurosci. Res., vol. 47, No. 5, pp. 547-554 (1997).
Yedovitzky et al., "Translocation inhibitors define specificity of protein kinase C isoenzymes in pancreatic beta-cells", J. Biol. Chem., vol. 272, No. 3, pp. 1417-1420 (1997).
Young and Rozengurt, "Amino acids and Ca2+ stimulate different patterns of Ca2+ oscillations through the Ca2+-sensing receptor", Am. J. Physiol. Cell Physiol., vol. 282, No. 6, pp. C1414-C1422 (2002).
Zhang et al., "C2 region-derived peptides of beta-protein kinase C regulates cardiac Ca2+ channels", Circ. Res., vol. 80, No. 5, pp. 720-729 (1997).
Zhang et al., "L-phenylalanine and NPS R-467 synergistically potentiate the function of the extracellular calcium-sensing receptor through distinct sites", J. Biol. Chem., vol. 277, No. 37, pp. 33736-33741 (2002).
Zhang et al., Three adjacent serines in the extracellular domains of the CaR are required for L-amino acid-mediated potentiation of receptor function, J. Biol. Chem., vol. 277, No. 37, pp. 33727-33735 (2002).
Zhang et al., "The extracellular calcium-sensing receptor dimerizes through multiple types of intermolecular interactions", J. Biol. Chem., vol. 276, No. 7, pp. 5316-5322 (2001).
Zhou et al., "Deifferential activation of protein kinase C isozymes by phorbol ester and collagen in human skin microvascular endothelial cells", J. Invest. Dermatol., vol. 107, No. 2, pp. 248-252 (1996).
Aizawa et al., "Protein kinase C-epsilon primes the cardiac sarcolemmal adenosine triphosphate-sensitive potassium channel to modulation by isoflurane", Anesthesiology, vol. 101, No. 2, pp. 381-389 (2004).
Aladren, "Cinacalcet reduces vascular and soft tissue calcification in secondary hyperparathyroidism (SHPT) in hemodialysis patients", Clin. Nephrol., vol. 71, No. 2, pp. 207-213, (2009).
Alessandri-Haber et al., "A transient receptor potential vanilloid 4-dependent mechanism of hyperalgesia is engaged by concerted action of inflammatory mediators", J. Neurosci., vol. 26, No. 14, pp. 3864-3874 (2006).
Aley et al., "Chronic hypersensitivity for inflammatory nociceptor sensitization mediated by the epsilon isozyme of protein kinase C", J. Neurosci., vol. 20, No. 12, pp. 4680-4685 (2000).
Aley and Levine, "Contribution of 5- and 12-lipoxygenase products to mechanical hyperalgesia induced by prostaglandin E(2) and epinephrine in the rat", Exp. Brain Res., vol. 148, No. 4, pp. 482-487 (2003).
Almirall et al., "Effects of cinacalcet on vascular calcification in haemodialysis patients", Nephrol. Dial. Transplant, vol. 25, No. 8, p. 2800 (2010).
Anderson et al., "The effect of protamine derivatives on calcium metabolism in patients with malignancy", Br. J. Cancer., vol. 21, No. 1, pp. 48-55 (1967).
Antonsen et al., "A calcimimetic agent acutely suppresses parathyroid hormone levels in patients with chronic renal failure", Rapid communication, Kidney Int., vol. 53, No. 1, pp. 223-227 (1998).
Apple et al., "Differential effects of protein kinase C isoform activation in endothelin-mediated myocyte contractile dysfunction with cardioplegic arrest and reperfusion", Ann. Thorac. Surg., vol. 82, No. 2, pp. 664-671 (2006).
Arey et al., "A novel calcium-sensing receptor antagonist transiently stimulates parathyroid hormone secretion in vivo", Endocrinology, vol. 146, No. 4, pp. 2015-2022 (2005).

(56) References Cited

OTHER PUBLICATIONS

Aridor et al., "Exocytosis in mast cells by basic secretagogues: evidence for direct activation of GTP-binding proteins", J. Cell. Biol., vol. 111, pp. 909-917 (1990).
Bakker et al., "8R-lisuride is a potent stereospecific histamine H1-receptor partial agonist", Mol. Pharmacol., vol. 65, No. 3, pp. 538-549 (2004).
Banci et al., "Molecular dynamics of characterization of the C2 domain of protein kinase Cbeta", J. Biol. Chem., vol. 277, No. 15, pp. 12988-12997 (2002).
Baruch et al., "KAI-4169, a novel Peptide Agonist of the Calcium Sensing Receptor For the Treatment of Secondary Hyperparathyroidism" Endocrine Society 93rd Annual Meeting (ENDO 2011), Boston Jun. 4-8, 2011 (Endocr Rev 32. P2-98) (2011).
Begley et al., "Biodistribution of intracellularly acting peptides conjugated reversibly to tat", Biochem. Biophys. Res. Commun., vol. 318, No. 4, pp. 949-954 (2004).
Bell et al., "Calcimimetic KAI-4169 Reduces Parathyroid Hormone (PTH) Dose-dependently", (Poster#:SA23) ISN World Congress of Nephrology, Vancouver, Apr. 8-12, 2011.
Besena et al., "Activation of protein kinase C epsilon inhibits the two-pore domain K+ channel, TASK-1, inducing repolarization abnormalities in cardiac ventricular myocytes", J. Biol. Chem., vol. 279, No. 32, pp. 33154-33160 (2004).
Block et al., "The impact of calcimimetics on mineral metabolism and secondary hyperparathyroidism in end-stage renal disease", Kidney Int. Suppl., vol. 87, pp. S131-S136 (2003).
Block et al., "Cinacalcet for secondary hyperparathyroidism in patients receiving hemodialysis", N. Engl. J. Med., vol. 350, No. 15, pp. 1516-1525 (2004).
Block et al., "Results of a Phase 2 study evaluating the safety and efficacy of KAI-4169, a novel peptide for the treatment of chronic kidney disease—mineral and bone disorder in hemodialysis subjects", (Poster: LBCT-P03147) American Society of Nephrology, Philadelphia, Nov. 2011.
Braun and Mochly-Rosen, "Opposing effects of delta- and zeta-protein kinase C isozymes on cardiac fibroblast proliferation: Use of isozyme-selective inhibitors", J. Mol. Cell Cardiol., vol. 35, No. 8, pp. 895-903 (2003).
Brietwieser, "Calcium sensing receptors and calcium oscillations: calcium as a first messenger", Curr. Top. Dev. Biol., vol. 73, pp. 85-114 (2006).
Brennan and Conigrave, "Regulation of cellular signal transduction pathways by the extracellular calcium-sensing receptor", Curr. Pharm. Biotechnol., vol. 10, No. 3, pp. 270-281 (2009).
Bright et al., "Protein kinase C delta mediates cerebral reperfusion injury in vivo", J. Neuroscience, vol. 24, No. 31, pp. 6880-6888 (2004).
Bright and Mochly-Rosen, "The role of protein kinase C in cerebral ischemic and reperfusion in injury", Stroke, vol. 36, No. 12, pp. 2781-2790 (2005).
Brown et al., "Polyarginine, polylysine, and protamine mimic the effects of high extracellular calcium concentrations on dispersed bovine parathyroid cells", J. Bone Miner. Res., vol. 6, pp. 1217-1225 (1991).
Brown et al., "Decreased calcium-sensing receptor expression in hyperplastic parathyroid glands of uremic rats: role of dietary phosphate", Kidney Int., vol. 55, pp. 1284-1292 (1999).
Brown, "Clinical utility of calcimimetics targeting the extracellular calcium-sensing receptor (CaSR)", Biochem. Pharmacol., vol. 80, No. 3, pp. 297-307 (2010).
Brown et al., "Cloning and characterization of an extracellular Ca(2+)-sensing receptor from bovine parathyroid", Nature, vol. 366, No. 6455, pp. 575-580 (1993).
Brown et al., "Quabain and low extracellular potassium inhibit PTH secretion from bovine parathyroid cells by a mechanism that does not involve increases in the cytosolic calcium concentration", Metabolism, vol. 36, No. 1, pp. 36-42 (1987).
Brown et al., "Neomycin mimics the effects of high extracellular calcium concentrations on parathyroid function in dispersed bovine parathyroid cells", Endocrinology, vol. 128, No. 6, pp. 3047-3054 (1991).
Brown and MacLeod, "Extracellular calcium sensing and extracellular calcium signaling", Physiol. Rev., vol. 81, No. 1, pp. 239-297 (2001).
Brzoska et al., "The product of the ataxia-telangiectasia group D complementing gene, ATDC, interacts with a protein kinase C substrate and inhibitor", PNAS, vol. 92, No. 17, pp. 7824-7828 (1995).
Buhagier et al., "Protein kinase Cepsilon contributes to regulation of the sarcolemmal Na(+)-K(+) pump", Am. J. Physiol. Cell Physiol., vol. 281, No. 3, pp. C1059-C1063 (2001).
Busque et al., "L-type amino acids stimulate gastric acid secretion by activation of the calcium-sensing receptor in parietal cells", Am. J. Physiol. Gastrointest. Liver Physiol., vol. 289 No. 4, pp. G664-G669 (2005).
Cardone et al., "Phorbol myristate acetate-mediated stimulation of trancytosis and apical recycling in MDCK cells", J. Cell. Biol., vol. 124, No. 5, pp. 717-727 (1994).
Cardone et al., "Signal transduction by the polymeric immunoglobulin receptor suggests a role in regulation of receptor transcytosis", J. Cell. Biol., vol. 133, No. 5, pp. 997-1005 (1996).
Caudrillier et al., "Calcium-sensing receptor as a potential modulator of vascular calcification in chronic kidney disease", J. Nephrol., vol. 23, No. 1, pp. 17-22 (2010).
Chang and Tepperman, "Effects of selective PKC isoform activation and inhibition on TNF-α-induced injury and apoptosis in human intestinal epithelial cells", British Journal of Pharmacology, vol. 140, pp. 41-52 (2003).
Chattopadhyay et al., "Regulation of secretion of PTHrP by Ca(2+)-sensing receptor in human astrocytes, astrocytomas, and meningiomas", Am. J. Physiol. Cell Physiol., vol. 279(3): C691-C699 (2000).
Chaudary et al., "The adenosine transporter, mENT1, is a target for adenosine receptor signaling and protein kinase Cepsilon in hypoxic and pharmacological preconditioning in the mouse cardiomyocyte cell line, HL-1", J. Pharmacol. Exp. Ther., vol. 310, No. 3, pp. 1190-1198 (2004).
Chen et al., "Cardioprotection from ischemia by a brief exposure to physiological levels of ethanol: Role of epsilon protein kinase C", PNAS, vol. 96, No. 22, pp. 12784-12789 (1999).
Chen et al., "Molecular transporters for peptides: delivery of a cardioprotective εPKC agonist peptide into cells and intact ischemic heart using a transport system. RΔ", Chem. Biol., vol. 8, pp. 1123-1129 (2001).
Chen et al., "Opposing cardioprotective actions and parallel hypertrophic effects of delta PKC and epsilon PKC", PNAS, vol. 98, No. 20, pp. 11114-11119 (2001).
Chen and Goodman, "Role of the calcium-sensing receptor in parathyroid gland physiology", Am. J. Physiol. Renal Physiol., vol. 286, No. 6, pp. F1005-F1011 (2004).
Church et al., "Characterization of histamine secretion from mechanically dispersed human lung mast cells: effects of anti-IgE, calcium ionophore A23187, compound 48/80, and basic polypeptides", J. Immunol., vol. 129, No. 5, pp. 2116-2121 (1982).
Churchill et al., "Reperfusion-induced translocation of deltaPKC to cardiac mitochondria prevents pyruvate dehydrogenase reactivation", Circ. Res., vol. 97, No. 1, pp. 78-85 (2005).
Colloton et al., "Cinacalcet HCl attenuates parathyroid hyperplasia in a rat model of secondary hyperparathyroidism", Kidney Int., vol. 67, No. 2, pp. 467-476 (2005).
Conigrave and Brown, "Taste receptors in the gastrointestinal tract. II. L-amino acid sensing by calcium-sensing receptors: implications for GI physiology", Am. J. Physiol. Gastrointest Liver Physiol., vol. 291, No. 5, pp. G753-G761 (2006).
Conigrave et al., "Dietary protein and bone health: roles of amino acid-sensing receptors in the control of calcium metabolism and bone homeostasis", Annu. Rev. Nutr., vol. 28, pp. 24.1-24.25 (2008).
Conigrave et al., "L-amino acid sensing by the calcium-sensing receptor: a general mechanism for coupling protein and calcium metabolism?", Eur. J. Clin. Nutr., vol. 56, No. 11, pp. 1072-1080 (2002).

(56) References Cited

OTHER PUBLICATIONS

Conigrave et al., "Physiological significance of L-amino acid sensino by extracellular Ca(2+)-sensing receptors", Biochem. Soc. Trans., vol. 35, Pt. 5, pp. 1195-1198 (2007).
Conigrave et al., "L-amino acids regulate parathyroid hormone secretion"J. Biol. Chem., vol. 279, No. 37, pp. 38151-38159 (2004).
Conigrave et al., "Aromatic L-amino acids activate the calcium-sensing receptor", J. Nutr., vol. 137, No. 6 Suppl. 1, pp. 1524S-1527S, discussion 1548S (2007).
Conigrave et al., "L-amino acid sensing by the extracellular Ca2+-sensing receptor", Proc. Natl. Acad. Sci. USA, vol. 97, No. 9, pp. 4814-4819 (2000).
Conigrave et al., "Cooperative multi-modal sensing and therapeutic implications of the extracellular Ca(2+) sensing receptor", Trends Pharmacol, Sci., vol. 10, pp. 401-407 (2000).
Csukai et al., "The coatomer protein beta'-COP, a selective binding protein (RACK) for protein kinase Cepsilon", J. Biol. Chem., vol. 272, No. 46, pp. 29200-29206 (1997). Csukai, et al., "The coatomer protein beta'-COP, a selective binding protein (RACK) for protein kinase Cepsilon", J. Biol. Chem., vol. 272, No. 46, pp. 29200-29206 (1997).
Csukai and Mochly-Rosen, "Molecular genetic approaches. II. Expression-interaction cloning," Methods Mol. Biol., vol. 88, pp. 133-139 (1998).
Csukai and Mochly-Rosen, "Pharmacologic modulation of protein kinase C isozymes: The role of RACKs and subcellular localization", Pharmacological Research, vol. 39, No. 4, pp. 253-259 (1999).
Dehgani et al., "Subcellular localization of protein kinase C delta and epsilon affects transcriptional and post-transcriptional processes in four-cell mouse embryos", Reproduction, vol. 130, No. 4, pp. 453-465 (2005).
Delaney, "Managing bone mineral disorders in CKD: an overview of current therapies", J. Ren. Care, vol. 35, Suppl 1, pp. 107-110 (2009).
Dell et al., "The betagamma subunit of heterotrimeric G proteins interacts with RACK 1 and two other WD repeat proteins", J. Biol. Chem., vol. 277, No. 51, pp. 49888-49895 (2002).
Dempsey et al., "Protein kinase C isozymes and the regulation of divers cell responses", Am. J. Physiol. Lung Cell Mol. Physiol., vol. 279, No. 3, pp. L429-L438 (2000).
Diamond et al., "The role of adenosine and adenosine transport in ethanol-induced cellular tolerance and dependence. possible biologic and genetic markers of alcoholism", Ann. N.Y. Acad. Sci., vol. 625, pp. 473-487 (1991).
Dina et al., "Primary afferent second messenger cascades interact with specific integrin subunits in producing inflammatory hyperalgesia", Pain, vol. 115, No. 1-2, pp. 191-203 (2005).
Disatnik et al., "Distinct responses of protein kinase C isozymes to c-erbB-2 activation in SKBR-3 human breast carcinoma cells", Cell Growth Differ., vol. 5, No. 8, pp. 873-880 (1994).
Disatnik et al., "Localization of protein kinase C isozymes in cardiac myocytes", Exp. Cell. Res., vol. 210, No. 2, pp. 287-297 (1994).
Disatnik, et al., "Phospholipase C-gamma 1 binding to intracellular receptors for activated protein kinase C", PNAS, vol. 91, No. 2, pp. 559-563 (1994).
Disatnik et al., "Stimulus-dependent subcellular localization of activated protein kinase C, a study with acidic fibroblast growth factor and transforming growth factor-beta 1 in cardiac myocytes", J. Mol. Cell. Cardiol., vol. 27, No. 11, pp. 2473-2481 (1995).
Disatnik et al., "Sequential activation of individual PKC isozymes in integrin-mediated muscle cell spreading: A role of MARCKS in an integrin signaling pathway", J. Cell Science, vol. 115, pp. 2151-2163 (2002).
Dorn et al., "Sustained in vivo cardiac protection by a rationally designed peptide that causes epsilon protein kinase C translocation", PNAS, vol. 96, No. 22, pp. 12798-12803 (1999).
Dorn and Mochly-Rosen, "Intracellular transport mechanisms of signal transducers", Annu. Rev. Physiol., vol. 64, pp. 407-429 (2002).
Endemann et al., "Cytotoxicity of pEGFP vector is due to residues encoded by multiple cloning site", Anal. Biochem., vol. 313, No. 2, pp. 345-347 (2003).

Endemann and Mochly-Rosen, "Methods for detecting binding proteins: An introduction", Methods Mol. Biol., vol. 233, pp. 307-325 (2003).
Fan et al., "Mutational analysis of the cysteines in the extracellular domain of the human Ca2+ receptor: effects on cell surface expression, dimerization and signal transduction", FEBS Lett., vol. 436, No. 3, pp. 353-356 (1998).
Fasciotto et al., "Pancreastatin, a presumed product of chromogranin-A (secretory protein-I) processing, inhibits secretion from porcine parathyroid cells in culture", Endocrinology, vol. 125, No. 3, pp. 1617-1622 (1989).
Final Office Action mailed Nov. 18, 2011 with respect to U.S. Appl. No. 11/941,857.
Foreman and Lichtenstein, "Induction of histamine secretion by polycations", Biochim. Biophys. Acta, vol. 629, No. 3, pp. 587-603 (1980).
Garcia-Navarro et al., "Development expression of protein kinase C subspecies in rat brain-pituitary axis", Mol. Cell Endocrinol., vol. 103, No. 1, pp. 133-138 (1994).
Geibel et al., "Calcium-sensing receptor abrogates secretagogue-induced increases in intestinal net fluid secretion by enhancing cyclic nucleotide destruction", Proc. Natl. Acad. Sci. USA, vol. 103, No. 25, pp. 9390-9397 (2006).
Gogusev et al., "Depressed expression of calcium receptor in parathyroid gland tissue of patients with hyperparathyroidism", Kidney Int., vol. 51, No. 1, pp. 328-336 (1997).
Goodman, "Recent developments in the management of secondary hyperparathyroidism", Kidney Int., vol. 59, No. 3, pp. 1187-1201 (2001).
Goodman et al., "The calcimimetic agent AMB 073 lowers plasma parathyroid hormone levels in hemodialysis patients with secondary hyperparathyroidism", J. Am. Soc. Nephrol., vol. 13, No. 4, pp. 1017-1024 (2002).
Goto et al., "Heparin, protamine, and ionized calcium in vitro and in vivo", Anesth. Analg., vol. 64, No. 11, pp. 1081-1084 (1985).
Gray et al., "A selective epsilon-protein kinase C antagonist inhibits protection of cardiac myocytes from hypoxia-induced cell death", J. Biological Chemistry, vol. 272, No. 49, pp. 30945-30951 (1997).
Gray et al., "Preservation of base-line hemodynamic function and loss of inducible cardioprotection in adult mice lacking protein kinase C epsilon", J. Biol. Chem., vol. 279, No. 5, pp. 3596-3604 (2004).
Gregory et al., "Increased particulate partitioning of PKC epsilon reverses susceptibility of phospholamban knockout hearts to ischemic injury", J. Mol. Cell Cardiol., vol. 36, No. 2, pp. 313-318 (2004).
Gunn and Gaffney, "Clinical and laboratory features of calcium-sensing receptor disorders: a systematic review", Ann. Clin. Biochem., vol. 41, Pt. 6, pp. 441-458 (2004).
Gustafsson et al., "Discovery of a class of calcium sensing receptor positive allosteric modulators: 1-(benzothiazol-2-yl)-1-phenylethanols", Bioorg Med Chem Lett., vol. 20, No. 19, pp. 5918-5921 (2010).
Handlogten et al., "Ca(2+)-sensing receptor is a promiscuous divalent cation sensor that responds to lead", Am. J. Physiol. Renal. Physiol., vol. 279, No. 6, pp. F1083-F1091 (2000).
Hauache et al., "Effects of a calcimimetic compound and naturally activating mutations on the human Ca2+ receptor and on Ca2+ receptor/metabotropic glutamate chimeric receptors", Endocrinology, vol. 141, No. 11, pp. 4156-4163 (2000).
Hebert, "Therapeutic use of calcimimetics", Annu. Rev. Med., vol. 57 pp. 349-364 (2006).
Helman et al., "Molecular cloning and primary structure of human chromogranin A (secretory protein I) cDNA", J. Biol. Chem., vol. 263, No. 23, pp. 11559-11563 (1988).
Hendy et al., "Chapter 3 calcium-sensing receptor and associated diseases", Prog. Mol. Biol. Transl. Sci., vol. 89, pp. 31-95 (2009).
Henley et al., "The calcimimetic AMG 641 abrogates parathyroid hyperplasia, bone and vascular calcification abnormalities in uremic rats", Eur. J. Pharmacol., vol. 616, No. 1-3, pp. 306-313 (2009).
Hofer, "Review series on the extracellular Ca(2+)-sensing receptor", J. Cell. Mol. Med., vol. 11, No. 5, pp. 906-907 (2007).

(56) References Cited

OTHER PUBLICATIONS

Hofer and Brown, "Extracellular calcium sensing and signaling", Nat. Rev. Mol. Cell Biol., vol. 4, No. 7, pp. 530-538 (2003).
Hong et al., "Effect of D-amino acid substitution on the stability, the secondary structure, and the activity of membrane-active peptide", Biochem. Pharmacol., vol. 58, No. 11, pp. 1775-1780 (1999).
Hool, "Protein kinase C isozyme selective peptides—A current view of what they tell us about location and function of isozymes in the heart", Current Pharmaceutical Design, vol. 11, pp. 549-559 (2005).
Pologe et al., "Primary structure and subcellular localization of the knob-associated histidine-rich protein of *Plasmodium falciparum*", PNAS USA, vol. 84, pp. 7139-7143 (1987).
Spormann et al., "Carboxypeptidase yscS: gtene structure and function of the vacular enzyme", Eur. J. Biochem., vol. 197, pp. 399-405 (1991).
Yu et al., "Two-dimensional NMR studies and secondary structure of cobrotoxin in aqueous solution", Eur. J. Biochem., vol. 193, pp. 789-799 (1990).

* cited by examiner

THERAPEUTIC AGENTS FOR REGULATING SERUM PHOSPHORUS

CROSS-REFERENCE TO RELATED APPLICATIONS

This application claims the benefit of U.S. Provisional Application No. 61/494,874, filed Jun. 8, 2011, incorporated herein by reference in its entirety.

TECHNICAL FIELD

The present disclosure relates to a method for treating hemodialysis patients with hyperphosphatemia comprising administering a calcium sensing receptor (CaSR) agonist.

REFERENCE TO SEQUENCE LISTING

A Sequence Listing is being submitted electronically via EFS in the form of a text file, created Jun. 8, 2012, and named "632008021US00.txt" (87,702 bytes), the contents of which are incorporated herein by reference in their entirety.

BACKGROUND

Phosphate (phosphorus) is critical for a variety of biologic and cellular processes. Phosphate along with calcium is a major component of the skeletal system, providing mineral strength to bone. Phosphate is also an integral component of nucleic acids as well as the phosphate bonds of the cellular energy molecule ATP. Phosphate functions as a buffer in bone, serum, and urine. Accordingly, physiological levels of phosphate in the blood are careful regulated by a variety of organ systems of in the body The bulk of total body phosphate (85%) is in the bone as part of the mineralized extracellular matrix. About 300 mg of phosphate enters and exits bone tissue each day. Excessive losses or failure to add phosphate to bone leads to osteomalacia. The kidneys along with parathyroid hormone (PTH), which is secreted by the parathyroid gland, play an important role in phosphate homeostasis by controlling the excretion of phosphate, while the digestive tract and the hormone Vitamin D play yet another important role in phosphate homeostasis by controlling its absorption from the diet.

The kidneys provide the primary route of excretion for excess phosphorus absorbed from ingested food or liberated from bone. Consequently in chronic kidney disease (CKD) patients as kidney function worsens elevation in blood levels of serum phosphorus directly stimulate PTH secretion by the parathyroid glands, which can then further exacerbate the homeostasis by liberating more phosphorus from bone. Since failing kidneys can no longer adequately handle the burden of excess phosphorus, CKD patients must control their diet to reduce phosphate intake. Increases in serum phosphorus level begin early in CKD disease progression in Stage 3 and Stage 4 and can get progressively worse as kidney function declines. Stage 5 CKD patients (also referred to as end stage renal disease or ESRD) usually under go regular dialysis to remove excess toxins and metabolites, including phosphorus, and yet also require treatment with phosphate-binding agents in an attempt to bind-up dietary phosphates and thereby prevent systemic absorption as a way to lower serum phosphorus to acceptable levels. In the U.S., approximately 90% of dialysis patients are treated with a phosphate control product.

Elevated serum phosphorus has been linked to the development and progression of hyperparathyroidism, bone disease such as osteodystropy and soft tissue mineralization and is associated with an increased risk of death in hemodialysis patients (Block et al., 1998, Am J. Kidney Dis, 31:607-617; Block et al., 2000, Am J. Kidney Dis, 35:1226-1237; Palmer et al., 2011, JAMA, 305:1119-1127). Severe hyperphosphatemia (serum phosphate level >6.5 mg/dL (>2.10 mmol/L)) has been associated directly with increased overall and cardiovascular mortality in hemodialysis (HD) patients (Palmer et al., 2011, JAMA, 305:1119-1127), and even moderate hyperphosphatemia (3.0 to 5.0 mg/dL) is associated with increased cardiovascular risk in these patients. Currently, clinical guidelines recommend maintaining phosphate levels within normal range (3.0 to 5.0 mg/dL (0.97 to 1.61 mmol/L)). However, even moderate to severe hyperphosphatemia (phosphate, 5.01 to 6.5 mg/dL (1.62 to 2.10 mmol/L)) needs to be addressed since it is an independent mortality risk factor in HD patients, and phosphate binders therapy alone do not always reduce serum phosphorus levels sufficiently.

Hyperphosphatemia also leads to secondary hyperparathyroidism (SHPT) and elevated blood levels of PTH by: (a) lowering the levels of ionized calcium; (b) interfering with the production of 1,25(OH)2D3; and (c) by directly affecting PTH secretion. These processes lead to high-turnover bone disease and other adverse consequences of excess PTH.

Current clinical guidelines recommend maintaining phosphate levels within normal range (3.0 to 5.0 mg/dL (0.97 to 1.61 mmol/L)). It is generally accepted that control of serum phosphorus will lead to improved clinical outcomes and survival in hemodialysis patients. Approaches to lowering serum phosphorus include dialysis, dietary phosphorus restriction and oral phosphate binders.

Serum phosphate declines rapidly in the first 1-2 hours of dialysis and then a plateau is reached during which serum phosphate remains relatively constant. After dialysis, serum phosphorus concentration rises quickly in the first few hours, typically reaching a concentration approximating the pre-dialysis value 6-8 hours later (Haas et al., 1991, Nephrol Dial Transplant, 2:108-113; Sugisaki et al., 1983 Trans Am Soc Artif Intern Organs, 29:38-43). This phenomenon has been referred to as "phosphate rebound." In some cases, phosphate rebound produces higher phosphate levels than were initially present.

The control of phosphorus often remains unsatisfactory in dialyzed patients. Accordingly, there is a continuing need for methods for treating hyperphosphatemia in hemodialysis patients. In particular, methods for reducing phosphate rebound are desired.

BRIEF SUMMARY

In one aspect, a method is provided for treatment of hyperphosphatemia in hemodialysis patients.

In another aspect, a method is provided for reducing phosphate rebound in hemodialysis patients.

In another aspect, a treatment method comprises administering to a patient receiving dialysis (hemodialysis or peritoneal dialysis) a compound comprising the formula $X_1$—$X_2$—$X_3$—$X_4$—$X_5$—$X_6$—$X_7$ wherein $X_1$ is a subunit comprising a thiol-containing group; $X_5$ is a cationic subunit; $X_6$ is a non-cationic subunit; $X_7$ is a cationic a subunit; and at least two of $X_2$, $X_3$ and $X_4$ are independently a cationic subunit. The compound is administered within about 5 minutes, 10 minutes, 15 minutes, 20 minutes, 30 minutes, 45 minutes, 1 hour, 2 hours, 3 hours, 4 hours after hemodialysis or within about 3 hours, 2 hours, 1 hour, 45 minutes, 30 minutes, 20 minutes, 15 minutes, 10 minutes, 5 minutes before completion of a hemodialysis session, and wherein the administration is effective to maintain a post-hemodialysis serum phosphorus level that is lower than a pre-hemodialysis serum phosphorus level for a period of at least about 1 hour, 2 hours, 3 hours, 4 hours, 5 hours, 6 hours, 24 hours, 48 hours, 72 hours after completion of dialysis, or the time until the next hemodialysis session.

In one embodiment, the compound is administered within a period beginning about 15 minutes prior to completion of hemodialysis and ending about 3 hours after completion of hemodialysis, and wherein said administering is effective to maintain a post-hemodialysis serum phosphorus level that is lower than a pre-hemodialysis serum phosphorus level for a period of at least about 6 hours after completion of dialysis In one embodiment, the agonist is Ac-c(C)arrrar-NH$_2$ (SEQ ID NO:3).

In another embodiment, the agonist is a pharmaceutically salt of SEQ ID NO:3. An exemplary embodiment is an agonist that is a hydrochloride salt of SEQ ID NO:3.

In one embodiment, the agonist is administered within about 1 hour after dialysis or within about 30 minutes after dialysis. In a preferred embodiment, the agonist is administered during the rinse back procedure at the end of dialysis. In another embodiment, the agonist is administered within 5 hours before completion of dialysis, daily at least about 1 hour before completion of a dialysis session. In one embodiment, the dialysis is hemodialysis.

In another embodiment, the agonist is administered during a rinse back procedure at the end of dialysis.

In other embodiments, the patient has been diagnosed with end stage renal disease or chronic kidney disease and receives a treatment as described herein.

In other embodiments, the patient is being treated with a drug that binds phosphate prior to and/or at the time of being treated as described herein.

In yet other embodiments, the patient has chronic kidney disease associated with diabetes. In still other embodiments, the patient has chronic kidney disease associated with hypertension that is being treated by dialysis and receives a treatment as described herein. In other embodiments, the patient is being treated via dialysis for secondary hyperparathyroidism or primary hyperparathyroidism and receives a treatment as described herein.

In yet another aspect, a method is provided, the method comprising administering to a patient undergoing hemodialysis a calcium sensing receptor agonist, wherein the agonist is administered within about 5 minutes, 10 minutes, 15 minutes, 20 minutes, 30 minutes, 45 minutes, 1 hour, 2 hours, 3 hours, 4 hours after conclusion of hemodialysis or within about 3 hours, 2 hours, 1 hour, 45 minutes, 30 minutes, 20 minutes, 15 minutes, 10 minutes, 5 minutes before completion of hemodialysis, and wherein the administering is effective to maintain a post-hemodialysis serum phosphorus level that is lower than a pre-hemodialysis serum phosphorus level for a period of at least about 1 hour, 2 hours, 3 hours, 4 hours, 5 hours, 6 hours, 24 hours, 48 hours, 72 hours or the time until the next hemodialysis is commenced. In a preferred embodiment, the agonist is administered during the rinse back procedure at the end of dialysis.

In one embodiment of this aspect, the calcium sensing receptor agonist is not a compound of the form $X_1$—$X_2$—$X_3$—$X_4$—$X_5$—$X_6$—$X_7$ wherein $X_1$ is a subunit comprising a thiol-containing group; $X_5$ is a cationic subunit; $X_6$ is a non-cationic subunit; $X_7$ is a cationic a subunit; and at least two of $X_2$, $X_3$ and $X_4$ are independently a cationic subunit.

In one embodiment, the calcium sensing receptor agonist is a calcimimetic. In other embodiments, the calcimimetic is cinacalcet hydrochloride ($C_{22}H_{22}F_3N.HCl$).

In still another aspect, a method for treating hyperphosphatemia in a patient who receives at least on a periodic basis hemodialysis is provided. The method comprises administering to the patient an effective amount of a calcium sensing receptor (CaSR) agonist, wherein the agonist is administered within about 18 hours after conclusion of hemodialysis or less than about 3 hours before completion of hemodialysis, and wherein the administering is effective to maintain a post-hemodialysis serum phosphorus level that is lower than a pre-hemodialysis serum phosphorus level for a period of at least about 6 hours.

In one embodiment, the agonist is administered less than 30 minutes before completion of dialysis.

In one embodiment, the agonist is cinacalcet hydrochloride. In another embodiment, the agonist is a compound of the form $X_1$—$X_2$—$X_3$—$X_4$—$X_5$—$X_6$—$X_7$ wherein $X_1$ is a subunit comprising a thiol-containing group; $X_5$ is a cationic subunit; $X_6$ is a non-cationic subunit; $X_7$ is a cationic a subunit; and at least two of $X_2$, $X_3$ and $X_4$ are independently a cationic subunit.

In one embodiment, the agonist is Ac-c(C)arrrar-NH$_2$ (SEQ ID NO:3) or a salt thereof.

In other aspects, a method for regulating serum phosphorus concentration in a patient receiving at least on a periodic basis hemodialysis is provided. The method comprises administering to the patient an effective amount of a calcium sensing receptor (CaSR) agonist, wherein the agonist is administered within about 5 minutes, 10 minutes, 15 minutes, 20 minutes, 30 minutes, 45 minutes, 1 hour, 2 hours, 3 hours, 4 hours after conclusion of hemodialysis or less than about 3 hours, 2 hours, 1 hour, 45 minutes, 30 minutes, 20 minutes, 15 minutes, 10 minutes, 5 minutes before completion of hemodialysis. In one embodiment, the administration is effective to maintain a post-hemodialysis serum phosphorus level that is lower than a pre-hemodialysis serum phosphorus level for a period of at least about 1 hour, 2 hours, 3 hours, 4 hours, 5 hours, 6 hours, 24 hours, 48 hours, 72 hours, or the time until the next hemodialysis session is begun. In a preferred embodiment, the agonist is administered during the rinse back procedure at the end of dialysis.

After oral administration of cinacalcet hydrochloride, Cmax is achieved in approximately 2 to 6 hours. Accordingly, in another embodiment, the method comprises administering to the patient an effective amount of cinacalcet hydrochloride, wherein the cinacalcet hydrochloride is administered within about 5 minutes, 10 minutes, 15 minutes, 20 minutes, 30 minutes, 45 minutes, 1 hour, 2 hours, 3 hours, 4 hours after conclusion of hemodialysis or less than about 9 hours, 8 hours, 7 hours, 6 hours, 5 hours, 4 hours, 3 hours, 2 hours, 1 hour, 45 minutes, 30 minutes, 20 minutes, 15 minutes, 10 minutes, 5 minutes before completion of hemodialysis. In one embodiment, the administration is effective to maintain a post-hemodialysis serum phosphorus level that is lower than a pre-hemodialysis serum phosphorus level for a period of at least about 1 hour, 2 hours, 3 hours, 4 hours, 5 hours, 6 hours, 24 hours, 48 hours, 72 hours, or the time until the next hemodialysis session is begun.

In another aspect, a dosing regimen for administration of a compound for treating hyperparathyroidism in a patient undergoing hemodialysis is provided. The dosing regimen comprises administering to the patient a calcium sensing receptor agonist, wherein the agonist is administered within about 5 minutes, 10 minutes, 15 minutes, 20 minutes, 30 minutes, 45 minutes, 1 hour, 2 hours, 3 hours, 4 hours after conclusion of hemodialysis or less than about 3 hours, 2 hours, 1 hour, 45 minutes, 30 minutes, 20 minutes, 15 minutes, 10 minutes, 5 minutes before completion of hemodialysis. In a preferred embodiment, the agonist is administered during the rinse back procedure at the end of dialysis. The regimen is effective to maintain a post-hemodialysis serum phosphorus level that is lower than a pre-hemodialysis serum phosphorus level for a period of at least about 6 hours.

In another aspect, a method for treating hyperphosphatemia in a subject that receives dialysis is provided, wherein the subject is treated with a CaSR agonist compound as described herein. The treatment is effective to provide a post-dialysis serum phosphorus level that is less than a pre-dialysis serum phosphorus level for the duration of a period between dialysis sessions, i.e, the interdialytic period. In one embodiment, the post-dialysis serum phosphorus level is at least about 10%, 15%, 20% or 25% less than a pre-dialysis serum phosphorus level for the duration of the interdialytic period. The CaSR agonist compound is administered in accord with any of the treatment embodiments described herein, for example, before completion of a dialysis session or within about 5 minutes, 10 minutes, 15 minutes, 20 minutes, 30 minutes, 45 minutes, 1 hour, 2 hours, 3 hours, or 4 hours after a dialysis session.

In embodiments of any of the aspects noted herein, the CaSR agonist can be a compound comprising the sequence carrrar (SEQ ID NO:2). In other embodiments, the CaSR agonist is a conjugate comprised of the peptide carrrar (SEQ ID NO:2), where the peptide is conjugated at its N-terminal residue to a Cys residue. In a preferred embodiment, the conjugate is Ac-c(C)arrrar-NH$_2$ (SEQ ID NO:3).

Figure 1:
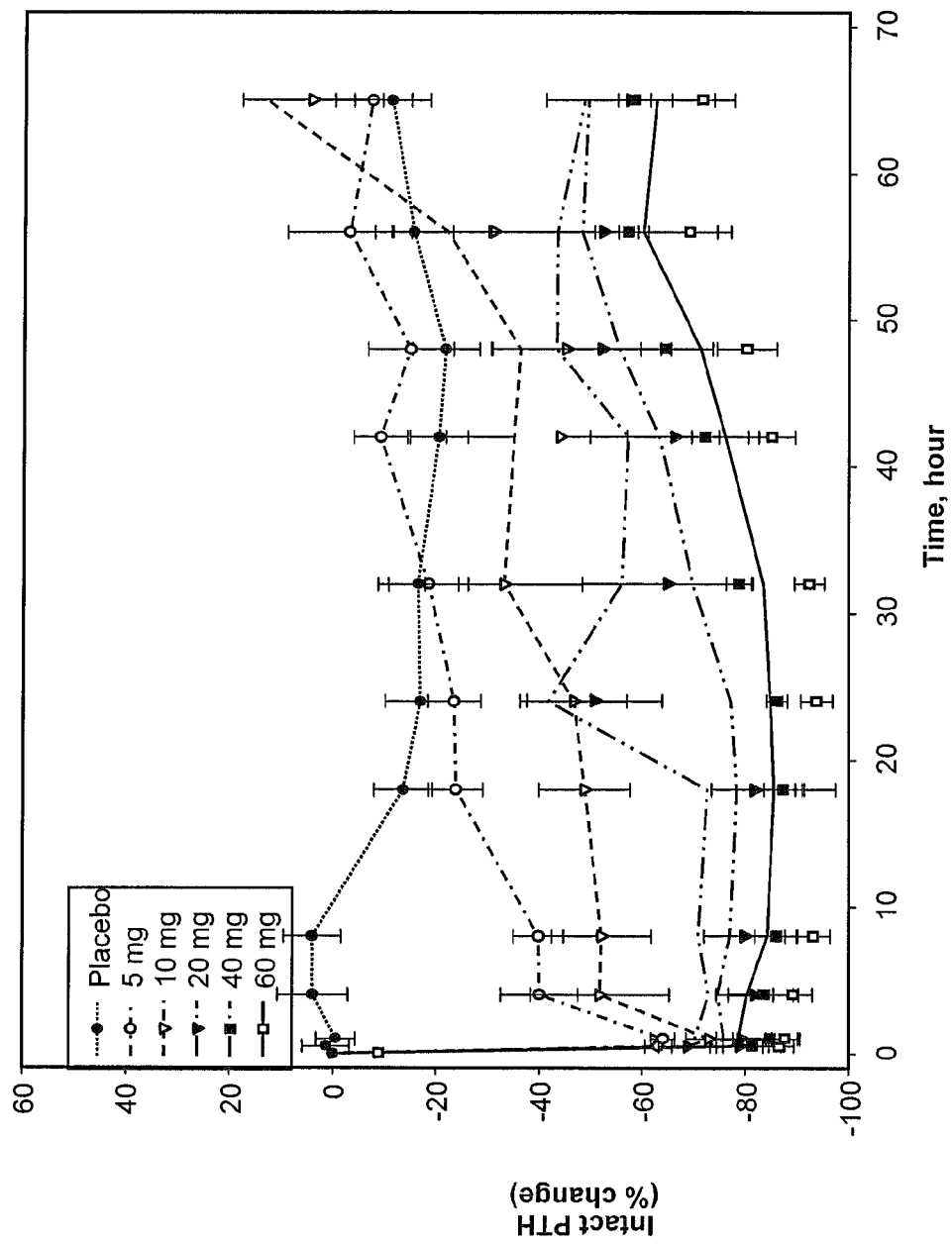
FIG. 1 is a graph showing the percent change in serum intact PTH levels following administration of SEQ ID NO:3 or placebo by intravenous injection shortly after dialysis. Placebo, closed circles; 5 mg SEQ ID NO:3, open circles; 10 mg SEQ ID NO:3, inverted open triangles; 20 mg SEQ ID NO:3, inverted closed triangles; 40 mg SEQ ID NO:3, closed squares; 60 mg SEQ ID NO:3, open squares.

The present subject matter may be understood more readily by reference to the following detailed description of the preferred embodiments and the examples included herein.

DETAILED DESCRIPTION

I. Definitions

Within this application, unless otherwise stated, definitions of the terms and illustration of the techniques of this application may be found in any of several well-known references such as: Sambrook, J., et al., Molecular Cloning: A Laboratory Manual, Cold Spring Harbor Laboratory Press (1989); Goeddel, D., ed., Gene Expression Technology, Methods in Enzymology, 185, Academic Press, San Diego, Calif. (1991); "Guide to Protein Purification" in Deutshcer, M. P., ed., Methods in Enzymology, Academic Press, San Diego, Calif. (1989); Innis, et al., PCR Protocols: A Guide to Methods and Applications, Academic Press, San Diego, Calif. (1990); Freshney, R.I., Culture of Animal Cells: A Manual of Basic Technique, 2nd Ed., Alan Liss, Inc. New York, N.Y. (1987); Murray, E. J., ed., Gene Transfer and Expression Protocols, pp. 109-128, The Humana Press Inc., Clifton, N.J. and Lewin, B., Genes VI, Oxford University Press, New York (1997).

As used herein, the singular form "a", "an", and "the" include plural references unless indicated otherwise. For example, "a" modulator peptide includes one of more modulator peptides.

As used herein, "amino acid" refers to natural and non-natural amino acids. The twenty naturally occurring amino acids (L-isomers) are designated by the three letter code with the prefix "L-" (except for glycine which is achiral) or by the one letter code in upper-case: alanine ("L-Ala" or "A"), arginine ("L-Arg" or "R"), asparagine ("L-Asn" or "N"), aspartic acid ("L-Asp" or "D"), cysteine ("L-Cys" or "C"), glutamine ("L-Gln" or "Q"), glutamic acid ("L-Glu" or "E"), glycine ("Gly" or "G"), histidine ("L-His" or "H"), isoleucine ("L-Ile" or "I"), leucine ("L-Leu" or "L"), lysine ("L-Lys" or "K"), methionine ("L-Met" or "M"), phenylalanine ("L-Phe" or "F"), proline ("L-Pro" or "P"), serine ("L-Ser" or "S"), threonine ("L-Thr" or "T"), tryptophan ("L-Trp" or "W"), tyrosine ("L-Tyr" or "Y") and valine ("L-Val" or "V"). L-norleucine and L-norvaline may be represented as (NLeu) and (NVal), respectively. The nineteen naturally occurring amino acids that are chiral have a corresponding D-isomer which is designated by the three letter code with the prefix "D-" or by the lower-case one letter code: alanine ("D-Ala" or "a"), arginine ("D-Arg" or "r"), asparagine ("D-Asn" or "a"), aspartic acid ("D-Asp" or "d"), cysteine ("D-Cys" or "c"), glutamine ("D-Gln" or "q"), glutamic acid ("D-Glu" or "e"), histidine ("D-His" or "h"), isoleucine ("D-Ile" or "i"), leucine ("D-Leu" or "l"), lysine ("D-Lys" or "k"), methionine ("D-Met" or "m"), phenylalanine ("D-Phe" or "f"), proline ("D-Pro" or "p"), serine ("D-Ser" or "s"), threonine ("D-Thr" or "t"), tryptophan ("D-Trp" or "w"), tyrosine ("D-Tyr" or "y") and valine ("D-Val" or "v"). D-norleucine and D-norvaline may be represented as (dNLeu) and (dNVal), respectively. Although "amino acid residue" is often used in reference to a monomeric subunit of a peptide, polypeptide or protein, and "amino acid" is often used in reference to a free molecule, usage of these terms in the art overlaps and varies. The term "amino acid" and "amino acid residue" are used interchangeably and may refer to a free molecule or a monomeric subunit of a peptide, polypeptide or protein, depending on context.

A "cationic amino acid" intends an amino acid residue that has a net positive charge at physiologic pH (7.4), as is the case, for example, in the amino acid residues where the side chain, or "R group", contains an amine functional group or other functional group that can accept a proton to become positively charged at physiologic pH, such as a guanidine or imidazole moiety. Cationic amino acid residues include arginine, lysine, histidine, 2,3-diaminopropionic acid (Dap), 2,4-diaminobutyric acid (Dab), ornithine, and homoarginine.

A "cationic subunit" intends a subunit that has a net positive charge at physiologic pH (7.4).

As used herein, "conservative amino acid substitutions" are substitutions which do not result in a significant change in the activity or tertiary structure of a selected polypeptide or protein. Such substitutions typically involve replacing a selected amino acid residue with a different amino acid residue having similar physico-chemical properties. Groupings of amino acids and amino acid residues by physico-chemical properties are known to those of skill in the art. For example, among the naturally-occurring amino acids, families of amino acid residues having similar side chains have been defined in the art, and include basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "chemical cross-linking" refers to covalent bonding of two or more molecules.

A peptide or peptide fragment is "derived from" a parent peptide or polypeptide if it has an amino acid sequence that is identical or homologous to at least a contiguous sequence of five amino acid residues, more preferably eight amino acid residues, of the parent peptide or polypeptide.

The compounds described herein may be in the form of pharmaceutically acceptable salts. Pharmaceutically acceptable salts include acid addition salts, such as hydrochloride, hydrobromide, sulfurate, nitrate, phosphorate, acetate, propionate, glycolate, pyruvate, oxalate, malate, malonate, succinate, maleate, fumarate, tartarate, citrate, benzoate, cinnamate, mandelate, methanesulfonate, ethanesulfonate, p-toluene-sulfonate, salicylate and the like, and base addition salts, such as sodium, potassium, calcium, magnesium, lithium, aluminum, zinc, ammonium, ethylenediamine, arginine, piperazine and the like.

As used herein, the term "hyperparathyroidism" refers to primary, secondary and tertiary hyperparathyroidism, unless otherwise indicated.

As used herein, an "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of polypeptides in which the polypeptide is separated from some of the cellular components of the cells in which it is naturally or recombinantly produced. When the polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of polypeptides in which the polypeptide is separated from chemical precursors or other chemicals that are involved in the synthesis of the polypeptide. In one embodiment, the language "substantially free of chemical precursors or other chemicals" includes preparations of a polypeptide having less than about 30% (by dry weight) of chemical precursors or other chemicals, preferably less than about 20% chemical precursors or other chemicals, more preferably less than about 15% chemical precursors or other chemicals, still more preferably less than about 10% chemical precursors or other chemicals, and most preferably less than about 5% chemical precursors or other chemicals. In preferred embodiments, isolated polypeptides, or biologically active portions thereof, lack contaminating polypeptides from the same organism from which the domain polypeptide is derived.

A "non-cationic amino acid" intends an amino acid residue that has no charge or a net negative charge at physiologic pH (7.4), as is the case, for example, in the amino acid residues where the side chain, or "R group", is neutral (neutral polar and neutral non-polar) and acidic. Non-cationic amino acids include those residues with an R group that is a hydrocarbon alkyl or aromatic moiety (e.g., valine, alanine, leucine, isoleucine, phenylalanine); a neutral, polar R group (asparagine, cysteine, glutamine, serine, threonine, tryptophan, tyrosine); or a neutral, non-polar R group (glycine, methionine, proline, valine, isoleucine). Non-cationic amino acids with an acidic R group include asparatic acid and glutamic acid.

A "polymer" refers to a linear chain of two or more identical or non-identical subunits joined by covalent bonds.

As used herein, "peptide" and "polypeptide" refer to any polymer made up of a chain of amino acid residues linked by peptide bonds, regardless of its size. Although "protein" is often used in reference to relatively large polypeptides, and "peptide" is often used in reference to small polypeptides, usage of these terms in the art overlaps and varies. Thus, for simplicity, the term "peptide" will be used herein, although in some cases the art may refer to the same polymer as a "polypeptide." Unless otherwise indicated, the sequence for a peptide is given in the order from the amino terminus to the carboxyl terminus.

A "thiol-containing group" or "thiol-containing moiety" as used herein intends a functional group comprising a sulfur-hydrogen bond (—SH), and that is capable of reacting with another thiol under physiologic conditions to form a disulfide bond. A thiol that is capable of forming a disulfide bond with another thiol is referred to herein as a "reactive thiol." In a preferred embodiment the thiol-containing group is less than 6 atoms away from the backbone of the compound. In a more preferred embodiment, the thiol-containing group has the structure (—SH—CH$_2$—CH$_2$—C(O)—O—)—.

As used herein, "subject" refers to a human subject or an animal subject. Likewise, "patient" refers to a human patient or an animal patient.

A "subunit" intends a monomeric unit that is joined to more than one other monomeric unit to form a polymeric compound, where a subunit is the shortest repeating pattern of elements in the polymeric compound. Exemplary subunits are amino acids, which when linked form a polymer compound such as those referred to in the art as a peptide, a polypeptide or a protein.

As used herein, a "therapeutically effective amount" is an amount required to produce a desired therapeutic effect.

Unless otherwise specified, all documents referred to herein are incorporated by reference in their entirety.

II. Methods of Treatment

In one aspect, a method for treatment of hyperphosphatemia in a subject in need thereof is provided. In other aspects, methods of modulating, regulating, and/or reducing serum phosphorus levels in a dialysis patient are provided. In other aspects, methods of improving the treatment of patients receiving at least periodic dialysis are provided. In another aspect, a method is provided for reducing and/or attenuating phosphate rebound in the subject undergoing dialysis. These aspects and embodiments of the aspects will now be described.

As described in Example 1, a study was conducted in support of the methods of treatment described herein, wherein subjects with end stage renal disease (ESRD) receiving hemodialysis were treated with a calcimimetic agent. The patients in the study were diagnosed with secondary hyperparathyroidism (SHPT), and required regular hemodialysis sessions. The exemplary agent selected for the study was a calcium sensing receptor agonist compound of the formula described below, and having the sequence identified as SEQ ID NO:3. The compound was administered by intravenous injection immediately after hemodialysis at doses of 5, 10, 20, 40 or 60 mg to the patients after being randomized into treatment groups. For three days subsequent to treatment with the compound, blood concentrations of intact PTH and phosphorus were assessed. Results are shown in FIGS. 1-2.

Figure 2:
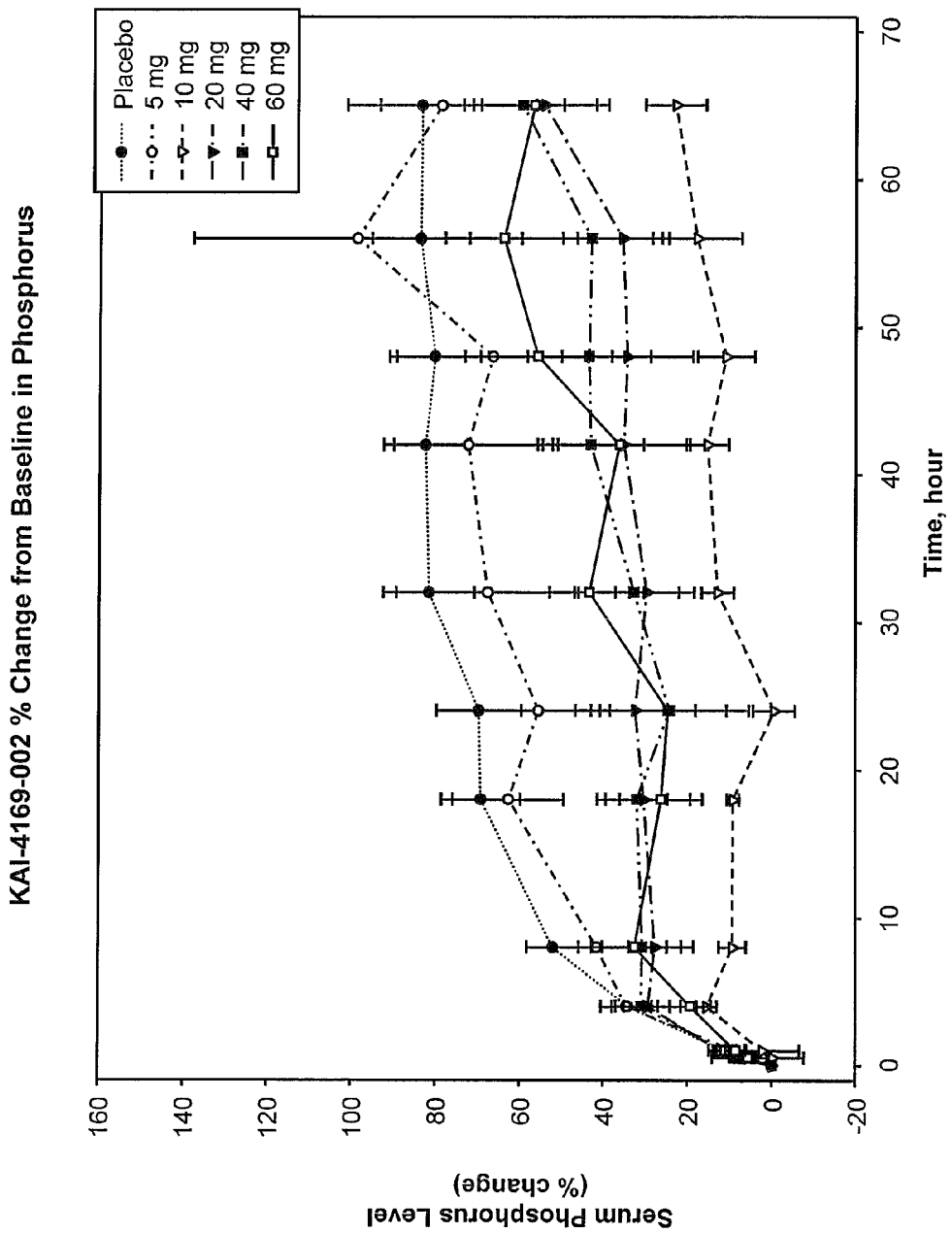
FIG. 2 is a graph showing the percent change in serum phosphorus levels during the interdialytic interval (i.e., shortly after hemodialysis and the subsequent ~72 hours until the next time the subject underwent hemodialysis) following administration of SEQ ID NO:3 or placebo by injection after dialysis. Placebo, closed circles; 5 mg SEQ ID NO:3, open circles; 10 mg SEQ ID NO:3, inverted open triangles; 20 mg SEQ ID NO:3, inverted closed triangles; 40 mg SEQ ID NO:3, closed squares; 60 mg SEQ ID NO:3, open squares.

As seen in FIG. 1, following injection of SEQ ID NO:3 post dialysis, there is a rapid 60-80% decrease in the levels of intact PTH in the blood followed by a dose dependant return towards baseline over the following 48 hours. There is an associated small (10-16%) decrease in serum calcium. As seen in FIG. 2, serum phosphorus levels, which were decreased by dialysis, rose rapidly over the first 8 hours to a plateau and then increased more slowly during the remaining interdialytic interval. In placebo subjects (closed circles), mean serum phosphorus increased rapidly during the first ~36 hours post-dose after which phosphorus levels tended to plateau at 84% above baseline levels at discharge. Surprisingly, the rate of return to the plateau level of phosphorus was markedly modified by administration of SEQ ID NO:3. Doses of the agonist compound greater than about 5 mg (open circles) provided a marked attenuation or decreased in the rise of serum phosphorus after dialysis. At discharge, the mean percent increase from baseline in serum phosphorus in subjects receiving 20-60 mg of the agonist identified by SEQ ID NO:3 ranged from 23% to 60% and was at least ~24 percentage points lower than placebo.

This data shows that after completion of a hemodialysis session, serum phosphorus concentration rises quickly in the first few hours. That is, serum phosphorus rebounds following hemodialysis and returns to the pre-dialysis value within the first ~10 hours after completion of dialysis, and reaches a plateau ~80% above the post-dialysis baseline levels approximately 18 hours after completion of dialysis. Table 1 sets forth the mean baseline pre-treatment values for PTH and phosphorus in ESRD subjects shortly (within 2 hours) following hemodialysis but prior to administration ("pre-dose") with SEQ ID NO:3 or placebo by intravenous injection. The serum phosphorus levels in the ESRD subjects receiving placebo increases (rebounds) most quickly during the first 3-10 hours after completion of dialysis. Without wishing to be bound by theory, it is thought that the 80-100% rebound in serum phosphorus following dialysis could result from mobilization of phosphate from intracellular space and/or from bone or possibly by stimulation of phosphate absorption from the digestive tract in response to and perhaps induced by the removal of phosphate by dialysis.

such that in the subsequent 18-72 hours of the post-dialytic period there was little to modest increase in serum phosphorus as measured by percent increase from post-dialysis baseline levels. Surprisingly, these data show that treatment of an ESRD patient with a CaSR agonist or a calcimimetic with the first 18 hours following dialysis dramatically attenuates or reduces the post-dialysis rebound in serum phosphorus concentration. These data reveal that much of the rebound in serum phosphorus occurs within the first 8-10 hours following dialysis and indicate, unexpectedly, that there is window during which administration of a CaSR agonist to an ESRD patient within the first 8-10 hours following dialysis can provide significant attenuation or blunting of the rebound of serum phosphorus.

Accordingly, in a first aspect, a patient receiving dialysis is treated with a CaSR agonist compound within about 5 minutes, 10 minutes, 15 minutes, 20 minutes, 30 minutes, 45 minutes, 1 hour, 2 hours, 3 hours, 4 hours after completion of the dialysis session, or about 3 hours, 2 hours, 1 hour, 45 minutes, 30 minutes, 20 minutes, 15 minutes, 10 minutes, 5 minutes before completion of the dialysis session. In a preferred embodimentn, the CaSR agonist compound is administered during the rinse back procedure at the end of dialysis. As a skilled artisan understands, dialysis intends hemodialysis or peritoneal dialysis. A hemodialysis session is typically between 3-5 hours in length, and reference to a "dialysis session" or a "hemodialysis session" herein is with regard to a dialysis procedure of a duration $T_D$, wherein $T_D$ can be 1 hour or more, 2 hours or more, 2.5 hours or more, 3 hours or more, 3.5 hours or more, 4 hours or more, 4.5 hours or more, 5 hours or more, or, in alternative embodiments from 1-10 hours, or 2-8 hours, or 2-6 hours, or 3-5 hours. $T_D$ can be separated into a first portion and a second portion, where the first portion corresponds to the first half of the total time duration $T_D$ and the second portion corresponds to the second half of the total time duration $T_D$. In one embodiment, the agonist compound is administered to the dialysis patient in the second portion of the dialysis session of duration $T_D$. In another embodiment, $T_D$ is separated into equal portions of three or four (thirds and quarters), and the agonist compound is administered to the dialysis patient in the latter third of the dialysis session of duration $T_D$ or in the last quarter of the dialysis session of duration $T_D$. For example, in a dialysis session with a $T_D$ of 3 hours, in one embodiment, the agonist is administered in the final hour of the dialysis session when $T_D$ is divided into thirds, or in the final 45 minutes of the dialysis session when $T_D$ is divided into fourths. In preferred

TABLE 1

| Mean (SD) | 5 mg (N = 4) | 10 mg (N = 4) | 20 mg (N = 4) | 40 mg (N = 8) | 60 mg (N = 8) |
| --- | --- | --- | --- | --- | --- |
| iPTH (pg/mL) | 450 (96) | 632 (255) | 1610 (1577) | 911 (935) | 821 (213) |
| Phosphorus (mg/dL) | 3.15 (0.26) | 3.28 (1.37) | 3.92 (0.66) | 3.02 (0.84) | 3.74 (0.65) |

It was found that if a CaSR agonist is administered to the patient within a certain time period in relation to the dialysis treatment, the phosphorus rebound can be reduced. As shown in FIG. 2, intravenous administration of a CaSR agonist (SEQ ID NO:3) at doses above 5 mg dramatically attenuated the post-dialysis rebound in serum phosphorus levels. Administration of a 10, 20, 40 or 60 mg dose of a CaSR agonist (e.g., SEQ ID NO:3) just before completion of or soon after dialysis displayed only a slight increase in phosphorus in the first 3-4 hours and dramatically attenuated or blunted the increase in serum phosphorus levels in the 4-18 hours following dialysis embodiments, the agonist is administered 30 minutes, 20 minutes, 15 minutes, 10 minutes, 5 minutes or 1 minute before completion of a dialysis session of duration $T_D$.

In other embodiments, the agonist is administered to the hemodialysis patient immediately upon completion of a dialysis session of duration $T_D$, or at least within 18 hours, within 15 hours, within 10 hours, within 8 hours, within 5 hours, within 3 hours, within 2 hours, within 1 hour, within 30 minutes, within 20 minutes, within 10 minutes or within 5 minutes after completion of a dialysis session having a time duration $T_D$. In one embodiment, the CaSR agonist is administered to the subject less than 2 hours, less than 3 hours, less than 4 hours, less than 5 hours, less than 6 hours, less than 7 hours, less than 8 hours, less than 9 hours, less than 10 hours, less than 18 hours, or less than 20 hours after completion of the hemodialysis. In another embodiment, the compound is administered to the subject 30-60 minutes, 1-2 hours, 2-3 hours, 3-5 hours, 5-8 hours, 8-10 hours, 10-15 hours, 15-18 hours after dialysis.

In a preferred embodiment, the CaSR agonist is administered at the end of dialysis or as soon as practical after dialysis. In some embodiments, the CaSR agonist is administered during dialysis, or less than 3 hours, less than 2 hours, less than 1 hour, or less than 30 minutes, before the end of dialysis.

Figure 3:
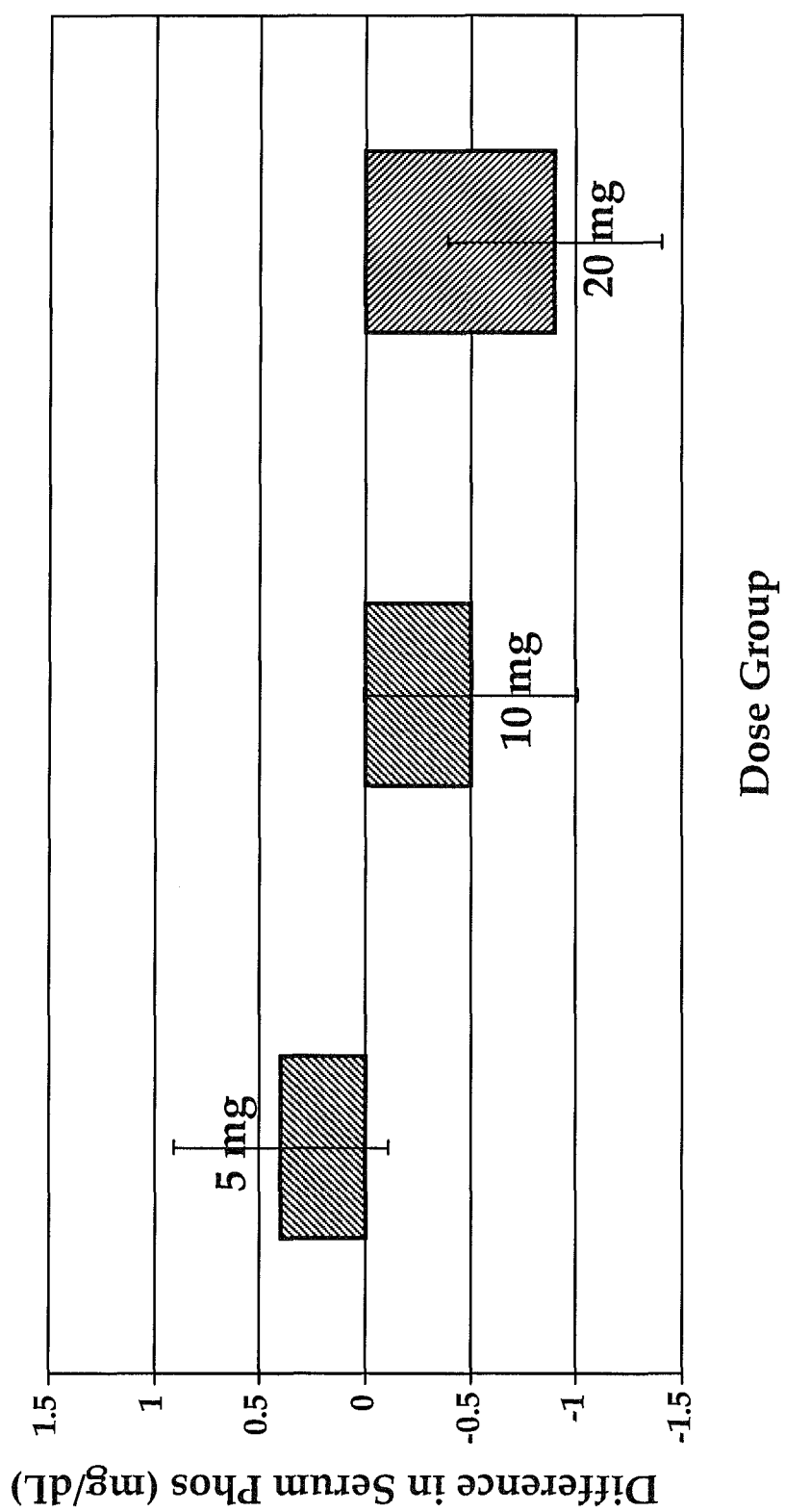
FIG. 3 is a graph showing the mean difference in serum phosphorus (mg/dL) (active v. placebo within cohort) for the 5 mg, 10 mg and 20 mg dose groups receiving SEQ ID NO: 3 (measured at discharge from the Phase 1 Unit).

As shown in FIG. 3, intravenous administration of a CaSR agonist (SEQ ID NO:3) at doses of 10 mg and 20 mg or above can dramatically attenuate the post-dialysis increase or rebound in serum phosphorus level and this can translate into a mean reduction in serum phosphate of 0.5 mg/dL to 1 mg/dL or more following a single dose. It is contemplated that these effects can be further enhanced with chronic dosing of a CaSR agonist wherein the treatment is administered with each dialysis session (which typically occurs three times per week with hemodialysis) and the treatment is consistently administered during or shortly following dialysis to attenuate or blunt the post-dialysis rebound in serum phosphorus.

In one embodiment, the patient's serum phosphorus increases by less than 10%, less than 20%, less than 30%, less than 40%, less than 50%, or less than 60% in the first hour after dialysis. In another embodiment, the patient's serum phosphorus increases by less than 10%, less than 20%, less than 30%, less than 40%, less than 50%, or less than 60% in the first 2 hours after dialysis. In one embodiment, the patient's serum phosphorus increases by less than 10%, less than 20%, less than 30%, less than 40%, less than 50%, or less than 60% in the first 3 hours after dialysis. In another embodiment, the patient's serum phosphorus increases by less than 10%, less than 20%, less than 30%, less than 40%, less than 50%, or less than 60% in the first 4 hours after dialysis. In another embodiment, the patient's serum phosphorus increases by less than 10%, less than 20%, less than 30%, less than 40%, less than 50%, or less than 60% in the first 5 hours after dialysis. In another embodiment, the patient's serum phosphorus increases by less than 10%, less than 20%, less than 30%, less than 40%, less than 50%, or less than 60% in the first 6 hours after dialysis. In another embodiment, the patient's serum phosphorus increases by less than 10%, less than 20%, less than 30%, less than 40%, less than 50%, or less than 60% in the first 7 hours after dialysis.

In one embodiment, the patient has undergone or is undergoing hemodialysis and the patient's serum phosphorus increases by less than 10%, less than 20%, less than 30%, less than 40%, less than 50%, or less than 60% in the first 3 hours or 6 hours after administration of the CaSR agonist. In another embodiment, the patient has undergone or is undergoing hemodialysis and the patient's serum phosphorus increases by less than 10%, less than 20%, less than 30%, less than 40%, less than 50%, or less than 60% in the first 4 hours or 6 hours after administration of the CaSR agonist. In another embodiment, the patient has undergone or is undergoing hemodialysis and the patient's serum phosphorus increases by less than 10%, less than 20%, less than 30%, less than 40%, less than 50%, or less than 60% in the first 5 hours after administration of the CaSR agonist. In another embodiment, the patient has undergone or is undergoing hemodialysis and the patient's serum phosphorus increases by less than 10%, less than 20%, less than 30%, less than 40%, less than 50%, or less than 60% in the first 6 hours after administration of the CaSR agonist. In another embodiment, the patient has undergone or is undergoing hemodialysis and the patient's serum phosphorus increases by less than 10%, less than 20%, less than 30%, less than 40%, less than 50%, or less than 60% in the first 7 hours after administration of the CaSR agonist.

In one embodiment, the dose of CaSR agonist administered to the patient is about 10 mg to about 20 mg, about 10 mg to about 30 mg, about 20 mg to about 30 mg, about 20 mg to about 40 mg, about 30 mg to about 50 mg, about 40 mg to about 60 mg, or about 50 mg to about 80 mg. In another embodiment, the dose of the CaSR agonist administered to the patient is about 10 mg, about 20 mg, about 30 mg, about 40 mg, about 50 mg, about 60 mg, about 70 mg, or about 80 mg.

In one embodiment, the dose of CaSR agonist administered to the patient is between 10-20 mg, 10-30 mg, 20-30 mg, 20-40 mg, 30-50 mg, or 40-60 mg. In another embodiment, the dose of the CaSR agonist administered to the hemodialysis patient is less than 10 mg, less than 20 mg, less than 30 mg, less than 40 mg, less than 50 mg, less than 60 mg, less than 70 mg, or less than 80 mg.

In one embodiment, the patient is being treated with a phosphate binding agent. However, in another embodiment, the patient is not being treated with a phosphate binding agent.

In one embodiment, conventional hemodialysis treatment alone is insufficient to control the patient's serum phosphorus levels.

In one embodiment, conventional hemodialysis treatment combined with administration of phosphate binders is insufficient to control the patient's serum phosphorus levels.

In one embodiment, conventional hemodialysis treatment combined with dietary restrictions is insufficient to control the patient's serum phosphorus levels.

In one embodiment, conventional hemodialysis treatment combined with phosphate binders and dietary restrictions is insufficient to control the patient's serum phosphorus levels.

In one embodiment, the patient is also taking vitamin D or a vitamin D analog.

Other causes of hyperphosphatemia include increased exogenous phosphorus load or absorption resulting from phosphorus-rich cow's milk in premature neonates, intravenous phosphorus supplements, white phosphorus burns, $PO_4^{3-}$-containing enemas or acute phosphorus poisoning. Hyperphosphatemia may result from increased endogenous loads due to tumor lysis syndrome, rhabdomyolysis, bowel infarction, malignant hyperthermia, heat stroke, acid-base disorders, organic acidosis, lactic acidosis, ketoacidosis, respiratory acidosis, or chronic respiratory alkalosis. Hyperphosphatemia may be caused by reduced urinary excretion resulting from renal failure, hypoparathyroidism, pseudohypoparathyroidism, Vitamin D intoxication, growth hormone, insulin-like growth factor-1, glucocorticoid withdrawal, $Mg^{2+}$ deficiency, tumoral calcinosis, diphosphonate therapy or hypophosphatasia. It is understood that methods of administration disclosed herein may be useful for treatment of subjects diagnosed with hyperphosphatemia resulting from any one or more of the above causes.

Methods for treatment as disclosed herein are useful to treat a variety of patient populations. For example, a method is provided for treating hemodialysis patients with concomitant hyperphosphatemia, for treating patients for whom conventional hemodialysis treatment alone is insufficient to control serum phosphate levels. In an alternative aspect, a method is provided for treating hemodialysis patients who are on a phosphorus restricted diet. Also provided is a method for treating hemodialysis patients who are being administered phosphate binders and/or who are taking vitamin D and experiencing a concomitant increase in serum phosphorus.

In any of the aspects or embodiments described herein, any one or more of the CaSR agonists is contemplated to be individually excepted or removed from the scope of compounds disclosed herein to be administered. In certain embodiments, the peptides identified by any one or more of SEQ ID NOs: 162-182, individually or in any combination, are excluded from the claimed methods.

For example, in one aspect, a method for treating a dialysis patient with, for example, SHPT or CKD or ESRD, is provided, wherein a CaSR agonist is administered within about 18 hours after conclusion of dialysis (preferably hemodialysis), or within about 6 hours, 4 hours, 3, hours, 2 hours, 1 hour, 30 minutes, 20 minutes, 10 minutes, or 9, 8, 7, 6, 5, 4, 3, 2, or 1 minute after conclusion of dialysis (preferably hemodialysis). Administration of the CaSR in this fashion is effective to maintain a post-dialysis serum phosphorus level that is lower than a pre-dialysis serum phosphorus level for a period of at least 6 hours, more preferably for a period of 24 hours, still more preferably for a period of 36, 48, 60 or 72 hours. In one embodiment, the post-dialysis serum phosphorus level remains lower than a pre-dialysis serum phosphorus level of the patient for the duration of the between dialysis sessions (also referred to as an interdialytic period). In one embodiment of this method, the CaSR agonist is not a compound of the form $X_1$—$X_2$—$X_3$-$X_4$—$X_5$—$X_6$—$X_7$, wherein the X subunits are as defined herein.

In another aspect, a method for treating hyperphosphatemia in a subject that receives dialysis is provided, wherein the subject is treated with a CaSR agonist compound as described herein. The treatment is effective to provide a post-dialysis serum phosphorus level that is less than a pre-dialysis serum phosphorus level for the duration of the interdialytic period. In one embodiment, the post-dialysis serum phosphorus level is at least about 10% or 25% less than a pre-dialysis serum phosphorus level for the duration of the interdialytic period. The CaSR agonist compound is administered in accord with any of the treatment embodiments described herein, for example, before completion of a dialysis session or within about 2, 4, 6, 10, or 18 hours after a dialysis session.

III. Calcium Sensing Receptor Agonist Compounds and Compositions

The methods described herein comprise administration of a CaSR agonist to a subject. Such agonists are described in U.S. Pat. Nos. 6,011,068 and 6,031,003 and U.S. Patent Publication Nos. 2011/0028394 and 2009/0023652 (incorporated herein by reference in their entirety).

It has been unexpectedly found that administration of these compounds to subjects suffering from CKD and in need of dialysis results in an inhibition or reduction of the accumulation of serum phosphorus after dialysis.

In one embodiment, the method comprises administering a CaSR agonist to the patient. In one embodiment, the CaSR agonist is a calcimimetic. In another embodiment, the CaSR agonist is an allosteric agonist. In another embodiment, the CaSR agonist is cinacalcet hydrochloride. In another embodiment, the CaSR agonist is a compound comprising the formula:

$$X_1\text{—}X_2\text{—}X_3\text{—}X_4\text{—}X_5\text{—}X_6\text{—}X_7$$

wherein $X_1$ is a subunit comprising a thiol-containing group; $X_5$ is a cationic subunit; $X_6$ is a non-cationic subunit; $X_7$ is a cationic a subunit; and at least two of $X_2$, $X_3$ and $X_4$ are independently a cationic subunit.

In one embodiment, the CaSR agonist is a compound comprising the sequence carrrar (SEQ ID NO:2). In another embodiment, the CaSR agonist is a conjugate comprised of the peptide carrrar (SEQ ID NO:2), where the peptide is conjugated at its N-terminal residue to a Cys residue. In a preferred embodiment, the conjugate is Ac-c(C)arrrar-NH$_2$ (SEQ ID NO:3). Although the invention may be described in terms of certain preferred embodiments, such as SEQ ID NO:3, it will be within the understanding of one of skill in the art that the disclosure also applies to other CaSR agonists, including the compounds and conjugates described in U.S. Pat. Nos. 6,011,068 and 6,031,003 and U.S. Patent Publication Nos. 2011/0028394 and 2009/0023652 (incorporated herein by reference in their entirety). Likewise, although the invention may be described in terms of certain preferred embodiments, such as hemodialysis, it will be within the understanding of one of skill in the art that the disclosure also applies to other forms of dialysis, such as peritoneal dialysis, and other approaches, such as quotidian hemodialysis.

In one embodiment, the CaSR agonist is administered as a composition of the CaSR agonist compound and a pharmaceutically acceptable excipient. The excipient in some embodiments is a buffer or saline, such that the composition is in solution form when administered to the patient. In one embodiment, the agonist compound is provided as a lyophilized product that is reconstituted into a solution or suspension for administration in accord with the methods described herein. In one embodiment, the lyophilized product is a salt form of the agonist product, such as cinacalet hydrochloride or a hydrochloride salt form of a peptide of the form SEQ ID NO:3.

Peptide Compounds and Structure-Activity Relationships

Several compounds were synthesized for testing their effects on decreasing serum phosphorus and on hyperphosphatemia. These compounds are listed in Table 2 below. In Table 1, and throughout the specification, residues provided in capital letters are L-amino acids, while lower case letters indicate D-amino acids. "Ac" indicates an acetyl capping group, "NH$_2$" indicates an amide capping group, "Ac-bAla" is an acetylated beta-alanine, "GSH" indicates reduced glutathione, "GS" indicates oxidized glutathione, "PEG" refers to polyethylene glycol, "PEG2" and "PEG5" refer to polyethylene glycol moieties of 2 kDa and 5 kDa, respectively, and "Mpa" refers to mercaptopropionic acid. A group bracketed by parentheses indicates that group or moiety is attached to the side-chain of the preceding subunit or amino acid residue.

TABLE 2

| SEQ ID NO. | Compound Structure |
|---|---|
| SEQ ID NO: 1 | XXXXXXX |
| SEQ ID NO: 2 | carrrar |
| SEQ ID NO: 3 | Ac-c(C)arrrar-NH$_2$ |
| SEQ ID NO: 4 | Ac-crrrr-NH$_2$ |
| SEQ ID NO: 5 | Ac-crrrrr-NH$_2$ |
| SEQ ID NO: 6 | Ac-crrrrrr-NH$_2$ |
| SEQ ID NO: 7 | Ac-crrrrrrr-NH$_2$ |
| SEQ ID NO: 8 | Ac-carrrrr-NH$_2$ |

TABLE 2-continued

| SEQ ID NO. | Compound Structure |
|---|---|
| SEQ ID NO: 9 | Ac-crarrrr-NH$_2$ |
| SEQ ID NO: 10 | Ac-crrarrr-NH$_2$ |
| SEQ ID NO: 11 | Ac-crrrarr-NH$_2$ |
| SEQ ID NO: 12 | Ac-crrrrar-NH$_2$ |
| SEQ ID NO: 13 | Ac-crrrrra-NH$_2$ |
| SEQ ID NO: 14 | Ac-crrarra-NH$_2$ |
| SEQ ID NO: 15 | Ac-cararrr-NH$_2$ |
| SEQ ID NO: 16 | Ac-carrarr-NH$_2$ |
| SEQ ID NO: 17 | Ac-crraarr-NH$_2$ |
| SEQ ID NO: 18 | Ac-crararr-NH$_2$ |
| SEQ ID NO: 19 | Ac-carrrra-NH$_2$ |
| SEQ ID NO: 20 | Ac-crarrra-NH$_2$ |
| SEQ ID NO: 21 | Ac-crrraar-NH$_2$ |
| SEQ ID NO: 22 | Ac-caarrrr-NH$_2$ |
| SEQ ID NO: 23 | Ac-crarrar-NH$_2$ |
| SEQ ID NO: 24 | Ac-craarrr-NH$_2$ |
| SEQ ID NO: 25 | Ac-crrarar-NH$_2$ |
| SEQ ID NO: 26 | Ac-carrrar-NH$_2$ |
| SEQ ID NO: 27 | Ac-c(C)arrrar-NH$_2$ |
| SEQ ID NO: 28 | Ac-c(C)rrarar-NH$_2$ |
| SEQ ID NO: 29 | Ac-arrrar-NH$_2$ |
| SEQ ID NO: 30 | Ac-bAla-crrrrrr-NH$_2$ |
| SEQ ID NO: 31 | Mpa-rrrrrr-NH$_2$ |
| SEQ ID NO: 32 | Ac-dHcy-rrrrrr-NH$_2$ |
| SEQ ID NO: 33 | Ac-dPen-rrrrrr-NH$_2$ |
| SEQ ID NO: 34 | Ac-C(C)arrrar-NH$_2$ |
| SEQ ID NO: 35 | Ac-c(C)Arrrar-NH$_2$ |
| SEQ ID NO: 36 | Ac-c(C)aRrrar-NH$_2$ |
| SEQ ID NO: 37 | Ac-c(C)arRrar-NH$_2$ |
| SEQ ID NO: 38 | Ac-c(C)arrRar-NH$_2$ |
| SEQ ID NO: 39 | Ac-c(C)arrrAr-NH$_2$ |
| SEQ ID NO: 40 | Ac-c(C)arrraR-NH$_2$ |
| SEQ ID NO: 41 | Ac-crrrrrrrr-NH$_2$ |
| SEQ ID NO: 42 | Ac-cGrrrGr-NH$_2$ |
| SEQ ID NO: 43 | Ac-cArrrAr-NH$_2$ |
| SEQ ID NO: 44 | Ac-CaRrRaR-NH$_2$ |
| SEQ ID NO: 45 | CHDAPIGYD |
| SEQ ID NO: 46 | CPDYHDAGI |
| SEQ ID NO: 47 | Ac-CYGRKKRRQRRR-NH$_2$ |
| (SEQ ID NO: 45)<br>(SEQ ID NO: 47) | CHDAPIGYD<br>\|<br>Ac-CYGRKKRRQRRR-NH$_2$ |
| SEQ ID NO: 46<br>SEQ ID NO: 47 | CPDYHDAGI<br>\|<br>Ac-CYGRKKRRQRRR-NH$_2$ |
| SEQ ID NO: 48 | Ac-YGRKKRRQRRR-NH$_2$ |
| SEQ ID NO: 49 | Ac-caraarrr-NH$_2$ |
| SEQ ID NO: 50 | Ac-cygrkkrrqrrr-NH$_2$ |
| SEQ ID NO: 51 | H$_2$N-crrrrrr-NH$_2$ |
| SEQ ID NO: 51 | H$_2$N-crrrrrr-NH$_2$<br>\| |
| SEQ ID NO: 51 | H$_2$N-crrrrrr-NH$_2$ |
| SEQ ID NO: 52 | Ac-carrrar-NH$_2$ |
| SEQ ID NO: 52 | Ac-carrrar-NH$_2$<br>\| |
| SEQ ID NO: 52 | Ac-carrrar-NH$_2$ |
| SEQ ID NO: 53 | Ac-c(GS)rrrrrr-NH$_2$ |
| SEQ ID NO: 54 | GS-crrrrrr |
| SEQ ID NO: 55 | Ac-c(Ac-C)arrrar-NH$_2$ |
| SEQ ID NO: 56 | Ac-c(Mpa)arrrar-NH$_2$ |
| SEQ ID NO: 57 | Ac-c(PEG2-C)arrrar-NH$_2$ |
| SEQ ID NO: 58 | Ac-c(PEG5-C)rrrrrr-NH$_2$ |
| SEQ ID NO: 59 | Ac-c(PEG2-C)rrrrrr-NH$_2$ |
| SEQ ID NO: 60 | c(C)arrrar-NH$_2$ |
| SEQ ID NO: 61 | Ac-bAla-c(C)arrrar-NH$_2$ |
| SEQ ID NO: 62 | bAla-c(C)arrrar |
| SEQ ID NO: 63 | Ac-cGrrrGr |
| SEQ ID NO: 64 | Ac-cArrrAr |
| SEQ ID NO: 65 | Ac-cvrrrvr-NH$_2$ |
| SEQ ID NO: 66 | Ac-cvrrrvr |
| SEQ ID NO: 67 | Ac-Crrrrrr-NH$_2$ |
| SEQ ID NO: 68 | Ac-carrrer-NH$_2$ |
| SEQ ID NO: 69 | Ac-cerrrar-NH$_2$ |
| SEQ ID NO: 70 | Ac-carrrak-NH$_2$ |
| SEQ ID NO: 71 | Ac-qrrrar-NH$_2$ |
| SEQ ID NO: 72 | Ac-cakrrar-NH$_2$ |
| SEQ ID NO: 73 | Ac-carkrar-NH$_2$ |
| SEQ ID NO: 74 | Ac-carrrar-OH |
| SEQ ID NO: 75 | Ac-CARRRAR-NH$_2$ |
| SEQ ID NO: 76 | Ac-caarrrrr-NH$_2$ |
| SEQ ID NO: 77 | Ac-caaarrrrr-NH$_2$ |

TABLE 2-continued

| SEQ ID NO. | Compound Structure |
|---|---|
| SEQ ID NO: 78 | Ac-carararar-NH$_2$ |
| SEQ ID NO: 79 | Ac-carrrarar-NH$_2$ |
| SEQ ID NO: 80 | crrrrrr-NH$_2$ |
| SEQ ID NO: 32 | Ac-dHcy rrrrrr-NH$_2$ |
| SEQ ID NO: 81 | Ac-c(Benzoyl)rrrrrr-NH$_2$ |
| SEQ ID NO: 82 | Ac-c(acetyl)rrrrrr-NH$_2$ |
| SEQ ID NO: 83 | Ac-carrrfr-NH$_2$ |
| SEQ ID NO: 84 | Ac-carrrir-NH$_2$ |
| SEQ ID NO: 85 | Ac-carrrlr-NH$_2$ |
| SEQ ID NO: 68 | Ac-carrrer-NH$_2$ |
| SEQ ID NO: 87 | Ac-carrrvr-NH$_2$ |
| SEQ ID NO: 88 | Ac-carrrpr-NH$_2$ |
| SEQ ID NO: 89 | Ac-carrrhr-NH$_2$ |
| SEQ ID NO: 90 | Ac-carrrqr-NH$_2$ |
| SEQ ID NO: 91 | Ac-carrrtr-NH$_2$ |
| SEQ ID NO: 92 | Ac-carrrsr-NH$_2$ |
| SEQ ID NO: 93 | Ac-carrrGr-NH$_2$ |
| SEQ ID NO: 94 | Ac-cerrrar-NH$_2$ |
| SEQ ID NO: 95 | Ac-cGrrrar-NH$_2$ |
| SEQ ID NO: 96 | Ac-cirrrar-NH$_2$ |
| SEQ ID NO: 97 | Ac-cprrrar-NH$_2$ |
| SEQ ID NO: 98 | Ac-clrrrar-NH$_2$ |
| SEQ ID NO: 99 | Ac-cqrrrar-NH$_2$ |
| SEQ ID NO: 100 | Ac-ctrrrar-NH$_2$ |
| SEQ ID NO: 101 | Ac-cvrrrar-NH$_2$ |
| SEQ ID NO: 102 | Ac-csrrrar-NH$_2$ |
| SEQ ID NO: 103 | Ac-chrrrar-NH$_2$ |
| SEQ ID NO: 104 | Ac-cfrrrar-NH$_2$ |
| SEQ ID NO: 105 | Ac-crrGrar-NH$_2$ |
| SEQ ID NO: 106 | Ac-crrprar-NH$_2$ |
| SEQ ID NO: 107 | Ac-crrerar-NH$_2$ |
| SEQ ID NO: 108 | Ac-crrtrar-NH$_2$ |
| SEQ ID NO: 109 | Ac-crrhrar-NH$_2$ |
| SEQ ID NO: 110 | Ac-crrfrar-NH$_2$ |
| SEQ ID NO: 111 | Ac-crrsrar-NH$_2$ |
| SEQ ID NO: 112 | Ac-crrqrar-NH$_2$ |
| SEQ ID NO: 113 | Ac-crrvrar-NH$_2$ |
| SEQ ID NO: 114 | Ac-crrlrar-NH$_2$ |
| SEQ ID NO: 115 | Ac-crrirar-NH$_2$ |
| SEQ ID NO: 116 | Ac-crr-Sar-rar-NH$_2$ |
| SEQ ID NO: 117 | Ac-carrr-Sar-r-NH$_2$ |
| SEQ ID NO: 118 | Ac-c-Nma-rrr-Nma-r-NH$_2$ |
| SEQ ID NO: 119 | Ac-crrar-Nma-r-NH$_2$ |
| SEQ ID NO: 120 | Ac-c-Aib-rrr-Aib-r-NH$_2$ |
| SEQ ID NO: 121 | Ac-crr-Nma-rar-NH$_2$ |
| SEQ ID NO: 122 | Ac-carrr-Nma-r-NH$_2$ |
| SEQ ID NO: 123 | Ac-c-Aib-rrrar-NH$_2$ |
| SEQ ID NO: 124 | Ac-carrr-Aib-r-NH$_2$ |
| SEQ ID NO: 125 | Ac-c-Sar-rrr-Sar-r-NH$_2$ |
| SEQ ID NO: 126 | Ac-crrar-Sar-r-NH$_2$ |
| SEQ ID NO: 127 | Ac-c-Nma-rrrar-NH$_2$ |
| SEQ ID NO: 128 | Ac-c-Sar-rrrar-NH$_2$ |
| SEQ ID NO: 129 | Ac-carrr-Nle-r-NH$_2$ |
| SEQ ID NO: 130 | Ac-c-dNle-rrr-dNle-r-NH$_2$ |
| SEQ ID NO: 131 | Ac-carrr-dNva-r-NH$_2$ |
| SEQ ID NO: 132 | Ac-c-dNva-rrr-dNva-r-NH$_2$ |
| SEQ ID NO: 133 | Ac-crrar-dNle-r-NH$_2$ |
| SEQ ID NO: 134 | Ac-c-dNle-rrrar-NH$_2$ |
| SEQ ID NO: 135 | Ac-crrar-dNva-r-NH$_2$ |
| SEQ ID NO: 136 | Ac-c-dNva-rrrar-NH$_2$ |
| SEQ ID NO: 137 | Ac-crr-dNva-rar-NH$_2$ |
| SEQ ID NO: 138 | Ac-crr-dNle-rar-NH$_2$ |
| SEQ ID NO: 139 | Ac-c(dHcy)arrrar-NH$_2$ |
| SEQ ID NO: 140 | Ac-c(Mpa)arrrar-NH$_2$ |
| SEQ ID NO: 141 | Ac-c(Ac-C)arrrar-NH$_2$ |
| SEQ ID NO: 142 | Ac-c(c)arrrar-NH$_2$ |
| SEQ ID NO: 143*** | Ac-c(C-PEG20)rrrrrr-NH$_2$ |
| SEQ ID NO: 144**** | Ac-c(C-PEG40)rrrrrr-NH$_2$ |
| SEQ ID NO: 145 | CEEEEEE |
| SEQ ID NO: 145 | CEEEEEE |
| SEQ ID NO: 6 | Ac-crrrrrr-NH$_2$ |
| SEQ ID NO: 145 | CEEEEEE |
| SEQ ID NO: 26 | Ac-carrrar-NH$_2$ |
| SEQ ID NO: 25 | Ac-crrarar-NH$_2$ |
| SEQ ID NO: 25 | Ac-crrarar-NH$_2$ |
| SEQ ID NO: 26 | Ac-carrrar-NH$_2$ |
| SEQ ID NO: 26 | Ac-carrrar-NH$_2$ |
| SEQ ID NO: 146 | Ac-crrrraa-NH$_2$ |

TABLE 2-continued

| SEQ ID NO. | Compound Structure |
|---|---|
| SEQ ID NO: 147 | Ac-cakkkak-NH$_2$ |
| SEQ ID NO: 148 | Ac-cararar-NH$_2$ |
| SEQ ID NO: 149 | Ac-crrarGr-NH$_2$ |
| SEQ ID NO: 150 | Ac-crrarqr-NH$_2$ |
| SQ ID NO: 151 | Ac-crrarhr-NH$_2$ |
| SEQ ID NO: 152 | Ac-crrarir-NH$_2$ |
| SEQ ID NO: 153 | Ac-ca(DAP)rrar-NH$_2$ |
| SEQ ID NO: 154 | Ac-ca(dHar)(dHar)(dHar)ar-NH$_2$ |
| SEQ ID NO: 162 | HDAPIGYD |
| SEQ ID NO: 163 | CHDAPIGYD |
| SEQ ID NO: 164 | YGRKKRRQRRR |
| SEQ ID NO: 165 | CYGRKKRRQRRR |
| SEQ ID NO: 166 | CSFNSYELGSL |
| SEQ ID NO: 167 | CPDYHDAGI |
| SEQ ID NO: 168 | CEAVSLKPT |
| SEQ ID NO: 169 | ESVSLKPT |
| SEQ ID NO: 170 | CRFARKGALRQKNV |
| SEQ ID NO: 171 | YGRKKR |
| SEQ ID NO: 172 | CYGRKKR |
| SEQ ID NO: 173 | YGRRARRRARR |
| SEQ ID NO: 174 | CYGRRARRRARR |
| SEQ ID NO: 175 | CRRR |
| SEQ ID NO: 176 | CRRRR |
| SEQ ID NO: 177 | CRRRRRRR |
| SEQ ID NO: 178 | CRRRRRRRR |
| SEQ ID NO: 179 | CRRRRRRRRR |
| SEQ ID NO: 180 | CRRRRRRRRRR |
| SEQ ID NO: 181 | CRRRRRRRRRRR |
| SEQ ID NO: 182 | CRRRRRRRRRRRR |

*Bolded font showing in parenthesis indicates respective thiol-containing conjugating groups. GS = oxidized glutathione; dHcy = D-homocysteine; Mpa = Mercaptopropionic acid; PEG = polyethylene glycol.

These compounds include (i) Ac-crrrr-NH$_2$ (SEQ ID NO:4), (ii) Ac-crrrrr-NH$_2$ (SEQ ID NO:5), (iii) Ac-crrrrrr-NH$_2$ (SEQ ID NO:6), and (iv) Ac-crrrrrrr-NH$_2$ (SEQ ID NO:7). In previous studies, the compounds identified as SEQ ID NO:4, SEQ ID NO:5, SEQ ID NO:6 and SEQ ID NO:7 were each administered by a 30-minute IV infusion to 1K1C model animals and effected a reduction in plasma PTH levels as a percent of the pre-dosing (baseline) level. All four compounds dosed at 3 mg/kg produced a significant drop in plasma PTH, but differences in the potency and duration of PTH reduction suggest a relationship between the net positive charge and PTH-lowering activity. For example, the compound Ac-crrrrrr-NH$_2$ (SEQ ID NO:6) with six cationic (arginine) subunits had increased efficacy as well as the duration of action compared to the compounds Ac-crrrr-NH$_2$ (SEQ ID NO:4) and Ac-crrrrr-NH$_2$ (SEQ ID NO:5), containing four and five cationic (arginine) subunits, respectively. Surprisingly, the compound Ac-crrrrrr-NH$_2$ (SEQ ID NO:6) with six cationic (arginine) subunits had increased duration of action compared to the compound Ac-crrrrrrr-NH$_2$ (SEQ ID NO:7) with seven cationic (arginine) residues, suggesting that activity or potency of the compounds does not correlate merely with increasing cationic charge of the compound. That is, the compound Ac-crrrrrrr-NH$_2$ (SEQ ID NO:7) with seven cationic subunits (arginine residues) produced a similar initial drop in PTH as the compounds with fewer cationic residues, but over the 24 hours following dosing was less efficacious than Ac-crrrrrr-NH$_2$ (SEQ ID NO:6) and Ac-crrrrr-NH$_2$ (SEQ ID NO:5). These latter two compounds produced a mean PTH reduction of ~40% and 60% at the 24 hour time point, respectively. It should be noted that the compounds in this study were administered at the same mg/kg dose but, due to differences in molecular weight, a different number of moles of each compound was actually dosed. Therefore, Ac-crrrrrr-NH$_2$ (SEQ ID NO:6) was significantly more potent than Ac-crrrr-NH$_2$ (SEQ ID NO:4) and Ac-crrrrr-NH$_2$ (SEQ ID NO:5) on a per mole basis.

Further studies were done to explore the structure-activity relationship of the compounds. The compound Ac-crrrrrr-NH$_2$ (SEQ ID NO:6) was modified by sequential replacement of an arginine residue with an alanine residue at each of the subunit positions $X_2$-$X_7$. The compounds were characterized in an in vitro human calcium-sensing receptor (CaSR) assay, wherein HEK 293 cells that express the human calcium-sensing receptor were used to measure activity of exemplary compounds.

The compounds Ac-crrrrrr-NH$_2$ (SEQ ID NO:6), Ac-carrrrr-NH$_2$ (SEQ ID NO:8) and Ac-crrarrr-NH$_2$ (SEQ ID NO:10) were quite potent, as evidenced by the decrease in percent PTH to below the detection limit or essentially zero as measured in vivo after a single IV administration in normal rats. Substitution of the cationic (arginine) residue at positions 2, 3, 4 or 7 of Ac-crrrrrr-NH$_2$ (SEQ ID NO:6) resulted in an approximately two-fold loss in in vitro potency. The substitution at position 5 to produce the compound Ac-crrrarr-NH$_2$ (SEQ ID NO:11) produced a 5-10 fold reduction in in vitro potency, although the in vivo percent PTH AUC reduction of 45% could be sufficiently active for clinical therapy. Surprisingly, the substitution of the cationic arginine residue at position 6 with the uncharged (alanine) residue actually improved potency. The data illustrate that cationic and uncharged residues at different positions are not all equal and there are changes in activity as a result of change in the compound structure.

To further evaluate the effect of change in activity as a function of change in compound structure, another series of analogs of Ac-crrrrrr-NH$_2$ (SEQ ID NO:6) was generated containing double amino acid substitutions, where two cationic (arginine) residues were replaced by uncharged (alanine) residues, and tested for potency. Unexpectedly, this suggests that position of charges as well as total cationic charge can influence potency of the compounds for reduction of PTH. The data suggest that the cationic residues of SEQ ID NO:6 are essential at positions 5 and 7 but is not required at position 6, for PTH-lowering activity.

Further structure-activity relationship studies were conducted using the in vitro cell assay in HEK 293 cells that express the human calcium-sensing receptor. The ability of the peptides Ac-carrrar-NH$_2$ (SEQ ID NO:26) and Ac-arrrar- NH$_2$ (SEQ ID NO:29) to activate the human CaSR was ascertained by the measuring accumulation of inositol monophosphate (IP$_1$), which is reflective of IP$_3$ production. Absence of the N-terminal D-cysteine residue from SEQ ID NO:29 dramatically reduced the ability of the compound to activate the CaSR as compared to SEQ ID NO:26. That is, elimination of the N-terminal cysteine residue significantly reduced the potency of the compound, as the peptides Ac-carrrar-NH (SEQ ID NO:26) and Ac-arrrar-NH$_2$ (SEQ ID NO:29) differ only by the presence or absence of the N-terminal D-cysteine.

The contribution of the thiol-containing group in the X$_1$ subunit of the compound (e.g., in certain embodiments where the compound is a peptide on the N-terminal residue), was also investigated in an in vivo study. The PTH-lowering activity of the peptides identified as SEQ ID NO:26 (Ac-carrrar-NH$_2$) and as SEQ ID NO:29 (Ac-arrrar-NH$_2$) was evaluated in vivo. A 0.5 mg/kg dose of the peptide Ac-carrrar-NH$_2$ (SEQ ID NO:26) decreased PTH blood concentration to a non-detectable level for up to 4 hours after dosing. In contrast, the peptide lacking an N-terminal residue with a thiol-containing group, Ac-arrrar-NH$_2$ (SEQ ID NO:29), did not reduce PTH concentration, even at a substantially higher dose (i.e., 9 mg/kg).

The structure-activity relationship of the thiol-containing group in the X$_1$ subunit of the compound was further analyzed by preparing compounds with differing X$_1$ subunits. The compounds, were tested in vivo in normal rats for activity to reduce PTH. The data illustrated that the thiol-containing X$_1$ subunit can be varied. Compounds with the following in the N-terminal residue were tested—D-cysteine (cys), D-penicillamine (dPen), d-homocysteine (dHcy) and mercaptopropionic acid (Mpa). In addition, a natural or non-natural amino acid, such as beta alanine, can be conjugated to the N-terminal thiol-containing residue. The data illustrated that cationic compounds such as Ac-crmmr-NH$_2$ (SEQ ID NO:6) containing different thiol-containing groups in the X$_1$ subunit effectively reduce PTH in vivo. Substituting the N-terminal cysteine residue with methionine, which does not contain a thiol group, resulted in a compound with very poor in vivo PTH-lowering activity.

Based on the studies described above, compounds of the contiguous sequence of subunits X$_1$—X$_2$—X$_3$—X$_4$—X$_5$—X$_6$—X$_7$, where X$_1$ is a subunit comprising a thiol-containing group, have activity to decrease parathyroid hormone levels. In one embodiment, the thiol-containing group on the X$_1$ subunit is selected from the group consisting of thiol-containing amino acid residues and organic thiol-containing moieties. In another embodiment, the thiol-containing group is capable of reacting with another thiol group under physiologic pH and temperature. In certain embodiments where the thiol-containing residue is an amino acid residue, the X$_1$ subunit can be any one of cysteine, glutathione, mercaptopropionic acid, n-acetylated cysteine and PEGylated cysteine. In embodiments where the thiol-containing group is on a non-amino acid residue subunit, such an organic small molecule with a thiol-containing group, the X$_1$ subunit can be a thiol-alkyl, or thioacyl moieties such as 3-mercaptopropyl or 3-mercaptopropionyl residues. In one embodiment, the thiol is not homocysteine.

Additional structure activity studies were conducted, to further evaluate the effect of properties of each subunit in the compound on its therapeutic activity. A series of compounds having an L-amino acid residue substituted for a D-amino acid residue were prepared based on the PTH-lowering scaffold Ac-c(C)arrrar-NH$_2$ (SEQ ID NO:3). The compounds were administered to subjects and plasma PTH levels were assessed prior to dosing and 1, 2, 3 and 4 hours after dosing.

The exemplary compounds shown in Table 1 may be chemically modified at both the N-terminus and the C-terminus, as indicated by the Ac and NH$_2$ designations. The sequence of seven subunits carrrar (SEQ ID NO:3), wherein all subunits were D-amino acid residues, was modified by replacing one subunit at a time with an L-amino acid. The X$_1$ subunit was a D-Cys residue (or L-Cys residue in SEQ ID NO:34) conjugated via a disulfide linkage to an L-Cys residue, as indicated by the parenthetical designation (C). Previous studies have shown that chirality of Arg and Ala affect activity of the compounds. In one embodiment, a compound of the sequence X$_1$—X$_2$—X$_3$—X$_4$—X$_5$—X$_6$—X$_7$ is contemplated, where at least the subunits identified as X$_4$ and X$_7$ are D-amino acid residue subunits. In another embodiment, the subunits identified as X$_4$, X$_5$, X$_6$ and X$_7$ are D-amino acid residue subunits. In a preferred embodiment, the subunits identified as X$_3$, X$_4$, X$_5$, X$_6$ and X$_7$ are D-amino acid residue subunits. In most preferred embodiments, the subunits identified as X$_2$, X$_3$, X$_4$, X$_5$, X$_6$ and X$_7$ are D-amino acid residue subunits, and all of the subunits X$_1$, X$_2$, X$_3$, X$_4$, X$_5$, X$_6$ and X$_7$ are D-amino acid residue subunits.

In other studies, it also was found that substitution of a peptide having all L-amino acids with all D-amino acids did not reduce the in vitro activity of the peptides tested; in fact, peptides composed entirely of D-amino acids appeared to enhance the potency for activation of the CaSR. It was also shown that some of the cationic (arginine) residues, at specific positions relative to the cysteine residue, could be substituted with uncharged (alanine) residues with minimal effect on the activity toward the CaSR.

To further characterize the relationship between structure and activity against the CaSR, a variety of cationic peptides with different numbers (4 to 8) of arginine residues (all of which contained an N-terminal cysteine) were tested using the HEK-293 in vitro cell assay. A direct correlation was found between the number of cationic subunits and the potency of the compound, where potency is evidenced by ability to activate the CaSR. Reducing the number of cationic (e.g., arginine) subunits from 5 to 4 resulted in the largest shift in potency (>10-fold) suggesting that there may be an activity inflection point between compounds having these net charges, that a cationic subunit at subunit X$_5$ is preferred for activity. Accordingly, the compounds of the structure X$_1$—X$_2$—X$_3$—X$_4$—X$_5$—X$_6$—X$_7$ are contemplated, wherein X$_5$ is a cationic subunit. In certain embodiments the X$_1$ is a subunit comprises a thiol group that is capable of reacting with another thiol group under physiologic conditions (a "reactive thiol", intending a thiol that reacts with another thiol (e.g., cysteine with cysteine) under physiologic conditions of pH 7.4 and body temperature).

Unexpectedly, Ac-crrrrrr-NH$_2$ (SEQ ID NO:6) with six cationic residues, when evaluated in vivo, exhibited greater and more prolonged activity than Ac-crrrrrrrr-NH$_2$ (SEQ ID NO:41), which has eight cationic residues. This is in contrast to the observation that SEQ ID NO:41 was more potent at activating the CaSR in this in vitro cell assay. Without wishing to be bound by theory, it is thought that the superior performance of Ac-crrrrrr-NH$_2$ (SEQ ID NO:6) in vivo may stem from better pharmacokinetic properties of Ac-crrrrrr-NH$_2$ (SEQ ID NO:6), because Ac-crrrrrrrr-NH$_2$ (SEQ ID NO:41) is expected to be taken up into cells by virtue of its cell-penetrating characteristic, and thus removed from proximity to the active portion of the CaSR.

To further explore the structure-activity relationship of Ac-crrrrrr-NH$_2$ (SEQ ID NO:6), some of the cationic (arginine) residues were replaced with uncharged (alanine) residues. It was found that replacing the cationic (arginine) residues at subunit positions $X_2$ and $X_4$ resulted in a compound (SEQ ID NO:15) that had significantly reduced potency in vitro in activating the CaSR. By contrast, replacing the cationic (arginine) residues at subunit positions $X_2$ and $X_6$ resulted in a compound (SEQ ID NO:26) that retained much of the potency seen with Ac-crrrrrr-NH$_2$ (SEQ ID NO:6). These results suggest that the position of charged residues in the compound contributes to potency and, in some embodiments, may outweigh the contribution of total positive charge of the peptide. It also appears that cationic (arginine) residues at certain positions, such as subunit position $X_5$, contribute disproportionately to potency.

It was found that the presence of an N-terminal cysteine markedly enhances the potency of the peptides for activating the CaSR. The CaSR is a 7-transmembrane G-protein-coupled receptor with a large extracellular domain that functions as a homodimeric receptor. There are 18 cysteine residues in the extracellular domain, some of which have been shown by polymorphism or mutational analysis to be important for receptor activity. Of particular note are cysteines 129 and 131 of the Loop 2 region of the extracellular domain. Cysteines 129 and 131 are thought to form an intermolecular disulfide bridge between the two monomers of the receptor complex, which is in a closed or inhibited configuration. Mutation of cysteine 129 activates the CaSR, as do a number of other mutations including a full deletion of the Loop2 region. The enhanced potency provided by the N-terminal cysteine residue in the described compounds could result from a specific interaction with one or more of the cysteine residues in the extracellular domain of the CaSR.

To further evaluate the effect of chirality of amino acid substitutions on in vitro CaSR activity, a series of analogs of Ac-crrrrrr-NH$_2$ (SEQ ID NO:6) were generated containing L-amino acid or achiral amino acid (glycine) substitutions at various positions and tested for potency against the CaSR. Tested analogs included Ac-cGrrrGr-NH$_2$ (SEQ ID NO:42), (ii) Ac-cArrrAr—NH$_2$ (SEQ ID NO:43), and (iii) Ac—CaR-rRaR—NH$_2$ (SEQ ID NO:44). All of the foregoing analogs had significantly lower potency than Ac-crrrrrr-NH$_2$ (SEQ ID NO:6), ranging from a 10-fold difference for SEQ ID NO:44 (the most potent of the three analogs) and a more than 2000-fold difference for SEQ ID NO:43 (the least potent of the three analogs). Ac-carrrar-NH$_2$ (SEQ ID NO:26), in which cationic D-amino acid residues (D-arginine residues) at positions 2 and 6 of SEQ ID NO:6 were replaced by uncharged D-amino acid residues (D-arginine residues), the change in activity was much less (−3 fold difference). Thus, surprisingly, it was found that interrupting the all D-amino acid residue of Ac-crrrrrr-NH$_2$ (SEQ ID NO:6) with two or more L-amino acid residues resulted in a significant reduction in potency. Also surprising was that potency was decreased more than 80-fold when the interrupting residue was an uncharged achiral amino acid residue (glycine residue) compared to when it was an uncharged L-amino acid residue (L-alanine residue).

Also surprising was that replacing the two uncharged D-amino acid residues (D-alanine residues) of Ac-carrrar-NH$_2$ (SEQ ID NO:26) with their L-counterparts (SEQ ID NO:43), resulted in a greater than 600-fold decrease in potency, while replacing them with an uncharged achiral amino acid residue (glycine residue) (SEQ ID NO:42) resulted in less than an 8-fold reduction in potency; and that replacing three cationic D-amino acid residues (D-arginine residues) of Ac-carrrar-NH$_2$ (SEQ ID NO:26) with their L-counterparts (SEQ ID NO:44), resulted in less than a 4-fold difference in potency.

In another study of the structure activity relationship, the contribution of non-cationic amino acids to the potency of the peptides was evaluated by preparing a series of peptides with various D-amino acid residues or glycine or with sterically-hindered non-natural amino acids, substituted at various positions in the peptide Ac-carrrar-NH$_2$ (SEQ ID NO:26) and in the peptide Ac-crrarar-NH$_2$ (SEQ ID NO:153). The peptides were administered as an IV bolus to normal Sprague Dawley rats at a dose of 0.5 mg/kg. An intravenous (IV) bolus of saline was used as a control. Plasma PTH levels were assessed prior to dosing and 1, 2, 3 and 4 hours after dosing. The results indicate that: 1) a small amino acid such as alanine, glycine or serine is preferred at position 6 in the Ac-carrrar-NH$_2$ peptide (SEQ ID NO:26), and 2) the alanine in position 2 in Ac-carrrar-NH$_2$ (SEQ ID NO:26) is much more permissive to substitutions and can be substituted with hydrophobic (e.g. D-Val, D-Leu), aromatic (e.g. D-Phe), or polar (e.g. D-Ser, D-Gln) natural amino acids as well as non-natural bulky hydrophobic amino acids (e.g. dNle, dNva) but not acidic ones, and that 3) the alanine residue in position 4 of the Ac-crrarar-NH$_2$ (SEQ ID NO:25) peptide is also very permissive to substitutions and can accommodate most types of natural amino acids (as well as non-natural bulky hydrophobic amino acids (e.g. dNle, dNva) but is not permissive to amino acids that affect secondary conformation, namely glycine or proline or amino acids with acidic side chain.

The activity of a variety of peptides and conjugates was tested for their effects on the human CaSR. These studies were conducted by measuring IP$_1$ production in HEK293 cells that express the human CaSR. The results are presented in Table 3 below.

TABLE 3

| Compound Name | Structure | EC$_{50}$ (•M) |
|---|---|---|
| (SEQ ID NO: 45) (SEQ ID NO: 47) | CHDAPIGYD<br>\|<br>Ac-CYGRKKRRQRRR-NH$_2$ | 21 |
| (SEQ ID NO: 46) (SEQ ID NO: 47) | CPDYHDAGI<br>\|<br>Ac-CYGRKKRRQRRR-NH$_2$ | 21 |
| (SEQ ID NO: 47) | Ac-CYGRKKRRQRRR-NH$_2$ | 4.5 |
| (SEQ ID NO: 48) | Ac-YGRKKRRQRRR-NH$_2$ | 16 |
| (SEQ ID NO: 41) | Ac-crrrrrrrr-NH$_2$ | 0.3 |
| (SEQ ID NO: 6) | Ac-crrrrrr-NH$_2$ | 0.5 |
| (SEQ ID NO: 15) | Ac-cararrr-NH$_2$ | 13 |
| (SEQ ID NO: 26) | Ac-carrrar-NH$_2$ | 1.6 |
| (SEQ ID NO: 4) | Ac-crrrr-NH$_2$ | 16 |
| (SEQ ID NO: 5) | Ac-crrrrr-NH$_2$ | 2.5 |
| (SEQ ID NO: 7) | Ac-crrrrrrr-NH$_2$ | 0.6 |
| (SEQ ID NO: 49) | Ac-caraarrr-NH$_2$ | 1000 |
| (SEQ ID NO: 8) | Ac-carrrrr-NH$_2$ | 1.1 |
| (SEQ ID NO: 9) | Ac-crarrrr-NH$_2$ | 1 |
| (SEQ ID NO: 10) | Ac-crrarrr-NH$_2$ | 1.1 |
| (SEQ ID NO: 50) | Ac-cygrkkrrqrrr-NH$_2$ | 2 |

TABLE 3-continued

| Compound Name | Structure | EC$_{50}$ (•M) |
|---|---|---|
| (SEQ ID NO: 51) | H$_2$N-crrrrrr-NH$_2$<br>         \|<br>H$_2$N-crrrrrr-NH$_2$ | 0.44 |
| (SEQ ID NO: 3) | Ac-c(C)arrrar-NH$_2$ | 10 |
| (SEQ ID NO: 52) | Ac-carrrar-NH$_2$<br>     \|<br>Ac-carrrar-NH$_2$ | 0.7 |
| (SEQ ID NO: 30) | Ac-bAla-crrrrrr-NH$_2$ | 1 |
| (SEQ ID NO: 53) | Ac-c(GS)rrrrrr-NH$_2$ | 7.8 |
| (SEQ ID NO: 54) | GS-crrrrrr | – |
| (SEQ ID NO: 55) | Ac-c(Ac-C)arrrar-NH$_2$ | 21 |
| (SEQ ID NO: 56) | Ac-c(Mpa)arrrar-NH$_2$ | 21 |
| (SEQ ID NO: 57) | Ac-c(PEG2-C)arrrar-NH$_2$ | 2.3 |
| (SEQ ID NO: 58) | Ac-c(PEG5-C)rrrrrr-NH$_2$ | 0.58 |
| (SEQ ID NO: 59) | Ac-c(PEG2-C)rrrrrr-NH$_2$ | 0.02 |
| (SEQ ID NO: 34) | Ac-C(C)arrrar-NH$_2$ | 2.5 |
| (SEQ ID NO: 60) | c(C)arrrar-NH$_2$ | 3.1 |
| (SEQ ID NO: 61) | Ac-bAla-c(C)arrrar-NH$_2$ | 2.6 |
| (SEQ ID NO: 62) | bAla-c(C)arrrar | – |
| (SEQ ID NO: 42) | Ac-cGrrrGr-NH$_2$ | 12 |
| (SEQ ID NO: 63) | Ac-cGrrrGr | – |
| (SEQ ID NO: 64) | Ac-cArrrAr | – |
| (SEQ ID NO: 43) | Ac-cArrrAr-NH$_2$ | >1000 |
| (SEQ ID NO: 44) | Ac-CaRrRaR-NH$_2$ | 5.6 |
| (SEQ ID NO: 65) | Ac-cvrrrvr-NH$_2$ | 35 |
| (SEQ ID NO: 66) | Ac-cvrrrvr | – |
| (SEQ ID NO: 67) | Ac-Crrrrrr-NH$_2$ | 6.2 |
| (SEQ ID NO: 68) | Ac-carrrer-NH$_2$ | 62 |
| (SEQ ID NO: 69) | Ac-cerrrar-NH$_2$ | 31 |
| (SEQ ID NO: 72) | Ac-cakrrar-NH$_2$ | 35 |
| (SEQ ID NO: 73) | Ac-carkrar-NH$_2$ | 31 |
| (SEQ ID NO: 74) | Ac-carrrar-OH | 31 |
| (SEQ ID NO: 11) | Ac-crrrarr-NH$_2$ | 5.9 |
| (SEQ ID NO: 12) | Ac-crrrrar-NH$_2$ | 0.45 |
| (SEQ ID NO: 13) | Ac-crrrrra-NH$_2$ | 1.1 |
| (SEQ ID NO: 75) | Ac-CARRRAR-NH$_2$ | 58 |
| (SEQ ID NO: 76) | Ac-caarrrrrr-NH$_2$ | 4.5 |
| (SEQ ID NO: 77) | Ac-caaarrrrrr-NH$_2$ | 4.6 |
| (SEQ ID NO: 78) | Ac-carararar-NH$_2$ | 5.3 |
| (SEQ ID NO: 29) | Ac-arrrar-NH$_2$ | >1000 |
| (SEQ ID NO: 79) | Ac-carrrarar-NH$_2$ | 13 |
| (SEQ ID NO: 80) | crrrrrr-NH$_2$ | 1.1 |
| (SEQ ID NO: 32) | Ac-dHcy rrrrrr-NH$_2$ | 2 |
| (SEQ ID NO: 81) | Ac-c(Benzoyl)rrrrrr-NH$_2$ | 3.6 |
| (SEQ ID NO: 82) | Ac-c(acetyl)rrrrrr-NH$_2$ | 4.1 |

The compounds disclosed herein typically comprise one or more thiol moieties, preferably one or more reactive thiol moieties. Subunits that have a thiol group include non-amino acid compounds having a thiol group and amino acids with a thiol group. The thiol group of the thiol-containing subunit may be in a conjugated form (e.g., via a disulfide bond to a conjugating group) or in an unconjugated form (i.e., as a reduced thiol). In a preferred embodiment, when the thiol group is in either an unconjugated form or a conjugated form, it is capable of forming a disulfide bond with a thiol-containing group. The thiol-containing residue may be located at any position along the peptide chain, including the amino terminus, the carboxy terminus, or some other position. In a preferred embodiment, the thiol-containing residue or subunit may be located at the amino terminus. In other embodiments, the thiol-containing residue or subunit may be located at the carboxy terminus or within the peptide sequence.

Some representative examples of thiol-containing residues include, without limitation, cysteine, mercaptopropionic acid, homo-cysteine, and penicillamine. When the thiol-containing residue contains a chiral center, it may be present in the L- or D-configuration. In a preferred embodiment, the thiol-containing residue is cysteine.

In some embodiments, the cross-linkage between the thiol containing subunit at the $X_1$ position in the compound and the thiol-containing conjugating group may be cleavable and/or exchangeable with other thiol-containing conjugating groups such as cysteine (e.g., by reduction of the disulfide linkage) in vivo to yield a biologically active form of the compound. In this way, the conjugate may function as a pro-drug of the compound. A conjugating group also may be used to modify the physicochemical, pharmacokinetic and/or pharmacodynamic properties of the described compounds (e.g., conjugation via a disulfide linkage to a large PEGylated moiety to enhance the pharmacokinetics).

In some embodiments, the compound is a peptide comprised of the amino acid sequence $(X_{aa1})$—$(X_{aa2})$—$(X_{aa3})$—$(X_{aa4})$—$(X_{aa5})$—$(X_{aa6})$—$(X_{aa7})$ (SEQ ID NO:155), wherein $(X_{aa1})$ is a thiol-containing amino acid residue, $(X_{aa2})$ is a non-cationic amino acid residue, $(X_{aa3})$ is any amino acid residue, $(X_{aa4})$ is any amino acid residue, $(X_{aa6})$ is a cationic amino acid residue, $(X_{aa6})$ is a non-cationic residue, and $(X_{aa7})$ is any amino acid residue. The peptide may be modified at the N-terminus, the C-terminus, or both. In a preferred embodiment, the peptide is modified at both the N-terminus and C-terminus by acetylation and amidation, respectively.

In some embodiments, a peptide comprises the amino acid sequence (D-CyS)—$(X_{aa2})$—$(X_{aa3})$—$(X_{aa4})$—$(X_{aa5})$—$(X_{aa6})$—$(X_{aa7})$ (SEQ ID NO:156), wherein $(X_{aa2})$ is a non-cationic amino acid residue, $(X_{aa3})$ is any amino acid residue, $(X_{aa4})$ is any amino acid residue, $(X_{aa6})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)—$(X_{aa2})$—$(X_{aa3})$—$(X_{aa4})$—$(X_{aa5})$—$(X_{aa6})$—$(X_{aa7})$ (SEQ ID NO:157), wherein $(X_{aa2})$, $(X_{aa3})$ and $(X_{aa4})$ are, independently, any amino acid residue (but in a preferred embodiment are, independently, selected from the group consisting of D-Ala, D-Val, D-Leu, D-NorVal, and D-NorLeu), $(X_{aa5})$ and $(X_{aa7})$ are, independently, any cationic amino acid residue (but in a preferred embodiment are, independently, selected from the group consisting of D-Arg, L-Arg, D-Lys and L-Lys), $(X_{aa6})$ is a non-cationic amino acid residue (in a preferred embodiment, selected from the group consisting of D-Ala, D-Val, D-Leu, D-NorVal and D-NorLeu). The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-$(X_{aa2})$—$(X_{aa3})$—$(X_{aa4})$—$(X_{aa5})$—$(X_{aa6})$—$(X_{aa7})$ (SEQ ID NO:158), wherein $(X_{aa2})$ is a non-cationic amino acid residue, $(X_{aa3})$ is any amino acid residue, $(X_{aa4})$ is any amino acid residue, $(X_{aa5})$ is selected from the group consisting of D-Arg, L-Arg, D-Lys and L-Lys, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-(D-Ala)-$(X_{aa3})$—$(X_{aa4})$-(D-Arg)-(D-Ala)-$(X_{aa7})$ (SEQ ID NO:159), wherein $(X_{aa3})$ is any cationic amino acid residue, $(X_{aa4})$ is any cationic amino acid residue, and $(X_{aa7})$ is any cationic amino acid residue. The peptide may have an N-terminal cap, a C-terminal cap, or both. In a preferred embodiment, the peptide has both an N-terminal cap and a C-terminal cap.

In some embodiments, a peptide comprises the amino acid sequence (D-Cys)-$(X_{aa2})$—$(X_{aa3})$-(D-Ala)-(D-Arg)-(D-Ala)-$(X_{aa7})$ (SEQ ID NO:160), wherein $(X_{aa2})$, $(X_{aa3})$ and $(X_{aa7})$ are, independently, any cationic amino acid residue. The peptide may have an N-terminal cap, a C-terminal cap, or both. In a preferred embodiment, the peptide has both an N-terminal cap and a C-terminal cap.

Another embodiment is a calcimimetic peptide, comprising a sequence of amino acids linked by peptide bonds, wherein the sequence comprises 5 to 10 amino acid residues, and wherein the sequence comprises an amino terminus, a carboxy terminus, at least one thiol-containing residue, and from 3 to 9 positively charged residues. In one embodiment, the at least one thiol-containing residue is a cysteine residue. In another aspect, the cysteine residue is positioned at the amino terminus of the peptide. In certain embodiment, the cysteine residue is an L-Cys residue, a D-Cys residue, or an L- or D-homoCys residue. In other embodiments, the amino acid residues of the peptide are D-amino acids or L-amino acids.

Also encompassed within the scope of the claimed compounds are peptidomimetic molecules that comprise approximately seven subunits, wherein at least one subunit contains a thiol moiety, preferably a reactive thiol moiety, and other subunits are a plurality of non-cationic subunits, and from 1 to 4 positively charged subunits. Such peptidomimetic molecules may comprise non-peptide bonds between two or more of the subunits. The various features of the compounds discussed above apply generally to the peptidomimetic molecule. For example, as discussed above, the subunits used to construct the molecules can be naturally-occurring amino acids, or residues with non-natural side chains, the termini of the modules can be capped or non-capped in the manner discussed above. Similarly, the amino acid residues of the molecule can be L- or D-amino acid residues. Also as discussed above, the thiol-containing residues can be in a reduced or oxidized form with any of the thiol-containing moieties discussed above.

Many peptidomimetic frameworks and methods for their synthesis have been developed (Babine, R. E.; Bender, S. L., Chem. Rev., 97:1359, 1997; Hanessian, S.; et al., Tetrahedron, 53:12789, 1997; Fletcher, M. D.; Cambell, M. C., Chem. Rev., 98:763, 1998); Peptidomimetics Protocols; Kazmierski W. M., Ed.; Methods in Molecular Medicine Series, Vol. 23; Humana Press, Inc.; Totowa, N.J. (1999).

Conjugates

In some embodiments, the compound is chemically cross-linked to a thiol-containing conjugating group via a disulfide bond between the thiol of the compound and a thiol from the conjugating group. The thiol-containing conjugating group can be a small molecule, such as cysteine, or a macromolecule, such as a polypeptide containing a cysteine residue. Examples of suitable thiol-containing conjugating groups include cysteine, glutathione, thioalkyl, moieties such as thiobenzyl, mercaptopropionic acid, N-acetylated cysteine, cysteamide, N-acetylcysteamide, homocysteine, penicillamine and poly (ethylene glycol) (PEG) modified (referred to as "PEGylated") thiols such as PEGylated cysteine or a duplication of the compound (ie., to form a homodimer linked by a disulfide linkage). In a preferred embodiment, the thiol-containing conjugating group is cysteine. Other cysteine homologs are also contemplated for use as thiol-containing conjugating groups, either alone or comprised in a larger conjugating group. Similarly, stereoisomers of cysteine, homocysteine, and cysteamide are suitable for use as thiol-containing moieties. Conjugating groups can be used to improve chemical stability and therefore shelf-life of a pharmaceutical product. In certain embodiments the thiol-containing conjugating group and the peptide are the same (i.e., the conjugate is a dimer), which unexpectedly showed very good chemical stability compared to heterologous conjugating group such as cysteine. Without being bound by theory, presumably when the thiol-containing conjugating group and the peptide are the same, then any disproportionation (e.g., scrambling of the conjugating group) will reconstitute the original dimer compound. In contrast, disproportionation of a compound with a heterologous conjugating group such as cysteine can lead to formation of homo-dimers of the peptide plus cystine (cysteine—cysteine homodimer) plus residual parent compound. A homo-dimer of the peptide (i.e., conjugating group and the peptide are the same) would be converted to a cysteine conjugated form of the peptide in vivo due to the high concentration of reduced cysteine in systemic circulation.

In some embodiments, the teachings include a disulfide conjugate of a thiol-containing conjugating group and a peptide comprising the amino acid sequence $(X_{aa1})$—$(X_{aa2})$—$(X_{aa3})$—$(X_{aa4})$—$(X_{aa5})$—$(X_{aa6})$—$(X_{aa7})$ (SEQ ID NO:155), wherein $(X_{aa1})$ is an amino acid residue with a thiol-containing moiety, $(X_{aa2})$ is a non-cationic amino acid residue, $(X_{aa3})$ is any amino acid residue, $(X_{aa4})$ is any amino acid residue, $(X_{aa5})$ is a cationic amino acid residue, $(X_{aa6})$ is a non-cationic residue, and $(X_{aa7})$ is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:155. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (D-Cys)—($X_{aa2}$)—($X_{aa3}$)—($X_{aa4}$)—($X_{aa5}$)—($X_{aa6}$)—($X_{aa7}$) (SEQ ID NO:156), wherein ($X_{aa2}$) is a non-cationic amino acid residue, ($X_{aa3}$) is any amino acid residue, ($X_{aa4}$) is any amino acid residue, ($X_{aa5}$) is selected from the group consisting of D-Arg, L-Arg, D-Lys and L-Lys, ($X_{aa6}$) is a non-cationic residue, and ($X_{aa7}$) is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:156. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (L-Cys)-($X_{aa2}$)—($X_{aa3}$)—($X_{aa4}$)—($X_{aa5}$)—($X_{aa6}$)—($X_{aa7}$) (SEQ ID NO:183), wherein ($X_{aa2}$) is a non-cationic amino acid residue, ($X_{aa3}$) is any amino acid residue, ($X_{aa4}$) is any amino acid residue, ($X_{aa5}$) is selected from the group consisting of D-Arg, L-Arg, D-Lys and L-Lys, ($X_{aa6}$) is a non-cationic residue, and ($X_{aa7}$) is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:183. In some embodiments, the thiol-containing conjugating group and the peptide are the same (i.e., the conjugate is a dimer).

In some embodiments, the teachings include a conjugate of a thiol-containing conjugating group and a peptide comprising the amino acid sequence (D-Cys)-(D-Ala)-($X_{aa3}$)—($X_{aa4}$)-(D-Arg)-(D-Ala)-($X_{aa7}$) (SEQ ID NO:161), wherein ($X_{aa3}$) is any amino acid residue, ($X_{aa4}$) is any amino acid residue, and ($X_{aa7}$) is any amino acid residue. The peptide may have an N-terminal cap, a C-terminal cap, or both. In a preferred embodiment, the peptide has both an N-terminal cap and a C-terminal cap. In a preferred embodiment, the thiol-containing conjugating group is selected from the group consisting of D-Cys, L-Cys, a peptide containing D-Cys, and a peptide containing L-Cys. When the thiol-containing conjugate group is an amino acid or a peptide, it may have an N-terminal cap, a C-terminal cap, or both. In a preferred embodiment, the thiol-containing conjugate group has both an N-terminal cap and a C-terminal cap. In some embodiments, the thiol-containing conjugating group is itself a peptide comprising the amino acid sequence of SEQ ID NO:161. In some embodiments, the thiol-containing conjugating group and the peptide are the same (i.e., the conjugate is a dimer).

Exemplary Compounds

In a preferred embodiment, the thiol-containing conjugate group has both an N-terminal cap and a C-terminal cap. In some embodiments, the thiol-containing conjugating group is itself a peptide comprising the amino acid sequence of SEQ ID NO:161. In some embodiments, the thiol-containing conjugating group and the peptide are the same (i.e., the conjugate is a dimer).

In another embodiment, compounds are in the form of a conjugate, where the thiol-containing subunit in position $X_1$ is linked through a disulfide linkage to an L-Cys residue. These compounds have the following structures:

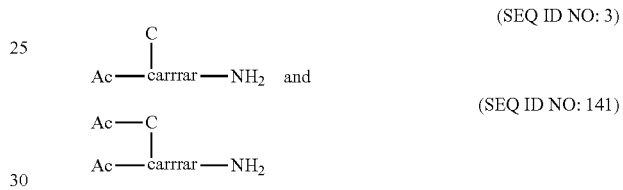

In the notation used herein, the compound that is linked to the thiol-containing moiety in the $X_1$ subunit is identified parenthetically, where in these exemplary conjugates the compound L-Cys is indicated (C) is linked to the thiol-containing moiety in the $X_1$ subunit: Ac-c(C)arrrar-NH$_2$ (SEQ ID NO:3) and Ac-c(Ac—C)arrrar-NH$_2$ (SEQ ID NO:141).

When the described agonists are administered as pharmaceuticals, to humans and animals, they can be given alone or as a pharmaceutical composition containing, for example, 0.1 to 99% (more preferably, 10 to 30%) of active ingredient in combination with a pharmaceutically acceptable carrier. In other embodiments, the pharmaceutical composition may contain 0.2-25%, preferably 0.5-5% or 0.5-2%, of active ingredient. These compounds may be administered to humans and other animals for therapy by any suitable route of administration, including, e.g., oral, subcutaneous injection, subcutaneous depot, intravenous injection, intravenous or subcutaneous infusion These agonists may be administered to humans and other animals for therapy by any suitable route of administration.

As described above, the methods of use may be used alone or in combination with other agents and/or modalities. Such other agents and/or modalities include, but are not limited to, dietary phosphate restriction, dialysis, phosphate binders (e.g., aluminum hydroxide, calcium carbonate, calcium acetate, magnesium salts, sevelamer hydrochloride, lanthanum carbonate, polynuclear iron preparation). The particular combination of therapies (agents and/or modalities) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, a described compound is administered at a dose sufficient to reduce phosphorus rebound in a hemodialysis patient. In another embodiment, the dose is administered after termination of dialysis.

A combination treatment of the present invention as defined herein may be achieved by way of the simultaneous, sequential or separate administration of the individual components of said treatment.

EXAMPLES

The following example is offered to illustrate but not to limit the compounds and methods described herein. Various modifications may be made by the skilled person without departing from the true spirit and scope of the subject matter described herein.

Example 1

An initial Phase 1 randomized, double-blind, placebo-controlled, single-dose, dose-escalation, two-period crossover study in ESRD patients on hemodialysis with SHPT was carried out. The study was conducted in part to assess the safety, tolerability, pharmacokinetics and pharmacodynamics of intravenous (IV) administration of SEQ ID NO:3 in healthy male volunteers and to inform dose selection for this protocol. This study was a Phase 1b study in hemodialysis subjects with SHPT.

Twenty-eight patients on hemodialysis were given a single dose of SEQ ID NO:3 or placebo. Cohorts receiving a 5, 10 or 20 mg dose were studied in a 2-period cross-over design while subjects receiving a 40 or 60 mg dose were randomized to SEQ ID NO:3 or placebo with 8 subjects per cohort.

Immediately following hemodialysis, subjects were admitted to a Phase 1 Unit and observed for 3 days. Baseline laboratory testing was performed 2 hours post hemodialysis. Following injection of SEQ ID NO:3 post dialysis, there is a rapid 60-80% decrease in the levels of intact PTH followed by a dose dependant return towards baseline over the following 48 hours (FIG. 1). There is an associated small (10-16%) decrease in serum calcium.

Serum phosphorus levels, which were decreased by dialysis, rose rapidly over the first 8 hours to a plateau and then increased more slowly during the remaining interdialytic interval (FIG. 2). In placebo subjects, mean serum phosphorus increased rapidly during the first ~36 hours post-dose after which phosphorus levels tended to plateau at 84% above baseline levels at discharge (FIG. 2). Surprisingly, the rate of return to the plateau level of phosphorus was markedly modified by administration of SEQ ID NO:3. The 5 mg dose had minimal effect, but higher doses markedly decreased the rise of serum phosphorus. At discharge, the mean percent increase from baseline in serum phosphorus in subjects receiving 20-60 mg SEQ ID NO:3 ranged from 23% to 60% and was at least ~24 percentage points lower than placebo.

Example 2

A Phase 2 study was completed as a double-blind, randomized placebo-controlled, multiple ascending dose study. This study was a single arm, open-label, 12-week, dose titration study with a 4-week follow-up phase to investigate the effect of SEQ ID NO:3 in the treatment of SHPT in hemodialysis subjects with chronic kidney disease-mineral and bone disorder (CKD-MBD). The primary objective of this study was to evaluate the effect of thrice-weekly IV administration of SEQ ID NO:3 in the treatment of SHPT in hemodialysis subjects with CKD-MBD as assessed by percent change in iPTH from baseline during the efficacy period. In addition, secondary objectives were to evaluate the change from baseline in serum cCa (corrected calcium) and phosphorus.

The starting dose of SEQ ID NO:3 was 5 mg. The dose of SEQ ID NO:3 was titrated to target 150≤300 pg/mL. Subjects were evaluated for an increase in the SEQ ID NO:3 dose during Week 5 and Week 9. If the subject's most recent cCa was ≥8.0 mg/dL and there was no ongoing adverse event that precluded a dose increase, then the dose of SEQ ID NO:3 was adjusted as follows: if iPTH≤300 pg/mL, then no change in dose; If iPTH>300 pg/mL, then the dose was increased by 5 mg (i.e., from 5 mg to 10 mg) during Week 5 or increased by 5 mg (i.e., iPTH≥300 pg/mL and ≤450 pg/mL) or 10 mg (iPTH>450 pg/mL) during Week 9.

Thirty-two subjects (87%) completed the 12-week treatment period. Five subjects (13/5%) withdrew prior to the end of the treatment period. Of the 32 subjects who completed the 12-week treatment period, 30 subjects entered the open-label extension study and two subjects completed the 4-week follow-up period.

The primary endpoint was the percent change from baseline in iPTH at the end of the efficacy assessment period. Baseline iPTH level was defined as the average of three iPTH results obtained within 3 weeks of the first dose and prior to the first dose of SEQ ID NO:3. The efficacy assessment period was from 14 days prior to and 3 days after the last dose of SEQ ID NO:3. Secondary endpoints included the proportion of subjects with ≥30% reduction in iPTH from baseline and the proportion of subjects with iPTH≥300 pg/mL during the efficacy assessment period. In addition, the effect of SEQ ID NO:3 on mean change in cCa and phosphorus were evaluated.

Overall, mean baseline iPTH was 853.4 pg/mL. SEQ ID NO:3 treatment was associated with a 53% mean reduction from baseline in iPTH at the end of the treatment period (95% confidence interval (−60.8, −46.3). Results were similar in the iPTH subgroups (baseline iPTH≤700 pg/mL or >700 pg/mL), suggesting that the response was independent of baseline iPTH values.

When plotted versus time, SEQ ID NO:3 treatment showed a progressive, sustained reduction in predialysis iPTH over the 12-week treatment period. In a secondary responder analysis 89% of subjects achieved ≥30% reduction in iPTH; the proportion was only slightly lower among subjects with severe disease (i.e., iPTH>700 pg/mL). Overall, 56% of subjects achieved iPTH≤300 pg/mL at the end of the treatment period. Serum calcium levels were adjusted for albumin levels below 4.0 g/dL with the equation: corrected calcium (cCa) =(measured Ca in mg/dL)+[4-(albumin in g/dL)]*0.8. Mean baseline cCa was 10.1 mg/dL and was reduced by 15% at the end of the treatment period. More pronounced decreases in serum cCa were observed in subjects with severe disease.

Phosphorus measurements were obtained predialysis on protocol specified assessment days. Overall, mean baseline phosphorus was 5.7 mg/dL, with the more severe baseline iPTH subgroup having higher baseline levels. At the end of the efficacy treatment period, the mean percent change from baseline in serum phosphorus was −10.5%, with the greater reduction experienced in the subjects with more severe disease (Table 3).

TABLE 3

| Serum Phosphorus (P) in mg/dL | iPTH ≤ 700 N = 22 | iPTH > 700 N = 15 | Total N = 37 |
|---|---|---|---|
| Baseline | 5.1 | 6.5 | 5.7 |
| EOT | 4.7 | 5.5 | 5.0 |
| Mean percent Change (%) | −7.7 | −14.5 | −10.5 |

TABLE 3-continued

| Serum Phosphorus (P) in mg/dL | iPTH ≤ 700 N = 22 | iPTH > 700 N = 15 | Total N = 37 |
|---|---|---|---|
| 95% CI of Mean percent Change | −17.7, 2.3 | −23.4, −5.6 | −17.2, −3.9 |

Overall, with the exception of the one phosphorus mean percent change in the lower iPTH subgroup, all prespecified primary and secondary endpoints analyses showed significant reductions in iPTH, cCa and phosphorus across both subgroups.

The invention claimed is:

1. A method, comprising:
   administering to a patient undergoing hemodialysis a compound comprising Ac-c(C)arrrar-NH$_2$ (SEQ ID NO:3) or a pharmaceutically acceptable salt thereof;
   wherein the compound is administered intravenously to the patient during the period beginning about 15 minutes prior to the completion of the hemodialysis and ending about 3 hours after completion of the hemodialysis, and
   wherein said administering is effective to maintain a post-hemodialysis serum phosphorus level that is lower than a pre-hemodialysis serum phosphorus level for the duration of the interdialytic period.

2. The method of claim 1, wherein the compound comprises a pharmaceutically acceptable salt of SEQ ID NO:3.

3. The method of claim 2, wherein the salt is a hydrochloride salt.

4. The method of claim 1, wherein the compound is administered within the period beginning about 15 minutes prior to completion of hemodialysis and ending about 1 hour after completion of hemodialysis.

5. The method of claim 1, wherein the compound is administered during the rinse back procedure at the end of dialysis.

6. The method of claim 1, wherein the patient has been diagnosed with end stage renal disease or chronic kidney disease.

7. The method of claim 1, wherein the patient is being treated with a drug that binds phosphate.

8. The method of claim 1, wherein said administering is effective to maintain a post-hemodialysis serum phosphorus level that is at least about 10% lower than a pre-hemodialysis serum phosphorus level for the inter-dialytic period.

9. The method of claim 1, wherein patient is being treated for secondary hyperparathyroidism or primary hyperparathyroidism.

10. The method of claim 1, wherein the L-cysteine is modified by acetylation.

\* \* \* \* \*

SEQUENCE LISTING

```
<160> NUMBER OF SEQ ID NOS: 183

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(7)
<223> OTHER INFORMATION: Xaa = any amino acid as defined in the
      specification filed herewith

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg

<400> SEQUENCE: 2

Xaa Xaa Xaa Xaa Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
```

```
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 3

Xaa Xaa Xaa Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5)
<223> OTHER INFORMATION: Xaa = D-Arg
<220> FEATURE:
<221> NAME/KEY: MOD_RES
<222> LOCATION: (5)
<223> OTHER INFORMATION: C-terminal amidation

<400> SEQUENCE: 4

Xaa Xaa Xaa Xaa Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(6)
<223> OTHER INFORMATION: Xaa = D-Arg
<220> FEATURE:
<221> NAME/KEY: MOD_RES
<222> LOCATION: (6)
<223> OTHER INFORMATION: C-terminal amidation

<400> SEQUENCE: 5

Xaa Xaa Xaa Xaa Xaa Xaa
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 6

Xaa Xaa Xaa Xaa Xaa Xaa Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 7

Xaa Xaa Xaa Xaa Xaa Xaa Xaa Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(2)
<223> OTHER INFORMATION: Xaa = D-Ala
<220> FEATURE:
<221> NAME/KEY: VARIANT
<222> LOCATION: (3)...(7)
```

```
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 8

Xaa Xaa Xaa Xaa Xaa Xaa Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)..(2)
<223> OTHER INFORMATION: Xaa = D-Arg
<220> FEATURE:
<221> NAME/KEY: VARIANT
<222> LOCATION: (3)..(3)
<223> OTHER INFORMATION: Xaa = D-Ala
<220> FEATURE:
<221> NAME/KEY: VARIANT
<222> LOCATION: (4)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 9

Xaa Xaa Xaa Xaa Xaa Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5)...(7)
<223> OTHER INFORMATION: Xaa = D-Arg
<220> FEATURE:
<221> NAME/KEY: VARIANT
<222> LOCATION: (4)..(4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 10

Xaa Xaa Xaa Xaa Xaa Xaa Xaa
```

```
<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(4), (6)...(7)
<223> OTHER INFORMATION: Xaa = D-Arg
<220> FEATURE:
<221> NAME/KEY: VARIANT
<222> LOCATION: (5)..(5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 11

Xaa Xaa Xaa Xaa Xaa Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5), (7)
<223> OTHER INFORMATION: Xaa = D-Arg
<220> FEATURE:
<221> NAME/KEY: VARIANT
<222> LOCATION: (6)..(6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 12

Xaa Xaa Xaa Xaa Xaa Xaa Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
```

```
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(6)
<223> OTHER INFORMATION: Xaa = D-Arg
<220> FEATURE:
<221> NAME/KEY: VARIANT
<222> LOCATION: (7)..(7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 13

Xaa Xaa Xaa Xaa Xaa Xaa Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (6)
<223> OTHER INFORMATION: Xaa = D-Arg
<220> FEATURE:
<221> NAME/KEY: VARIANT
<222> LOCATION: (4), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 14

Xaa Xaa Xaa Xaa Xaa Xaa Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4)
<223> OTHER INFORMATION: Xaa = D-Ala
<220> FEATURE:
<221> NAME/KEY: VARIANT
<222> LOCATION: (3), (5) (6), (7)
<223> OTHER INFORMATION: Xaa = D-Arg
<220> FEATURE:
```

```
<221> NAME/KEY: MOD_RES
<222> LOCATION: (7)
<223> OTHER INFORMATION: C-terminal amidation

<400> SEQUENCE: 15

Xaa Xaa Xaa Xaa Xaa Xaa Xaa
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5)
<223> OTHER INFORMATION: Xaa = D-Ala
<220> FEATURE:
<221> NAME/KEY: VARIANT
<222> LOCATION: (3), (4), (6), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 16

Xaa Xaa Xaa Xaa Xaa Xaa Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (6), (7)
<223> OTHER INFORMATION: Xaa = D-Arg
<220> FEATURE:
<221> NAME/KEY: VARIANT
<222> LOCATION: (4), (5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 17

Xaa Xaa Xaa Xaa Xaa Xaa Xaa
1               5

<210> SEQ ID NO 18
<211> LENGTH: 7
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (6), (7)
<223> OTHER INFORMATION: Xaa = D-Arg
<220> FEATURE:
<221> NAME/KEY: VARIANT
<222> LOCATION: (3), (5)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 18

Xaa Xaa Xaa Xaa Xaa Xaa Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (7)
<223> OTHER INFORMATION: Xaa = D-Ala
<220> FEATURE:
<221> NAME/KEY: VARIANT
<222> LOCATION: (3)...(6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 19

Xaa Xaa Xaa Xaa Xaa Xaa Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
```

```
<222> LOCATION: (2), (4), (5), (6)
<223> OTHER INFORMATION: Xaa = D-Arg
<220> FEATURE:
<221> NAME/KEY: VARIANT
<222> LOCATION: (3), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 20

Xaa Xaa Xaa Xaa Xaa Xaa Xaa
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (4), (7)
<223> OTHER INFORMATION: Xaa = D-Arg
<220> FEATURE:
<221> NAME/KEY: VARIANT
<222> LOCATION: (5), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 21

Xaa Xaa Xaa Xaa Xaa Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(3)
<223> OTHER INFORMATION: Xaa = D-Ala
<220> FEATURE:
<221> NAME/KEY: VARIANT
<222> LOCATION: (4)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 22
```

Xaa Xaa Xaa Xaa Xaa Xaa Xaa
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (5), (7)
<223> OTHER INFORMATION: Xaa = D-Arg
<220> FEATURE:
<221> NAME/KEY: VARIANT
<222> LOCATION: (3), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 23

Xaa Xaa Xaa Xaa Xaa Xaa Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5), (6), (7)
<223> OTHER INFORMATION: Xaa = D-Arg
<220> FEATURE:
<221> NAME/KEY: VARIANT
<222> LOCATION: (3), (4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 24

Xaa Xaa Xaa Xaa Xaa Xaa Xaa
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)

<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 25

Xaa Xaa Xaa Xaa Xaa Xaa Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 26

Xaa Xaa Xaa Xaa Xaa Xaa Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala

```
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 27

Xaa Xaa Xaa Xaa Xaa Xaa Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 28

Xaa Xaa Xaa Xaa Xaa Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1), (5)
<223> OTHER INFORMATION: Xaa = D-Ala
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (4), (6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 29

Xaa Xaa Xaa Xaa Xaa Xaa
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = bAla
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Cys
<220> FEATURE:
<221> NAME/KEY: VARIANT
<222> LOCATION: (3)...(8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 30

Xaa Xaa Xaa Xaa Xaa Xaa Xaa Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = 3-Mercaptopropionic acid
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 31

Xaa Xaa Xaa Xaa Xaa Xaa Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Homocysteine
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
```

```
<221> NAME/KEY: MOD_RES
<222> LOCATION: (7)
<223> OTHER INFORMATION: C-terminal amidation

<400> SEQUENCE: 32

Xaa Xaa Xaa Xaa Xaa Xaa Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-penicillamine
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 33

Xaa Xaa Xaa Xaa Xaa Xaa Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys interchain disulfide bond
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 34

Xaa Xaa Xaa Xaa Xaa Xaa Xaa
1               5

<210> SEQ ID NO 35
<211> LENGTH: 7
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 35

Cys Xaa Xaa Xaa Xaa Xaa Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 36

Xaa Xaa Arg Xaa Xaa Xaa Xaa
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
```

```
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 37

Xaa Xaa Xaa Arg Xaa Xaa Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 38

Xaa Xaa Xaa Xaa Arg Xaa Xaa
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
```

```
<223> OTHER INFORMATION: Cys-Cys disulfide bond to Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 39

Xaa Xaa Xaa Xaa Xaa Ala Xaa
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bond to Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (6)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 40

Xaa Xaa Xaa Xaa Xaa Xaa Arg
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(9)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation
```

<400> SEQUENCE: 41

Xaa Xaa Xaa Xaa Xaa Xaa Xaa Xaa Xaa
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 42

Xaa Gly Xaa Xaa Xaa Gly Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 43

Xaa Ala Xaa Xaa Xaa Ala Xaa
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (4)
<223> OTHER INFORMATION: Xaa = D-Arg

```
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 44

Cys Xaa Arg Xaa Arg Xaa Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Cys His Asp Ala Pro Ile Gly Tyr Asp
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

Cys Pro Asp Tyr His Asp Ala Gly Ile
1               5

<210> SEQ ID NO 47
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (12)..(12)
<223> OTHER INFORMATION: C-terminal amidation

<400> SEQUENCE: 47

Cys Tyr Gly Arg Lys Lys Arg Arg Gln Arg Arg Arg
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (11)..(11)
<223> OTHER INFORMATION: C-terminal amidation

<400> SEQUENCE: 48
```

Tyr Gly Arg Lys Lys Arg Arg Gln Arg Arg Arg
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (5)
<223> OTHER INFORMATION: Xaa = D-Ala
<220> FEATURE:
<221> NAME/KEY: VARIANT
<222> LOCATION: (3), (6), (7), (8)
<223> OTHER INFORMATION: Xaa = D-Arg
<220> FEATURE:
<221> NAME/KEY: MOD_RES
<222> LOCATION: (8)
<223> OTHER INFORMATION: C-terminal amidation

<400> SEQUENCE: 49

Xaa Xaa Xaa Xaa Xaa Xaa Xaa Xaa
1               5

<210> SEQ ID NO 50
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Tyr
<220> FEATURE:
<221> NAME/KEY: VARIANT
<222> LOCATION: (3)
<223> OTHER INFORMATION: Xaa = D-Gly
<220> FEATURE:
<221> NAME/KEY: VARIANT
<222> LOCATION: (4), (7), (8), (10), (11), (12)
<223> OTHER INFORMATION: Xaa = D-Arg
<220> FEATURE:
<221> NAME/KEY: VARIANT
<222> LOCATION: (5), (6)
<223> OTHER INFORMATION: Xaa = D-Lys
<220> FEATURE:
<221> NAME/KEY: VARIANT
<222> LOCATION: (9)
<223> OTHER INFORMATION: Xaa = D-Gln
<220> FEATURE:
<221> NAME/KEY: MOD_RES
<222> LOCATION: (12)
<223> OTHER INFORMATION: C-terminal amidation

<400> SEQUENCE: 50

Xaa Xaa Xaa Xaa Xaa Xaa Xaa Xaa Xaa Xaa Xaa Xaa

```
1               5                   10
```

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 51

Xaa Xaa Xaa Xaa Xaa Xaa Xaa
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 52

Xaa Xaa Xaa Xaa Xaa Xaa Xaa
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation

```
<220> FEATURE:
<221> NAME/KEY: DISULFID
<222> LOCATION: (1)..(1)
<223> OTHER INFORMATION: Cys-Cys disulfide bonded to Glutathione
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 53

Xaa Xaa Xaa Xaa Xaa Xaa Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: DISULFID
<222> LOCATION: (1)..(1)
<223> OTHER INFORMATION: Cys-Cys disulfide bonded to Glutathione
<220> FEATURE:
<221> NAME/KEY: VARIANT
<222> LOCATION: (2)...(7)
<223> OTHER INFORMATION: Xaa = D-Arg

<400> SEQUENCE: 54

Xaa Xaa Xaa Xaa Xaa Xaa Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to acetylated
      Glutathione
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 55

Xaa Xaa Xaa Xaa Xaa Xaa Xaa
```

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to 3-Mercaptopropionic
      acid
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 56

Xaa Xaa Xaa Xaa Xaa Xaa Xaa
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 57

Xaa Xaa Xaa Xaa Xaa Xaa Xaa
1               5

<210> SEQ ID NO 58

```
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 58

Xaa Xaa Xaa Xaa Xaa Xaa Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 59

Xaa Xaa Xaa Xaa Xaa Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
```

```
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys disulfide bonded to Cys
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 60

Xaa Xaa Xaa Xaa Xaa Xaa Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = bAla
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Cys
<220> FEATURE:
<221> NAME/KEY: DISULFID
<222> LOCATION: (2)..(2)
<223> OTHER INFORMATION: Cys-Cys disulfide bonded to Cys
<220> FEATURE:
<221> NAME/KEY: VARIANT
<222> LOCATION: (3), (7)
<223> OTHER INFORMATION: Xaa = D-Ala
<220> FEATURE:
<221> NAME/KEY: VARIANT
<222> LOCATION: (4), (5), (6), (8)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 61

Xaa Xaa Xaa Xaa Xaa Xaa Xaa Xaa
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = bAla
<220> FEATURE:
```

```
<221> NAME/KEY: VARIANT
<222> LOCATION: (2)
<223> OTHER INFORMATION: Xaa = D-Cys
<220> FEATURE:
<221> NAME/KEY: DISULFID
<222> LOCATION: (2)..(2)
<223> OTHER INFORMATION: Cys-Cys disulfide bonded to Cys
<220> FEATURE:
<221> NAME/KEY: VARIANT
<222> LOCATION: (3), (7)
<223> OTHER INFORMATION: Xaa = D-Ala
<220> FEATURE:
<221> NAME/KEY: VARIANT
<222> LOCATION: (4), (5), (6), (8)
<223> OTHER INFORMATION: Xaa = D-Arg

<400> SEQUENCE: 62

Xaa Xaa Xaa Xaa Xaa Xaa Xaa Xaa
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg

<400> SEQUENCE: 63

Xaa Gly Xaa Xaa Xaa Gly Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg

<400> SEQUENCE: 64

Xaa Ala Xaa Xaa Xaa Ala Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Val
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 65

Xaa Xaa Xaa Xaa Xaa Xaa Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Val
<220> FEATURE:
<221> NAME/KEY: VARIANT
<222> LOCATION: (3), (4), (5), (7)
<223> OTHER INFORMATION: Xaa = D-Arg

<400> SEQUENCE: 66

Xaa Xaa Xaa Xaa Xaa Xaa Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 67
```

```
Xaa Xaa Xaa Xaa Xaa Xaa Xaa
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Glu
<220> FEATURE:
<221> NAME/KEY: MOD_RES
<222> LOCATION: (7)
<223> OTHER INFORMATION: C-terminal amidation

<400> SEQUENCE: 68

Xaa Xaa Xaa Xaa Xaa Xaa Xaa
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Glu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 69

Xaa Xaa Xaa Xaa Xaa Xaa Xaa
1               5
```

```
<210> SEQ ID NO 70
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), 6)
<223> OTHER INFORMATION: Xaa = D-Ala
<220> FEATURE:
<221> NAME/KEY: VARIANT
<222> LOCATION: (3), (4), (5)
<223> OTHER INFORMATION: Xaa = D-Arg
<220> FEATURE:
<221> NAME/KEY: VARIANT
<222> LOCATION: (7)
<223> OTHER INFORMATION: Xaa = D-Lys
<220> FEATURE:
<221> NAME/KEY: MOD_RES
<222> LOCATION: (7)
<223> OTHER INFORMATION: C-terminal amidation

<400> SEQUENCE: 70

Xaa Xaa Xaa Xaa Xaa Xaa Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Glu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 71

Xaa Xaa Xaa Xaa Xaa Xaa Xaa
1               5

<210> SEQ ID NO 72
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3)
<223> OTHER INFORMATION: Xaa = D-Lys
<220> FEATURE:
<221> NAME/KEY: VARIANT
<222> LOCATION: (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 72

Xaa Xaa Xaa Xaa Xaa Xaa Xaa
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (4)
<223> OTHER INFORMATION: Xaa = D-Lys
<220> FEATURE:
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 73

Xaa Xaa Xaa Xaa Xaa Xaa Xaa
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
```

```
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 74

Xaa Xaa Xaa Xaa Xaa Xaa Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: MOD_RES
<222> LOCATION: (7)
<223> OTHER INFORMATION: C-terminal amidation

<400> SEQUENCE: 75

Cys Ala Arg Arg Arg Ala Arg
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3)
<223> OTHER INFORMATION: Xaa = D-Ala
<220> FEATURE:
<221> NAME/KEY: VARIANT
<222> LOCATION: (4)...(9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation

<400> SEQUENCE: 76

Xaa Xaa Xaa Xaa Xaa Xaa Xaa Xaa Xaa
1               5

<210> SEQ ID NO 77
<211> LENGTH: 10
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (4)
<223> OTHER INFORMATION: Xaa = D-Ala
<220> FEATURE:
<221> NAME/KEY: VARIANT
<222> LOCATION: (5)...(10)
<223> OTHER INFORMATION: Xaa = D-Arg
<220> FEATURE:
<221> NAME/KEY: MOD_RES
<222> LOCATION: (10)
<223> OTHER INFORMATION: C-terminal amidation

<400> SEQUENCE: 77

Xaa Xaa Xaa Xaa Xaa Xaa Xaa Xaa Xaa Xaa
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (6), (8)
<223> OTHER INFORMATION: Xaa = D-Ala
<220> FEATURE:
<221> NAME/KEY: VARIANT
<222> LOCATION: (3), (5), (7), (9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation

<400> SEQUENCE: 78

Xaa Xaa Xaa Xaa Xaa Xaa Xaa Xaa Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
```

```
<221> NAME/KEY: VARIANT
<222> LOCATION: (2), (6), (8)
<223> OTHER INFORMATION: Xaa = D-Ala
<220> FEATURE:
<221> NAME/KEY: VARIANT
<222> LOCATION: (3), (4), (5), (7), (9)
<223> OTHER INFORMATION: Xaa = D-Arg
<220> FEATURE:
<221> NAME/KEY: MOD_RES
<222> LOCATION: (9)
<223> OTHER INFORMATION: C-terminal amidation

<400> SEQUENCE: 79

Xaa Xaa Xaa Xaa Xaa Xaa Xaa Xaa Xaa
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 80

Xaa Xaa Xaa Xaa Xaa Xaa Xaa
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys interchain bond with benzoyl
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 81

Xaa Xaa Xaa Xaa Xaa Xaa Xaa
1               5

<210> SEQ ID NO 82
<211> LENGTH: 7
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Cys-Cys interchain bond with acetyl
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 82

Xaa Xaa Xaa Xaa Xaa Xaa Xaa
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Phe
<220> FEATURE:
<221> NAME/KEY: MOD_RES
<222> LOCATION: (7)
<223> OTHER INFORMATION: C-terminal amidation

<400> SEQUENCE: 83

Xaa Xaa Xaa Xaa Xaa Xaa Xaa
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
```

```
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ile
<220> FEATURE:
<221> NAME/KEY: MOD_RES
<222> LOCATION: (7)
<223> OTHER INFORMATION: C-terminal amidation

<400> SEQUENCE: 84

Xaa Xaa Xaa Xaa Xaa Xaa Xaa
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Leu
<220> FEATURE:
<221> NAME/KEY: MOD_RES
<222> LOCATION: (7)
<223> OTHER INFORMATION: C-terminal amidation

<400> SEQUENCE: 85

Xaa Xaa Xaa Xaa Xaa Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
```

```
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = D-Arg
<220> FEATURE:
<221> NAME/KEY: VARIANT
<222> LOCATION: (5)
<223> OTHER INFORMATION: Xaa = D-Lys
<220> FEATURE:
<221> NAME/KEY: MOD_RES
<222> LOCATION: (7)
<223> OTHER INFORMATION: C-terminal amidation

<400> SEQUENCE: 86

Xaa Xaa Xaa Xaa Xaa Xaa Xaa
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Val
<220> FEATURE:
<221> NAME/KEY: MOD_RES
<222> LOCATION: (7)
<223> OTHER INFORMATION: C-terminal amidation

<400> SEQUENCE: 87

Xaa Xaa Xaa Xaa Xaa Xaa Xaa
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
```

```
<220> FEATURE:
<221> NAME/KEY: VARIANT
<222> LOCATION: (6)
<223> OTHER INFORMATION: Xaa = D-Pro
<220> FEATURE:
<221> NAME/KEY: MOD_RES
<222> LOCATION: (7)
<223> OTHER INFORMATION: C-terminal amidation

<400> SEQUENCE: 88

Xaa Xaa Xaa Xaa Xaa Xaa Xaa
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-His
<220> FEATURE:
<221> NAME/KEY: MOD_RES
<222> LOCATION: (7)
<223> OTHER INFORMATION: C-terminal amidation

<400> SEQUENCE: 89

Xaa Xaa Xaa Xaa Xaa Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Gln
<220> FEATURE:
```

```
<221> NAME/KEY: MOD_RES
<222> LOCATION: (7)
<223> OTHER INFORMATION: C-terminal amidation

<400> SEQUENCE: 90

Xaa Xaa Xaa Xaa Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Thr
<220> FEATURE:
<221> NAME/KEY: MOD_RES
<222> LOCATION: (7)
<223> OTHER INFORMATION: C-terminal amidation

<400> SEQUENCE: 91

Xaa Xaa Xaa Xaa Xaa Xaa Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ser
<220> FEATURE:
<221> NAME/KEY: MOD_RES
<222> LOCATION: (7)
<223> OTHER INFORMATION: C-terminal amidation

<400> SEQUENCE: 92
```

```
Xaa Xaa Xaa Xaa Xaa Xaa Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 93

Xaa Xaa Xaa Xaa Xaa Gly Xaa
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Gle
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 94

Xaa Xaa Xaa Xaa Xaa Xaa Xaa
1               5

<210> SEQ ID NO 95
<211> LENGTH: 7
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 95

Xaa Gly Xaa Xaa Xaa Xaa Xaa
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ile
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 96

Xaa Xaa Xaa Xaa Xaa Xaa Xaa
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
```

```
<223> OTHER INFORMATION: N-terminal acetylation
<220> FEATURE:
<221> NAME/KEY: VARIANT
<222> LOCATION: (2)
<223> OTHER INFORMATION: Xaa = D-Pro
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 97

Xaa Xaa Xaa Xaa Xaa Xaa Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Leu
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 98

Xaa Xaa Xaa Xaa Xaa Xaa Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Gln
```

```
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 99

Xaa Xaa Xaa Xaa Xaa Xaa Xaa
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Thr
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 100

Xaa Xaa Xaa Xaa Xaa Xaa Xaa
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Val
<220> FEATURE:
<221> NAME/KEY: VARIANT
<222> LOCATION: (3), (4), (5), (7)
<223> OTHER INFORMATION: Xaa = D-Arg
<220> FEATURE:
```

```
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 101

Xaa Xaa Xaa Xaa Xaa Xaa Xaa
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ser
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 102

Xaa Xaa Xaa Xaa Xaa Xaa Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-His
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
```

```
<222> LOCATION: (7)
<223> OTHER INFORMATION: C-terminal amidation

<400> SEQUENCE: 103

Xaa Xaa Xaa Xaa Xaa Xaa Xaa
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Phe
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 104

Xaa Xaa Xaa Xaa Xaa Xaa Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 105

Xaa Xaa Xaa Gly Xaa Xaa Xaa
1               5
```

```
<210> SEQ ID NO 106
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Pro
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 106

Xaa Xaa Xaa Xaa Xaa Xaa Xaa
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Glu
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 107

Xaa Xaa Xaa Xaa Xaa Xaa Xaa
1               5

<210> SEQ ID NO 108
<211> LENGTH: 7
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Thr
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 108

Xaa Xaa Xaa Xaa Xaa Xaa Xaa
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-His
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 109

Xaa Xaa Xaa Xaa Xaa Xaa Xaa
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
```

```
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Phe
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 110

Xaa Xaa Xaa Xaa Xaa Xaa Xaa
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ser
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 111

Xaa Xaa Xaa Xaa Xaa Xaa Xaa
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
```

```
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Gln
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 112

Xaa Xaa Xaa Xaa Xaa Xaa Xaa
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Val
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 113

Xaa Xaa Xaa Xaa Xaa Xaa Xaa
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
```

```
<222> LOCATION: (4)
<223> OTHER INFORMATION: Xaa = D-Leu
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 114

Xaa Xaa Xaa Xaa Xaa Xaa Xaa
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ile
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 115

Xaa Xaa Xaa Xaa Xaa Xaa Xaa
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = N-methylglycine (sarcosine)
<220> FEATURE:
<221> NAME/KEY: VARIANT
<222> LOCATION: (6)
```

```
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 116

Xaa Xaa Xaa Xaa Xaa Xaa Xaa
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = N-methylglycine (sarcosine)
<220> FEATURE:
<221> NAME/KEY: MOD_RES
<222> LOCATION: (7)
<223> OTHER INFORMATION: C-terminal amidation

<400> SEQUENCE: 117

Xaa Xaa Xaa Xaa Xaa Xaa Xaa
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = N-methylalanine (Nma)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 118

Xaa Xaa Xaa Xaa Xaa Xaa Xaa
```

```
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = N-methylalanine (Nma)
<220> FEATURE:
<221> NAME/KEY: MOD_RES
<222> LOCATION: (7)
<223> OTHER INFORMATION: C-terminal amidation

<400> SEQUENCE: 119

Xaa Xaa Xaa Xaa Xaa Xaa Xaa
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = 2-aminoisobutyric acid (Aib)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 120

Xaa Xaa Xaa Xaa Xaa Xaa Xaa
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = N-methylalanine (Nma)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 121

Xaa Xaa Xaa Xaa Xaa Xaa Xaa
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = N-methylalanine (Nma)
<220> FEATURE:
<221> NAME/KEY: MOD_RES
<222> LOCATION: (7)
<223> OTHER INFORMATION: C-terminal amidation

<400> SEQUENCE: 122

Xaa Xaa Xaa Xaa Xaa Xaa Xaa
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
```

```
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = 2-aminoisobutyric acid (Aib)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 123

Xaa Xaa Xaa Xaa Xaa Xaa Xaa
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = 2-aminoisobutyric acid (Aib)
<220> FEATURE:
<221> NAME/KEY: MOD_RES
<222> LOCATION: (7)
<223> OTHER INFORMATION: C-terminal amidation

<400> SEQUENCE: 124

Xaa Xaa Xaa Xaa Xaa Xaa Xaa
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
```

```
<222> LOCATION: (2), (6)
<223> OTHER INFORMATION: Xaa = N-methylglycine (sarcosine)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 125

Xaa Xaa Xaa Xaa Xaa Xaa Xaa
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = N-methylglycine (sarcosine)
<220> FEATURE:
<221> NAME/KEY: MOD_RES
<222> LOCATION: (7)
<223> OTHER INFORMATION: C-terminal amidation

<400> SEQUENCE: 126

Xaa Xaa Xaa Xaa Xaa Xaa Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = N-methylalanine (Nma)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
```

```
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 127

Xaa Xaa Xaa Xaa Xaa Xaa Xaa
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = N-methylglycine (sarcosine)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 128

Xaa Xaa Xaa Xaa Xaa Xaa Xaa
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = Norleucine (NLeu)
<220> FEATURE:
<221> NAME/KEY: MOD_RES
<222> LOCATION: (7)
<223> OTHER INFORMATION: C-terminal amidation
```

```
<400> SEQUENCE: 129

Xaa Xaa Xaa Xaa Xaa Xaa Xaa
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Norleucine (dNLeu)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 130

Xaa Xaa Xaa Xaa Xaa Xaa Xaa
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Norvaline (dNval)
<220> FEATURE:
<221> NAME/KEY: MOD_RES
<222> LOCATION: (7)
<223> OTHER INFORMATION: C-terminal amidation

<400> SEQUENCE: 131

Xaa Xaa Xaa Xaa Xaa Xaa Xaa
1               5

<210> SEQ ID NO 132
<211> LENGTH: 7
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Norvaline (dNval)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 132

Xaa Xaa Xaa Xaa Xaa Xaa Xaa
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Norleucine (dNLeu)
<220> FEATURE:
<221> NAME/KEY: MOD_RES
<222> LOCATION: (7)
<223> OTHER INFORMATION: C-terminal amidation

<400> SEQUENCE: 133

Xaa Xaa Xaa Xaa Xaa Xaa Xaa
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
```

```
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)
<223> OTHER INFORMATION: Xaa = D-Norleucine (dNLeu)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 134

Xaa Xaa Xaa Xaa Xaa Xaa Xaa
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-Norvaline (dNVal)
<220> FEATURE:
<221> NAME/KEY: MOD_RES
<222> LOCATION: (7)
<223> OTHER INFORMATION: C-terminal amidation

<400> SEQUENCE: 135

Xaa Xaa Xaa Xaa Xaa Xaa Xaa
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
```

```
<222> LOCATION: (2)
<223> OTHER INFORMATION: Xaa = D-Norvaline (dNVal)
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 136

Xaa Xaa Xaa Xaa Xaa Xaa Xaa
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Norvaline (dNVal)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 137

Xaa Xaa Xaa Xaa Xaa Xaa Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
```

```
<223> OTHER INFORMATION: Xaa = D-Norleucine (dNLeu)
<220> FEATURE:
<221> NAME/KEY: VARIANT
<222> LOCATION: (6)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 138

Xaa Xaa Xaa Xaa Xaa Xaa Xaa
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with D-homocysteine (dHcy)
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 139

Xaa Xaa Xaa Xaa Xaa Xaa Xaa
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with 3-mercaptopropionic acid (Mpa)
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
```

```
<220> FEATURE:
<221> NAME/KEY: MOD_RES
<222> LOCATION: (7)
<223> OTHER INFORMATION: C-terminal amidation

<400> SEQUENCE: 140

Xaa Xaa Xaa Xaa Xaa Xaa Xaa
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with acetylated L-Cysteine
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 141

Xaa Xaa Xaa Xaa Xaa Xaa Xaa
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with D-Cysteine
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation
```

-continued

<400> SEQUENCE: 142

Xaa Xaa Xaa Xaa Xaa Xaa Xaa
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 143

Xaa Xaa Xaa Xaa Xaa Xaa Xaa
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: DISULFID
<222> LOCATION: (1)..(1)
<223> OTHER INFORMATION: Bond with Polyethylene glycol
<220> FEATURE:
<221> NAME/KEY: VARIANT
<222> LOCATION: (2)...(7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 144

Xaa Xaa Xaa Xaa Xaa Xaa Xaa
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 145

Cys Glu Glu Glu Glu Glu
1               5

<210> SEQ ID NO 146
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2)...(5)
<223> OTHER INFORMATION: Xaa = D-Arg
<220> FEATURE:
<221> NAME/KEY: VARIANT
<222> LOCATION: (6), (7)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 146

Xaa Xaa Xaa Xaa Xaa Xaa Xaa
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5), (7)
<223> OTHER INFORMATION: Xaa = D-Lys
<220> FEATURE:
<221> NAME/KEY: MOD_RES
<222> LOCATION: (7)
<223> OTHER INFORMATION: C-terminal amidation

<400> SEQUENCE: 147

Xaa Xaa Xaa Xaa Xaa Xaa Xaa
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (4), (6)
<223> OTHER INFORMATION: Xaa = D-Ala
<220> FEATURE:
<221> NAME/KEY: VARIANT
<222> LOCATION: (3), (5), (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation

<400> SEQUENCE: 148

Xaa Xaa Xaa Xaa Xaa Xaa Xaa
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: MOD_RES
<222> LOCATION: (7)
<223> OTHER INFORMATION: C-terminal amidation

<400> SEQUENCE: 149

Xaa Xaa Xaa Xaa Xaa Gly Xaa
1               5

<210> SEQ ID NO 150
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
```

```
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-Gln
<220> FEATURE:
<221> NAME/KEY: MOD_RES
<222> LOCATION: (7)
<223> OTHER INFORMATION: C-terminal amidation

<400> SEQUENCE: 150

Xaa Xaa Xaa Xaa Xaa Xaa Xaa
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
<223> OTHER INFORMATION: Xaa = D-His
<220> FEATURE:
<221> NAME/KEY: MOD_RES
<222> LOCATION: (7)
<223> OTHER INFORMATION: C-terminal amidation

<400> SEQUENCE: 151

Xaa Xaa Xaa Xaa Xaa Xaa Xaa
1               5

<210> SEQ ID NO 152
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (3), (5), (7)
<223> OTHER INFORMATION: Xaa = D-Arg
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (6)
```

```
<223> OTHER INFORMATION: Xaa = D-Ile
<220> FEATURE:
<221> NAME/KEY: MOD_RES
<222> LOCATION: (7)
<223> OTHER INFORMATION: C-terminal amidation

<400> SEQUENCE: 152

Xaa Xaa Xaa Xaa Xaa Xaa Xaa
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (5)
<223> OTHER INFORMATION: Xaa = D-Ala
<220> FEATURE:
<221> NAME/KEY: DISULFID
<222> LOCATION: (2)..(2)
<223> OTHER INFORMATION: Bond with 1,3-diaminopropionic acid (DAP)
<220> FEATURE:
<221> NAME/KEY: VARIANT
<222> LOCATION: (3), (4), (6)
<223> OTHER INFORMATION: Xaa = D-Arg
<220> FEATURE:
<221> NAME/KEY: MOD_RES
<222> LOCATION: (6)
<223> OTHER INFORMATION: C-terminal amidation

<400> SEQUENCE: 153

Xaa Xaa Xaa Xaa Xaa Xaa
1               5

<210> SEQ ID NO 154
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: MOD_RES
<222> LOCATION: (1)..(1)
<223> OTHER INFORMATION: N-terminal acetylation
<220> FEATURE:
<221> NAME/KEY: VARIANT
<222> LOCATION: (2), (6)
<223> OTHER INFORMATION: Xaa = D-Ala
<220> FEATURE:
<221> NAME/KEY: VARIANT
<222> LOCATION: (3), (4), (5)
<223> OTHER INFORMATION: Xaa = D-Homoarginine
<220> FEATURE:
<221> NAME/KEY: VARIANT
<222> LOCATION: (7)
<223> OTHER INFORMATION: Xaa = D-Arg
<220> FEATURE:
<221> NAME/KEY: MOD_RES
<222> LOCATION: (7)
<223> OTHER INFORMATION: C-terminal amidation
```

<400> SEQUENCE: 154

Xaa Xaa Xaa Xaa Xaa Xaa Xaa
1               5

<210> SEQ ID NO 155
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = a thiol-containing amino acid residue
<220> FEATURE:
<221> NAME/KEY: VARIANT
<222> LOCATION: (2)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = a cationic amino acid residue
<220> FEATURE:
<221> NAME/KEY: VARIANT
<222> LOCATION: (6)
<223> OTHER INFORMATION: Xaa = a non-cationic amino acid residue

<400> SEQUENCE: 155

Xaa Xaa Xaa Xaa Xaa Xaa Xaa
1               5

<210> SEQ ID NO 156
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys
<220> FEATURE:
<221> NAME/KEY: VARIANT
<222> LOCATION: (6)
<223> OTHER INFORMATION: Xaa = a non-cationic amino acid residue

<400> SEQUENCE: 156

Xaa Xaa Xaa Xaa Xaa Xaa Xaa
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide

```
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (3), (4)
<223> OTHER INFORMATION: Xaa = any amino acid residue
<220> FEATURE:
<221> NAME/KEY: VARIANT
<222> LOCATION: (5), (7)
<223> OTHER INFORMATION: Xaa = any cationic amino acid residue
<220> FEATURE:
<221> NAME/KEY: VARIANT
<222> LOCATION: (6)
<223> OTHER INFORMATION: Xaa = a non-cationic amino acid residue

<400> SEQUENCE: 157

Xaa Xaa Xaa Xaa Xaa Xaa Xaa
1               5

<210> SEQ ID NO 158
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (6)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys

<400> SEQUENCE: 158

Xaa Xaa Xaa Xaa Xaa Xaa Xaa
1               5

<210> SEQ ID NO 159
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = any cationic amino acid residue
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala
```

```
<400> SEQUENCE: 159

Xaa Xaa Xaa Xaa Xaa Xaa Xaa
1               5

<210> SEQ ID NO 160
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2), (3), (7)
<223> OTHER INFORMATION: Xaa = any cationic amino acid residue
<220> FEATURE:
<221> NAME/KEY: VARIANT
<222> LOCATION: (4)
<223> OTHER INFORMATION: Xaa = D-Ala
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala

<400> SEQUENCE: 160

Xaa Xaa Xaa Xaa Xaa Xaa Xaa
1               5

<210> SEQ ID NO 161
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = D-Cys
<220> FEATURE:
<221> NAME/KEY: VARIANT
<222> LOCATION: (2)
<223> OTHER INFORMATION: Xaa = D-Ala
<220> FEATURE:
<221> NAME/KEY: VARIANT
<222> LOCATION: (3), (4), (7)
<223> OTHER INFORMATION: Xaa = any amino acid
<220> FEATURE:
<221> NAME/KEY: VARIANT
<222> LOCATION: (5)
<223> OTHER INFORMATION: Xaa = D-Arg
<220> FEATURE:
<221> NAME/KEY: VARIANT
<222> LOCATION: (6)
<223> OTHER INFORMATION: Xaa = D-Ala

<400> SEQUENCE: 161

Xaa Xaa Xaa Xaa Xaa Xaa Xaa
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 162

His Asp Ala Pro Ile Gly Tyr Asp
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic peptide

<400> SEQUENCE: 163

Cys His Asp Ala Pro Ile Gly Tyr Asp
1               5

<210> SEQ ID NO 164
<211> LENGTH: 11
<212> TYPE: PRT
<213> ORGANISM: Artificial Sequence
<220> FEATURE:
<223> OTHER INFORMATION: Synthetic peptide

<400> SEQUENCE: 164

Tyr Gly Arg Lys Lys Arg Arg Gln Arg Arg Arg
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic peptide

<400> SEQUENCE: 165

Cys Tyr Gly Arg Lys Lys Arg Arg Gln Arg Arg Arg
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Synthetic peptide

<400> SEQUENCE: 166

Cys Ser Phe Asn Ser Tyr Glu Leu Gly Ser Leu
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Synthetic peptide

<400> SEQUENCE: 167

Cys Pro Asp Tyr His Asp Ala Gly Ile
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic peptide

<400> SEQUENCE: 168
```

Cys Glu Ala Val Ser Leu Lys Pro Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic peptide

<400> SEQUENCE: 169

Glu Ser Val Ser Leu Lys Pro Thr
1               5

<210> SEQ ID NO 170
<211> LENGTH: 14
<212> TYPE: PRT
<213> ORGANISM: Artificial Sequence
<220> FEATURE:
<223> OTHER INFORMATION: Synthetic peptide

<400> SEQUENCE: 170

Cys Arg Phe Ala Arg Lys Gly Ala Leu Arg Gln Lys Asn Val
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Synthetic peptide

<400> SEQUENCE: 171

Tyr Gly Arg Lys Lys Arg
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic peptide

<400> SEQUENCE: 172

Cys Tyr Gly Arg Lys Lys Arg
1               5

<210> SEQ ID NO 173
<211> LENGTH: 11
<212> TYPE: PRT
<213> ORGANISM: Artificial Sequence
<220> FEATURE:
<223> OTHER INFORMATION: Synthetic peptide

<400> SEQUENCE: 173

Tyr Gly Arg Arg Ala Arg Arg Arg Ala Arg Arg
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Synthetic peptide

<400> SEQUENCE: 174

Cys Tyr Gly Arg Arg Ala Arg Arg Ala Arg Arg
1               5                   10

<210> SEQ ID NO 175
<211> LENGTH: 4
<212> TYPE: PRT
<213> ORGANISM: Artificial Sequence
<220> FEATURE:
<223> OTHER INFORMATION: Synthetic peptide

<400> SEQUENCE: 175

Cys Arg Arg Arg
1

<210> SEQ ID NO 176
<211> LENGTH: 5
<212> TYPE: PRT
<213> ORGANISM: Artificial Sequence
<220> FEATURE:
<223> OTHER INFORMATION: Synthetic peptide

<400> SEQUENCE: 176

Cys Arg Arg Arg Arg
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic peptide

<400> SEQUENCE: 177

Cys Arg Arg Arg Arg Arg Arg Arg
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic peptide

<400> SEQUENCE: 178

Cys Arg Arg Arg Arg Arg Arg Arg Arg
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide

<400> SEQUENCE: 179

Cys Arg Arg Arg Arg Arg Arg Arg Arg Arg
1               5                   10

<210> SEQ ID NO 180
<211> LENGTH: 11
<212> TYPE: PRT
<213> ORGANISM: Artificial Sequence

```
<220> FEATURE:
<223> OTHER INFORMATION: Synthetic peptide

<400> SEQUENCE: 180

Cys Arg Arg Arg Arg Arg Arg Arg Arg Arg
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Synthetic peptide

<400> SEQUENCE: 181

Cys Arg Arg Arg Arg Arg Arg Arg Arg Arg Arg
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Synthetic peptide

<400> SEQUENCE: 182

Cys Arg Arg Arg Arg Arg Arg Arg Arg Arg Arg Arg
1               5                   10

<210> SEQ ID NO 183
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)
<223> OTHER INFORMATION: Xaa = L-Cys
<220> FEATURE:
<221> NAME/KEY: VARIANT
<222> LOCATION: (2), (6)
<223> OTHER INFORMATION: Xaa = a non-cationic amino acid residue
<220> FEATURE:
<221> NAME/KEY: VARIANT
<222> LOCATION: (3), (4), (7)
<223> OTHER INFORMATION: Xaa = any amino acid residue
<220> FEATURE:
<221> NAME/KEY: VARIANT
<222> LOCATION: (5)
<223> OTHER INFORMATION: Xaa = D-Arg, L-Arg, D-Lys or L-Lys

<400> SEQUENCE: 183

Xaa Xaa Xaa Xaa Xaa Xaa Xaa
1               5
```